US009822068B2

(12) United States Patent
Piomelli et al.

(10) Patent No.: US 9,822,068 B2
(45) Date of Patent: Nov. 21, 2017

(54) INHIBITORS OF FATTY ACID AMIDE HYDROLASE (FAAH) ENZYME WITH IMPROVED ORAL BIOAVAILABILITY AND THEIR USE AS MEDICAMENTS

(71) Applicants: THE REGENTS OF THE UNIVERSITY OF CALIFORNIA, Oakland, CA (US); FONDAZIONE ISTITUTO ITALIANO DI TECNOLOGIA, Genoa (IT)

(72) Inventors: Daniele Piomelli, Irvine, CA (US); Tiziano Bandiera, Gambolo (IT); Rita Scarpelli, Rome (IT)

(73) Assignees: The Regents of the University of California, Oakland, CA (US); Fondazione Istituto Italiano di Technologia, Genoa (IT)

( * ) Notice: Subject to any disclaimer, the term of this patent is extended or adjusted under 35 U.S.C. 154(b) by 0 days.

(21) Appl. No.: 15/287,366

(22) Filed: Oct. 6, 2016

(65) Prior Publication Data

US 2017/0088510 A1 Mar. 30, 2017

Related U.S. Application Data

(63) Continuation of application No. PCT/US2015/024753, filed on Apr. 7, 2015.

(60) Provisional application No. 61/976,439, filed on Apr. 7, 2014.

(51) Int. Cl.
*C07C 271/56* (2006.01)
*C07C 311/29* (2006.01)
*C07C 317/22* (2006.01)

(52) U.S. Cl.
CPC .......... *C07C 271/56* (2013.01); *C07C 311/29* (2013.01); *C07C 317/22* (2013.01); *C07C 2601/04* (2017.05); *C07C 2601/08* (2017.05); *C07C 2601/14* (2017.05)

(58) Field of Classification Search
CPC .................................................... C07C 271/56
See application file for complete search history.

(56) References Cited

U.S. PATENT DOCUMENTS

| | | | |
|---|---|---|---|
| 4,325,889 | A | 4/1982 | Behre et al. |
| 4,458,066 | A | 7/1984 | Caruthers et al. |
| 4,511,503 | A | 4/1985 | Olson et al. |
| 5,541,061 | A | 7/1996 | Fodor et al. |
| 5,559,410 | A | 9/1996 | Papazian et al. |
| 5,576,220 | A | 11/1996 | Hudson et al. |
| 5,952,315 | A | 9/1999 | Baker et al. |
| 5,962,012 | A | 10/1999 | Lin et al. |
| 6,261,595 | B1 | 7/2001 | Stanley et al. |
| 6,271,015 | B1 | 8/2001 | Gilula et al. |
| 6,313,174 | B1 | 11/2001 | Ottosen et al. |
| 6,326,156 | B1 | 12/2001 | Civelli et al. |
| 6,344,474 | B1 | 2/2002 | Maruani et al. |
| 6,403,573 | B1 | 6/2002 | Leysen et al. |
| 7,192,975 | B2 | 3/2007 | Bigg et al. |
| 9,187,413 | B2 | 11/2015 | Piomelli et al. |
| 2002/0173550 | A1 | 11/2002 | Calignano et al. |
| 2003/0134894 | A1 | 7/2003 | Piomelli et al. |
| 2003/0149082 | A1 | 8/2003 | Makriyannis et al. |
| 2004/0048907 | A1 | 3/2004 | Aquila et al. |
| 2004/0127518 | A1 | 7/2004 | Piomelli et al. |
| 2007/0155707 | A1 | 7/2007 | Dasse et al. |
| 2009/0048337 | A1 | 2/2009 | Piomelli et al. |
| 2014/0163034 | A1 | 6/2014 | Piomelli et al. |
| 2014/0288170 | A1 | 9/2014 | Piomelli et al. |

FOREIGN PATENT DOCUMENTS

| | | | |
|---|---|---|---|
| CN | 1671701 | A | 9/2005 |
| CN | 1729171 | A | 2/2006 |
| CN | 1741990 | A | 3/2006 |
| CN | 1922162 | A | 2/2007 |
| JP | 2006/511484 | | 4/2006 |
| WO | WO-98/20119 | A1 | 5/1998 |
| WO | WO-03/097573 | | 11/2003 |
| WO | WO-2004/033422 | A2 | 4/2004 |
| WO | WO-2004/033422 | A3 | 4/2004 |
| WO | WO-2008/063714 | A1 | 5/2008 |
| WO | WO-2008/067196 | A2 | 6/2008 |
| WO | WO-2008/067196 | A3 | 6/2008 |
| WO | WO-2009/109504 | A1 | 9/2009 |
| WO | WO-2011/046954 | A1 | 4/2011 |
| WO | WO-2012/015704 | A2 | 2/2012 |
| WO | WO-2012/015704 | A3 | 2/2012 |
| WO | WO-2012/167133 | A2 | 12/2012 |
| WO | WO-2012/167133 | A3 | 12/2012 |
| WO | WO-2013/028570 | A2 | 2/2013 |
| WO | WO-2013/028570 | A3 | 2/2013 |
| WO | WO-2015/157313 | A1 | 10/2015 |

OTHER PUBLICATIONS

Glaucoma [online], retrieved from the internet on Feb. 6, 2017, URL; http://www.mayoclinic.org/diseases-conditions/glaucoma/basics/prevention/con-20024042.*

Agarwal, N. et al. (2007). "Cannabinoids mediate analgesia largely via peripheral type 1 cannabinoid receptors in nociceptors" *Nat. Neurosci* 10 (7), 870-879.

Ahn, K. et al. Novel Mechanistic Class of Fatty Acid Amide Hydrolase Inhibitors with Remarkable Selectivity. Biochemistry. 2007, vol. 46, pp. 13019-13030.

Ahn, K. et al. (May 2008, e-published Apr. 23, 2008). "Enzymatic pathways that regulate endocannabinoid signaling in the nervous system," Chem Rev 108(5):1687-1707.

Alexander, J.P. et al. (2005). "Mechanism of carbamate inactivation of FAAH: implications for the design of covalent inhibitors and in vivo functional probes for enzymes," *Chem Biol* 12 (11), 1179-1187.

(Continued)

*Primary Examiner* — Shawquia Jackson
(74) *Attorney, Agent, or Firm* — Anson M. Nomura; Mintz, Levin, Cohn, Ferris, Glovsky and Popeo, P.C.

(57) ABSTRACT

Described herein, inter alia, are compositions and methods useful for inhibiting fatty acid amide hydrolase.

20 Claims, No Drawings

(56) References Cited

OTHER PUBLICATIONS

Anand, P. et al. (2009). "Targeting CB2 receptors and the endocannabinoid system for the treatment of pain," *Brain Res Rev* 60(1):255-266.
Astarita, G. et al. (Jan. 2008, e-published Oct. 23, 2007). Identification of biosynthetic precursors for the endocannabinoid anandamide in the rat brain. *J Lipid Res* 49(1):48-57.
Beltramo, M. et al. (Feb. 24, 1997). "Inhibition of anandamide hydrolysis in rat brain tissue by (E)-6-(bromomethylene) tetrahydro-3-(1-naphthalenyl)-2H-pyran-2-one," *FEBS Lett.* 403(3):263-267.
Beltramo, M. et al. (Aug. 22, 1997). "Functional role of high-affinity anandamide transport, as revealed by selective inhibition," *Science* 277(5329):1094-1097.
Beltramo, M. et al. (Apr. 27, 2000). "Carrier-mediated transport and enzymatic hydrolysis of the endogenous cannabinoid 2-arachidonylglycerol," *Neuroreport*, 11(6):1231-1235.
Beltramo, M. et al. (May 2000). "Reversal of dopamine D(2) receptor responses by an anandamide transport inhibitor,"*J Neurosci* 20(9):3401-3407.
Bennett, G.J. et al. (1988). "A peripheral mononeuropathy in rat that produces disorders of pain sensation like those seen in man," *Pain* 33(1):87-107.
Bisogno, T., et al. (2002). "Fatty acid amide hydrolase, an enzyme with many bioactive substrates. Possible therapeutic implications," *Curr. Pharm. Des.* 8(7):533-547.
Boger, D.L. et al. (Aug. 1998). "Oleamide: an endogenous sleep-inducing lipid and prototypical member of a new class of biological signaling molecules," *Curr Pharm Des* 4(4):303-314.
Boger, D. L. et al. (2005). *J Med Chem*, 48, 1849-1856.
Cadas, H. et al. (Feb. 15, 1997). Occurrence and biosynthesis of endogenous cannabinoid precursor, N-arachidonoyl phosphatidylethanolamine, in rat brain. *J Neurosci* 17 (4):1226-1242.
Calignano, A. et al. (1998). "Control of pain initiation by endogenous cannabinoids," *Nature* 394 (6690) :277-281.
Calignano, A. et al. (2001). "Antinociceptive activity of the endogenous fatty acid amide, palmitylethanolamide," *Eur J Pharmacol* 419 (2-3), 191-198.
Casarotto, P.C. et al. (Jul. 2010). "Cannabidiol inhibitory effect on marble-burying behaviour: involvement of CB1 receptors," *Behav Pharmacol* 21(4):353-358.
Casarotto, P.C. et al. (2016). "Unbound Medline: Cannabidiol Inhibitory Effect on Marble-Burying Behaviour: Involvmenet of CB1 Receptors," located at http://www.unboundmedicine.com/medline/citation/20695034/Cannabidiol_inhibitory_effect_on_marble_burying_behaviour_involvmenet_of_CB1_receptors, last accessed May 17, 2016, abstract only, 2 pages.
Cee, V. et al. (2000). Journal of Medicinal Chemistry 53: 6368-6377.
Chaperon, F. et al. (1999). "Behavioral effects of cannabinoid agents in animals," *Crit Rev Neurobiol* 13(3):243-281.
Cippitelli, et al. Eur J Neurosci 26(2) pp. 476-86 (2007).
Clapper, J.R. et al. (2009). "A second generation of carbamate-based fatty acid amide hydrolase inhibitors with improved activity in vivo," *ChemMedChem* 4(9):1505-1513.
Clapper, J.R. et al. (Oct. 2010, e-published Sep. 19, 2010). ""Anandamide suppresses pain initiation through a peripheral endocannabinoid mechanism,"" Nat. Neurosci 13(10)1265-1270.
Cravatt, B.F. et al. (1996). "Molecular characterization of an enzyme that degrades neuromodulatory fatty-acid amides," *Nature*, 384(6604):83-87.
Cravatt, B.F. et al. (2001). "Supersensitivity to anandamide and enhanced endogenous cannabinoid signaling in mice lacking fatty acid amide hydrolase," *Proc Natl Acad Sci USA* 98(16):9371-9376.
Cravatt, B.F. et al. (Aug. 2003). "Fatty acid amide hydrolase: an emerging therapeutic target in the endocannabinoid system," *Curr Opin Chem Biol* 7(4):469-475.
Cravatt, B.F. et al. (2004). "Functional disassociation of the central and peripheral fatty acid amide signaling systems," *Proc Natl Acad Sci USA* 101(29):10821-10826.
Del Arco et al., Eur J Pharmacol 454(1) pp. 103-104 (2002).
Deutsch, D.G., et al. (Feb.-Mar. 2002). "The fatty acid amide hydrolase (FAAH)," *Prostaglandins Leukot. Essent. Fatty Acid* 66(2-3):201-210.
Devane, W.A. et al. (1992). "Isolation and structure of a brain constituent that binds to the cannabinoid receptor. *Science*," 258(5090):1946-1949, abstract only.
Di Marzo, V. et al. (Dec. 15, 1994). "Formation and inactivation of endogenous cannabinoid anandamide in central neurons," *Nature*, 372:686-691.
Di Marzo, V. et al. (Apr. 2007). "Endocannabinoids and the regulation of their levels in health and disease," *Curr Opin Lipidol* 18(2):129-140.
Di Marzo, V. et al. (May 2008). "Targeting the endocannabinoid system: to enhance or reduce?" *Nat Rev Drug Discov* 7(5):438-455.
Dinh, T.P., et al. (Aug. 6, 2002, e-published Jul. 22, 2002). "Brain monoglyceride lipase participating in endocannabinoid inactivation," *Proc. Natl. Acad. Sci. U.S.A.* 99(16)10819-10824.
Duncton, M.A.J. et al. (2009). "Arylphthalazines as potent, and orally bioavailable inhibitors of VEGFR-2," *Bioorganic & Medicinal Chemistry* 17(2):731-740.
Dziadulewicz, E.K. et al. (2007). "Naphthalen-1-yl-(4-pentyloxynaphthalen-1-yl)methanone: a potent, orally bioavailable human CB1/CB2 dual agonist with antihyperalgesic properties and restricted central nervous system penetration," *J Med Chem* 50(16):3851-3856.
Eckert, H. et al. (1987). "Triphogene, a Crystalline Phosgene Substitute," *Angew Chem Int Ed Engl* 26(9):894-895.
Fegley, D. et al. (2005). "Characterization of the fatty acid amide hydrolase inhibitor cyclohexyl carbamic acid 3'-carbamoyl-biphenyl-3-yl ester (URB597): effects on anandamide and oleoylethanolamide deactivation," *J Pharmacol Exp Ther* 313(1):352-358.
Forster, L. et al. (Jan. 15, 2010, e-published Nov. 17, 2009). "1-Indol-1-yl-propan-2-ones and related heterocyclic compounds as dual inhibitors of cytosolic phospholipase A(2)alpha and fatty acid amide hydrolase," *Bioorg Med Chem* 18(2):945-952.
Fowler, C. J., et al. (Sep. 1, 2001). "Fatty acid amide hydrolase: biochemistry, pharmacology, and therapeutic possibilities for an enzyme hydrolyzing anandamide, 2-arachidonoylglycerol, palmitoylethanolamide, and oleamide," *Biochem. Pharmacol.* 62(5):517-526.
Fowler, C.J. (Jan. 2004, e-published Dec. 22, 2003). "Oleamide: a member of the endocannabinoid family?" *Br J Pharmacol* 141(2):195-196.
Fu, J.et al. (Sep. 4, 2003). "Oleylethanolamide regulates feeding and body weight through activation of the nuclear receptor PPAR-alpha," *Nature* 425(6953):90-93.
Fu, J. et al., J Biol Chem, 282(2):1518-1528. (2007).
Fu, J. et al., "A catalytically silent FAAH-1 variant drives anandamide transport in neurons", Nat. Neurosci., Nov. 20, 2011, vol. 15, No. 1, pp. 64-69.
Giuffrida, A. et al., Eur J Pharmacol, 408 161-168 (2000).
Glaser, S. T. et al., Proc Natl Acad Sci USA, 100(7):4269-4274. (2003).
Gomes, P.B. et al. (Sep. 2010, e-published May 31, 2010). "Anxiolytic-like effect of the monoterpene 1,4-cineole in mice," *Pharmacol Biochem Behav* 96(3):287-293.
Gomes et al. Prog Neuropsychopharmacol Biol Psychiatry. 35:434-438 (2011).
Guindon, J. et al. (2008). "Cannabinoid CB2 receptors: a therapeutic target for the treatment of inflammatory and neuropathic pain," *Br J Pharmacol* 153(2):319-334.
Hall, W., et al. (Nov. 14, 1998). "Adverse effects of cannabis," *Lancet*, 352(9140):1611-1616.
Hansen, H.S. et al. (Jul. 2010, e-publsihed Mar. 29, 2010). "Palmitoylethanolamide and other anandamide congeners. Proposed role in the diseased brain," *Exp Neurol* 224(1):48-55.
Hillard, C. J. et al., J Mol Neurosci, 33(1):18-24 (2007).

(56) References Cited

OTHER PUBLICATIONS

Hohmann, A.G. et al. (1999). "Localization of central cannabinoid CB1 receptor messenger RNA in neuronal subpopulations of rat dorsal root ganglia: a double-label in situ hybridization study," *Neuroscience* 90(3):923-931.
Hohmann, A.G. et al. (1999). "Cannabinoid receptors undergo axonal flow in sensory nerves," *Neuroscience* 92(4):1171-1175.
International Preliminary Report on Patentability dated Dec. 2, 2013 for International Application No. PCT/US2012/040531, 6 pages.
International Search Report and Written Opinion dated Mar. 22, 2013 for International Application No. PCT/US2012/040531, 9 pages.
International Search Report corresponding to the PCT/US2011/045114 application, dated Apr. 6, 2012, 4 pages.
International Search Report dated on Feb. 18, 2013, for PCT Application No. PCT/US2012/051478, filed Aug. 17, 2012, 4 pages.
International Search Report dated Aug. 25, 2015, for PCT Application No. PCT/US2015/024753, filed Apr. 7, 2015, 4 pages.
Jaggar, S.I. et al. (1998). "The endogenous cannabinoid anandamide, but not the CB2 ligand palmitoylethanolamide, prevents the viscero-visceral hyper-reflexia associated with inflammation of the rat urinary bladder," *Neurosci Lett* 253(2):123-126.
Kathuria, S. et al. (Jan. 2003, e-published Dec. 2, 2002). "Modulation of anxiety through blockade of anandamide hydrolysis," *Nat Med* 9(1):76-81.
Kaufmann, I. et al. (2009). "Enhanced anandamide plasma levels in patients with complex regional pain syndrome following traumatic injury: a preliminary report," *Eur Surg Res* 43(4):325-329 (2009).
Kotha, S. et al. (2002). "Recent applications of the Suzuki-Miyaura cross-coupling reaction in organic synthesis," *Tetrahedron* 58:9633-9695.
Lambert, D.M. et al. (Mar. 2002). "The palmitoylethanolamide family: a new class of anti-inflammatory agents?" *Curr Med Chem* 9(6):663-674.
Lambert, D.M. et al. (Nov. 2007). "Endocannabinoids and related N-acylethanolamines in the control of appetite and energy metabolism: emergence of new molecular players," *Curr Opin Clin Nutr Metab Care* 10(6):735-744.
Lange, J.H. et al.(Mar. 24, 2005). "Bioisosteric replacements of the pyrazole moiety of rimonabant: synthesis, biological properties, and molecular modeling investigations of thiazoles, triazoles, and imidazoles as potent and selective CB1 cannabinoid receptor antagonists," *J Med Chem* 48(6):1823-1838.
Lever, I. J. et al. (2009). "Localization of the endocannabinoid-degrading enzyme fatty acid amide hydrolase in rat dorsal root ganglion cells and its regulation after peripheral nerve injury," *J Neurosci* 29(12): 3766-3780.
Lima, L.M. et al. (2005). "Bioisosterism: a useful strategy for molecular modification and drug design," *Curr Med Chem* 12(1):23-49.
Loscher, W. et al. (2005). "Blood-brain barrier active efflux transporters: ATP-binding cassette gene family," *NeuroRx* 2(1):86-98.
LoVerme, J. et al. (2005). "The search for the palmitoylethanolamide receptor," *Life Sci* 77(14):1685-1698.
LoVerme, J. et al. (2006). "Rapid broad-spectrum analgesia through activation of peroxisome proliferator-activated receptor-alpha," *J Pharmacol Exp Ther* 319(3):1051-1061.
Mackie, K. (2006). "Cannabinoid receptors as therapeutic targets," *Annu Rev Pharmacol Toxicol* 46:101-122.
McKinney, M. K. et al., Annu Rev Biochem, 74, 411-432 (2005).
Mileni, M. et al., J Mol Biol, 400(4):743-754 (2010).
Mitrirattanakul, S. et al. (2006). "Site-specific increases in peripheral cannabinoid receptors and their endogenous ligands in a model of neuropathic pain," *Pain* 126(1-3): 102-114.
Miyaura, N. et al. (1995). "Palladium-Catalyzed Cross-Coupling Reactions of Organoboron Compounds," *Chem Rev* 95:2457-2483.
Mor, M. et al. 'Cyclohexylcarbamic Acid 3- or 4-Substituted Biphenyl-3-yl Esters as Fatty Acid Amide Hydrolase Inhibitors:Synthesis, Quantitative Structure-Activity Relationships,and Molecular Modeling Studies.' J. Med.Chem. 2004, vol. 47, pp. 4998-5008.
Moreno-Sanz, G. et al. (Oct. 2011, e-published Jul. 7, 2011). "The ABC membrane transporter ABCG2 prevents access of FAAH inhibitor URB937 to the central nervous system," Pharmacol Res 64(4):359-363.
Muccioli, G.G. (Jun. 2010, e-published Mar. 19, 2010). "Endocannabinoid biosynthesis and inactivation, from simple to complex," *Drug Discov Today* 15(11-12):474-483.
Nackley, A.G. et al. (2003). "A peripheral cannabinoid mechanism suppresses spinal fos protein expression and pain behavior in a rat model of inflammation," *Neuroscience* 117(3), 659-670.
Niforatos, Wende et al. "Activation of TRPA1 Channels by the Fatty Acid Amide Hydrolase Inhibitor 3-Carbamoylbiphenyl-3-yl cyclohexylcarbamate (URB597)," Mol. Pharmacol. 2007, vol. 71, pp. 1209-1216.
Ortega-Gutierrez, S. et al. (2004). *Biochemistry*, 43:8184-8190.
Patricelli, M.P. et al. (1999). "Chemical and mutagenic investigations of fatty acid amide hydrolase: evidence for a family of serine hydrolases with distinct catalytic properties," *Biochemistry*, 38:9804-9812.
Patricelli, M. P. et al. (1999). *Biochemistry* 38:14125-14130.
Patricelli, M.P. et al. (2001). "Proteins regulating the biosynthesis and inactivation of neuromodulatory fatty acid amides," *Vitam Horm* 62:95-131.
Piatnitski, E.L. et al. (Nov. 1, 2005). "Arylphthalazines: identification of a new phthalazine chemotype as inhibitors of VEGFR kinase," *Bioorg Med Chem Lett* 15(21):4696-4698.
Piomelli, D. et al. (May 1999). *Proc Natl Acad Sci USA* 96:5802-5807.
Piomelli, D., et al. (Jun. 2000). "The endocannabinoid system as a target for therapeutic drugs," *Trends Pharmacol. Sci.* 21(6):218-224.
Piomelli, D. et al. (Jul. 2005). "The endocannabinoid system: a drug discovery perspective," *Curr Opin Investig Drugs* 6(7):672-679.
Piomelli, D. et al. (2006). Pharmacological profile of the selective FAAH inhibitor KDS-4103 (URB597). *CNS Drug Rev* 12(1):21-38.
Piomelli, D. (Jul. 2013, e-published Apr. 6, 2013). "A fatty gut feeling," *Trends Endocrinol Metab* 24(7):332-341.
PubChem. Compound Summary for: CID 11773226. Create Date: Oct. 27, 2006. [last accessed Dec. 28, 2016]. located at <https://pubchem.ncbi.nlm.nih.gov/summary/summary.cgi?cid=11773226>, 13 pages.
PubChem. Compound Summary for: CID 71506770. Create Date: Jun. 10, 2013. [last accessed Dec. 28, 2016]. located at <https://pubchem.ncbi.nlm.nih.gov/compund/71506770>, 13 pages.
PubChem Compound ID 5514389 [http://pubchem.ncbi.nlm.nih.gov/summary/summary.cgi?q=all&cid=5514389] Retrieved from the Internet on Aug. 20, 2014, 13 pages.
PubChem. Substance Record for SID 174502363. Available Date: Apr. 3, 2014. [last accessed on Dec. 28, 2016]. located at <https://pubchem.ncbi.nlm.nih.gov/substance/174502363>, 7 pages.
Puig, S. et al. (1996). "Formalin-evoked activity in identified primary afferent fibers: systemic lidocaine suppresses phase-2 activity," *Pain* 64(2): 345-355.
Richardson, J.D. et al. (1998). "Cannabinoids reduce hyperalgesia and inflammation via interaction with peripheral CB1 receptors," *Pain* 75(1):111-119.
Richardson, D. et al. (2008, e-published Apr. 16, 2008). "Characterisation of the cannabinoid receptor system in synovial tissue and fluid in patients with osteoarthritis and rheumatoid arthritis," *Arthritis Res Ther* 10(2):R43.
Russo, R. et al., The fatty acid amide hydrolase inhibitor URB597(cyclohexylcarbamic acid 3'-carbamoylbiphenyl-3-ylester) reduces neuropathic pain after oral administration in mice. J Pharmacol Exp Ther 322(1):236-242 (2007).
Sagar, D.R. et al. (2008). "Inhibition of fatty acid amide hydrolase produces PPAR-alpha-mediated analgesia in a rat model of inflammatory pain," *Br J Pharmacol* 155(8): 1297-1306.
Scherma, M. (2012). Br J Pharmacol 165:2539-2548.
Schlosburg, J.E. et al. (2009). "Targeting fatty acid amide hydrolase (FAAH) to treat pain and inflammation," *AAPS J* 11(1):39-44.

(56) References Cited

OTHER PUBLICATIONS

Schwartz, G.J. et al. (Oct. 2008). "The lipid messenger OEA links dietary fat intake to satiety," *Cell Metab* 8(4):281-288.
Seierstad, M. et al. (Dec. 11, 2008). *J Med Chem*, 51(23):7327-7343.
Starowicz, K. et al. (2007). "Biochemistry and pharmacology of endovanilloids," *Pharmacol Ther* 114(1):13-33.
Stein, C. et al. (2003). "Attacking pain at its source: new perspectives on opioids," *Nat Med* 9(8):1003-1008.
Stein, C. et al. (2009). "Opioids and sensory nerves," *Handb Exp Pharmacol* (194):495-518.
Suzuki, A. (Jul. 18, 2011, e-published May 25, 2011). "Cross-coupling reactions of organoboranes: an easy way to construct C—C bonds (Nobel Lecture)," *Angew Chem Int Ed Engl* 50(30):6722-6737.
Tarzia, G. et al. (Jan. 2006). "Synthesis and structure-activity relationships of FAAH inhibitors: cyclohexylcarbamic acid biphenyl esters with chemical modulation at the proximal phenyl ring," ChemMedChem 1(1):130-139.
Tegeder, I. et al. (2003). "Peripheral opioid analgesia in experimental human pain models," *Brain* 126(Pt 5):1092-1102.
Ueda, N. et al. (Oct. 2010, e-published Feb. 10, 2010). "N-acylethanolamine metabolism with special reference to N-acylethanolamine-hydrolyzing acid amidase (NAAA)," Prog Lipid Res 49(4):299-315.
Vacondio, F. et al. (Sep. 2009). "Structure-property relationships of a class of carbamate-based fatty acid amide hydrolase (FAAH) inhibitors: chemical and biological stability," *ChemMedChem* 4(9):1495-1504.
Wei, B. Q. et al. (2006). J Biol Chem, 281(48): 36569-36578.
Wendeler, M. et al. (Jul. 7, 2003). "Inhibitors of endocannabinoid degradation: potential therapeutics for neurological disorders," *Angew. Chem. Int. Ed.* 42(26):2938-2941.
Written Opinion dated Apr. 6, 2012, for PCT Application No. PCT/US2011/045114, filed on Jul. 22, 2011, 6 pages.
Written Opinion dated Feb. 18, 2013, for PCT Application No. PCT/US2012/051478, filed Aug. 17, 2012, 6 pages.
Written Opinion dated Aug. 25, 2015, for PCT Application No. PCT/US2015/024753, filed Apr. 7, 2015, 5 pages.
U.S. Appl. No. 60/336,289, filed Oct. 31, 2001.
U.S. Appl. No. 61/492,293, filed Jun. 1, 2011.
U.S. Appl. No. 61/368,500, filed Jul. 28, 2010.

* cited by examiner

INHIBITORS OF FATTY ACID AMIDE HYDROLASE (FAAH) ENZYME WITH IMPROVED ORAL BIOAVAILABILITY AND THEIR USE AS MEDICAMENTS

CROSS-REFERENCES TO RELATED APPLICATIONS

This application is a continuation of International Patent Application No. PCT/US2015/024753, filed Apr. 7, 2015, which claims the benefit of U.S. Provisional Patent Application No. 61/976,439 filed on Apr. 7, 2014, all of which are incorporated herein by reference in their entirety and for all purposes.

STATEMENT AS TO RIGHTS TO INVENTIONS MADE UNDER FEDERALLY SPONSORED RESEARCH AND DEVELOPMENT

This invention was made with government support under grant no. DA031387, awarded by the National Institutes of Health. The Government has certain rights in the invention.

FIELD OF THE INVENTION

Described herein are certain O-arylcarbamate inhibitors of the fatty acid amide hydrolase (FAAH) enzyme that showed, unexpectedly, an improved oral bioavailability, their methods of preparation, their formulations as medicaments, and their therapeutic application for the treatment of pathologies, conditions and disorders which would clinically benefit from inhibition of the activity of the fatty acid amide hydrolase (FAAH) enzyme.

BACKGROUND

The ethanolamides of long-chain fatty acids, or fatty acid ethanolamides (FAEs), are a class of bioactive lipids that serve important signaling function in both plants and animals (Piomelli, D. *Trends Endocr Metab* 2013; 24: 332-341). Polyunsaturated FAEs such as arachidonoylethanolamide (anandamide) are endogenous agonists (endocannabinoids) for type 1 and type 2 cannabinoid receptors, $CB_1$ and $CB_2$, and participate in the control of stress-coping responses and pain initiation (Calignano, A. et al., *Nature* 1998; 394: 277-281). On the other hand, monounsaturated and saturated FAEs, such as oleoylethanolamide (OEA) and palmitoylethanolamide (PEA), regulate energy balance, pain and inflammation primarily by engaging peroxisome proliferator-activated receptor-α (PPAR-α), a member of the nuclear receptor superfamily (Fu, J. et al., *Nature* 2003; 425: 90-93; Schwartz, G. J. et al., *Cell Metab* 2008; 8(4): 281-288; LoVerme, J. et al., *J Pharm Exp Ther* 2006; 19(3):1051-1061).

Since the discovery that $\Delta^9$-tetrahydrocannabinol (THC), the primary bioactive constituent of the *cannabis* plant, interacts with $CB_1$ and $CB_2$ receptors, several synthetic cannabinoid receptor agonists have been prepared. Some $CB_1$ agonists, deriving from chemical modification of THC, have been approved for the treatment of different pathological conditions, such as anorexia nervosa (Marinol), refractory chemotherapy-induced nausea and vomiting (Nabilone), neuropathic pain induced by multiple sclerosis, and adjunctive treatment of advanced cancer pain (Sativex).

The therapeutic potential of direct-acting cannabinoid agonists is limited by an undesirable profile of side effects, which includes dysphoria, dizziness, and effects on motor coordination and memory. An alternative strategy to achieve the desired modulation of cannabinoid receptor activity, without exposing patients to the risk of serious side effects, consists in increasing endocannabinoid levels (Cravatt, B. F., Lichtman, A. H. *Curr Opin Chem Biol* 2003; 7:469-475; Piomelli, D. *Curr Opin Investig Drugs* 2005; 6:672-679).

Endocannabinoids and other fatty acid ethanolamides are not stored in the cell, but are produced on demand, and their levels are regulated by enzymes responsible for their synthesis and degradation (Piomelli, D. *Trends Endocr Metab* 2013; 24: 332-341; Di Marzo, V., et al. *Curr Opin Lipidol* 2007; 18(2): 129-140; (Ueda, N., et al. *Prog Lipid Res* 2010; 49(4): 299-315). In particular, anandamide is inactivated via a two-step process consisting of high-affinity transport into cells (Di Marzo, V. et al. *Nature* 1994; 372: 686-691; Beltramo, M. et al. *Science* 1997; 277: 1094-1097) followed by intracellular degradation catalysed by fatty acid amide hydrolase (McKinney, M. K. and Cravatt, B. F. *Annu Rev Biochem* 2005; 74: 411-432), thus releasing arachidonic acid and ethanolamine.

Fatty acid amide hydrolase (FAAH) is a membrane-bound serine hydrolase that belongs to the amidase signature family of hydrolases. The active site of FAAH is characterized by an atypical catalytic triad consisting in Ser241-Ser217-Lys142, which is capable of hydrolysing amide and ester bonds at similar rates (Ahn, K., et al. *Chem Rev* 2008; 108(5): 1687-1707; McKinney, M. K., et al. *Annual Rev Biochem* 2005; 74: 411-432). FAAH can catalyse the hydrolysis of the amide bond of PEA and OEA (Muccioli, G. G. *Drug Discovery Today* 2010; 15(11-12): 474-483; Boger, D. L., et al. *Curr Pharm Des* 1998; 4(4): 303-314), and regulates the endogenous levels of other classes of amide-derived lipids, such as the N-acyl taurines (NATs), which activate transient receptor potential (TRP) (Saghatelian, A., et al. *Biochemistry-U* 2006; 45(30): 9007-9015) ions channels, and fatty acid primary amides (FAPAs) (Fowler, C. J., et al. *Br J Pharmacol* 2004; 141(2): 195-196), like the sleep-inducing lipid oleamide. A second isoform of FAAH, named FAAH-2 was isolated from the human ovarian cancer cell line OVCAR-3 and the breast cancer cell line MCF-7. This second isoform shares 20% homology with FAAH and shows a higher affinity for oleamide than anandamide (Wei, B. Q., et al. *J Biol Chem* 2006; 281(48): 36569-36578). FAAH-2 also differs from FAAH-1 for the intracellular localization, as it is found in the lipid droplets and not in the membrane of the endoplasmic reticulum.

Several disease conditions are characterized by alterations in the endogenous levels of the biomolecules hydrolysed by FAAH. Therefore, this enzyme has been considered a target for modulating endocannabinoid and other fatty acid ethanolamide levels in vivo (Hansen, H. S., et al. *Exp Neurol* 2010; 224(1): 48-55). Substantial efforts have been directed to the discovery of potent and selective FAAH inhibitors, aiming at the development of new therapeutic approaches for the treatment of several pathologic conditions, including pain, inflammation, appetite regulation, anxiety, and depression (Piomelli, D. *Curr Opin Investig Drugs* 2005; 6: 672-679; Lambert, D. M., et al. *Curr Opin Clin Nutr Metab Care* 2007; 10(6): 735-744; Di Marzo, V. et al. *Nat Rev Drug Discov* 2008; 7(5): 438-455).

FAAH inhibitors having improved adsorption and/or oral bioavailability (F %) are of particular therapeutic interest in order to decrease the daily dose administered while maintaining therapeutic afficacy and improving patient's compliance. Provided herein, inter alia, are solutions to these and other problems in the art.

SUMMARY OF THE INVENTION

In an aspect is provided a compound having the formula:

(I)

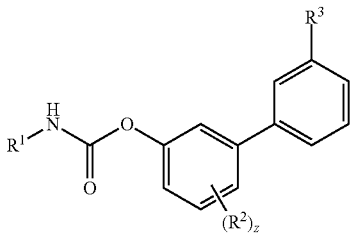

or a pharmaceutically acceptable salt thereof. $R^1$ is substituted or unsubstituted cycloalkyl, substituted or unsubstituted heterocycloalkyl, substituted or unsubstituted aryl, or substituted or unsubstituted heteroaryl. $R^2$ is independently halogen, $—CX_3$, $—OCX_3$, $—OCHX_2$, substituted or unsubstituted $C_1$-$C_8$ alkyl, or substituted or unsubstituted 2 to 8 membered heteroalkyl. $R^3$ is $—SO_2R^6$, $—SO_2NR^4R^5$, or $—C(O)NR^4R^5$. $R^4$, $R^5$, and $R^6$ are independently hydrogen, substituted or unsubstituted $C_1$-$C_8$ alkyl or substituted or unsubstituted 2 to 8 membered heteroalkyl. $R^4$ and $R^5$ bonded to the same nitrogen atom, may optionally be joined to form a substituted or unsubstituted 4 to 8 membered heterocycloalkyl or substituted or unsubstituted 5 to 6 membered heteroaryl, The symbol z is an integer from 1 to 4. The symbol X is —F, —Cl, —Br, or —I.

In another aspect is provided a compound of Formula (I)

(I)

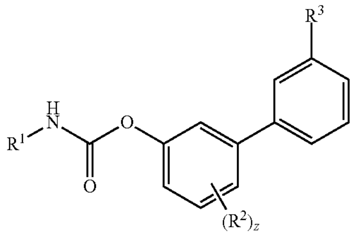

wherein $R^1$ is a cycloalkyl group; $R^3$ is $SO_2NR^4R^5$, $CONR^4R^5$, or $SO_2R^6$, where $R^4$ and $R^5$ can be, independently, hydrogen, alkyl or $R^4$ and $R^5$ together with the N atom to which they are connected may form a 4- to 6-membered ring, and $R^6$ is an alkyl group; z is an integer selected from 1 or 2; $R^2$ is F or $OCHF_2$, and can be attached to any position of the ring with the proviso that when $R^1$ is cyclohexyl, $R^3$ is $CONH_2$, z is 1 and $R^2$ is F, then $R^2$ is not attached in position para to the carbamate.

In another aspect is provided a pharmaceutical composition including a compound described herein (including embodiments thereof).

In another aspect is provided a method for modulating the level of a fatty acid ethanolamide (FAE) in a subject including administering an effective amount of a composition described herein (e.g., compound described herein (e.g., including embodiments thereof) or a pharmaceutical composition described herein).

In an aspect is provided a method of reducing tobacco use by a subject, the method including administering an effective amount of a composition as described herein (including in an aspect, embodiment, table, figure, claim, sequence listing, or example) (e.g., a compound described herein or a pharmaceutical composition described herein).

In an aspect is provided a method of treating or preventing a disease in a subject in need of the treatment, the method including administering an effective amount of a composition as described herein (including in an aspect, embodiment, table, figure, claim, sequence listing, or example) (e.g., a compound described herein or a pharmaceutical composition described herein), wherein the disease is reduced appetite, gastric damage, enteric damage, a nicotine use disorder, tobacco smoking, substance abuse, a *cannabis* use disorder, a cocaine use disorder, an opioid use disorder, an amphetamine use disorder, a methamphetamine use disorder, an alcohol use disorder, an eating disorder, anxiety, post-traumatic stress disorder, schizophrenia, a mood disorder, pain, inflammation, or ocular glaucoma.

In an aspect is provided a method of preventing or treating pathological behaviour in a subject, the method including administering an effective amount of a composition as described herein (including in an aspect, embodiment, table, figure, claim, sequence listing, or example) (e.g., a compound described herein or a pharmaceutical composition described herein).

In another aspect is provided a method for preparing a compound described herein (including embodiments thereof).

DETAILED DESCRIPTION OF THE INVENTION

Disclosed herein, inter alia, is a specific selection of compounds bearing a fluorine atom or a difluoromethoxy group attached to the aromatic ring proximal to the carbamate functionality of biphenyl carbamate FAAH inhibitors having unexpected improvements in solubility and absorption from the gastro-intestinal tract, thus resulting in an improved oral bioavailability over corresponding non-fluorinated compounds. Such advantage is a key factor for compounds that are meant to enter the systemic circulation in order to reach a variety of organs in the body, including the CNS, where the inhibition of FAAH will be clinically beneficial.

In addition, the possibility to utilize the oral route to administer a drug represents by far for the patients the best compliant form of administration, particularly in the elderly population, as this treatment avoids the need of intravenous administration, either at home or in hospital, in order to achieve the range of drug concentration necessary to treat the disease.

DEFINITIONS

The definitions and embodiments described in this section are applicable only to the embodiments and descriptions contained within this section. All other sections or portions of this patent application other than this section use the definitions, terms, descriptions, and embodiments, contained outside of this section.

The abbreviations used herein have their conventional meaning within the chemical and biological arts, unless otherwise defined. The chemical structures and formulae set forth herein are constructed according to the standard rules of chemical valency known in the chemical arts. The following terms, used in the specification and claims of this application, have the meaning specified hereunder, unless otherwise defined.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a non-cyclic straight (i.e., unbranched) or branched carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). In embodiments, the term "alkyl", as used herein, indicates a saturated aliphatic hydrocarbon radical, including straight chain and branched chain radicals of 1 to 6 carbon atoms.

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a non-cyclic stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—CH 2, —S(O)—$CH_3$, —$CH_2$—$CH_2$—$S(O)_2$—$CH_3$, —CH═CH—O—$CH_3$, —$Si(CH_3)_3$, —$CH_2$—CH═N—$OCH_3$, —CH═CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—$Si(CH_3)_3$.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$C(O)_2R'$— represents both —$C(O)_2R'$— and —$R'C(O)_2$—. As described above, heteroalkyl groups, as used herein, include those groups that are attached to the remainder of the molecule through a heteroatom, such as —C(O)R', —C(O)NR', —NR'R", —OR', —SR', and/or —$SO_2R'$. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. In embodiments, the term "cycloalkyl", as used herein, indicates a saturated 3- to 7-membered all-carbon monocyclic ring.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene.

The term "oxo," as used herein, means an oxygen that is double bonded to a carbon atom.

The term "alkylsulfonyl," as used herein, means a moiety having the formula $-S(O_2)-R'$, where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R"', —OC(O)R', —C(O)R', $-CO_2R'$, —CONR'R", —OC(O)NR'R", —NR"C(O)R', —NR'—C(O)NR"R"', $-NR''C(O)_2R'$, —NR—C(NR'R"R"')=NR"", —NR—C(NR'R")=NR"'—S(O)R'—$S(O)_2R'$, $-S(O)_2NR'R''$, $-NRSO_2R'$, —NR'NR"R"', —ONR'R", —NR'C=(O)NR"NR"'R"", —CN, $-NO_2$, in a number ranging from zero to (2m'+1), where m' is the total number of carbon atoms in such radical. R, R', R", R"', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R"', and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., $-CF_3$ and $-CH_2CF_3$) and acyl (e.g., $-C(O)CH_3$, $-C(O)CF_3$, $-C(O)CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R"', —OC(O)R', —C(O)R', $-CO_2R'$, —CONR'R", —OC(O)NR'R", —NR"C(O)R', —NR'—C(O)NR"R"', $-NR''C(O)_2R'$, —NR—C(NR'R"R"')=NR"", —NR—C(NR'R")=NR"', —S(O)R', $-S(O)_2R'$, $-S(O)_2NR'R''$, $-NRSO_2R'$, —NR'NR"R"', —ONR'R", —NR'C=(O)NR"NR"'R"", —CN, $-NO_2$, —R', $-N_3$, $-CH(Ph)_2$, fluoro($C_1$-$C_4$)alkoxy, and fluoro($C_1$-$C_4$)alkyl, in a number ranging from zero to the total number of open valences on the aromatic ring system; and where R', R", R"', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R"', and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula $-T-C(O)-(CRR')_q-U-$, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula $-A-(CH_2)_r-B-$, wherein A and B are independently —CRR'—, —O—, —NR—, —S—, —S(O)—, $-S(O)_2-$, $-S(O)_2NR'-$, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula $-(CRR)_s-X'-(C''R''R''')_d-$, where s and d are independently integers of from 0 to 3, and X' is —O—, —S—, —S(O)—, —$S(O)_2$—, or —$S(O)_2NR'$—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, —$OCF_3$, —$OCHF_2$, —$NHSO_2CH_3$, —$N_3$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:

(i) oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC═(O)$NHNH_2$, —NHC═(O) $NH_2$—$NHSO_2H$, —NHC═(O)H, —NHC(O)—OH, —NHOH, —$OCF_3$, —$OCHF_2$, —$NHSO_2CH_3$, —$N_3$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, substituted with at least one substituent selected from:

(a) oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC═(O)$NHNH_2$, —NHC═(O) $NH_2$, —$NHSO_2H$, —NHC═(O)H, —NHC(O)—OH, —NHOH, —$OCF_3$, —$OCHF_2$, —$NHSO_2CH_3$, —$N_3$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, heteroaryl, substituted with at least one substituent selected from: oxo, halogen, —$CF_3$, —CN, —OH, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)—OH, —NHOH, —$OCF_3$, —$OCHF_2$, —$NHSO_2CH_3$, —$N_3$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Described herein are active metabolites of compounds described herein, for example but without limitation, those displaying a hydroxyl group (e.g., attached to the cycloalkyl ring R or to an aromatic ring of the biphenyl system).

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Described herein are solvates of the compounds described herein. The compounds described herein may be isolated in association with solvent molecules by crystallization or evaporation of an appropriate solvent to give the corresponding solvates. The compounds described herein may be in crystalline form. In embodiments, the crystalline forms of the compounds described herein are polymorphs.

As used herein, the term "salt" refers to acid or base salts of the compounds described herein.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

Compounds described herein may contain one or more chiral centres. Compounds containing one chiral centre can occur as single enantiomer or mixtures of the two enantiomers. Such mixtures occur as racemates or racemic mixtures. Compounds containing more than one chiral centre can occur as single enantiomer and pairs of enantiomers, and as stereoisomers which are not enantiomers, referred to as diastereoisomers. A compound described herein may be any possible stereoisomer or mixture of stereoisomers thereof.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$) or carbon-14 ($^{14}C$). All isotopic variations of the compounds of the present invention, whether radioactive or not, are encompassed within the scope of the present invention. Examples of isotopes that can be incorporated into compounds described herein include isotopes of hydrogen, carbon, nitrogen, oxygen, sulphur, fluorine, such as $^{2}H$, $^{3}H$, $^{11}C$, $^{13}C$, $^{14}C$, $^{15}N$ $^{17}O$, $^{18}O$, $^{35}S$, or $^{18}F$.

Compounds described herein that contain the aforementioned isotopes and/or other isotopes of other atoms are within the scope of the present invention. Isotopically-labelled compounds of the present invention, for example those into which radioactive isotopes such as $^{3}H$, $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. $^{11}C$ and $^{18}F$ isotopes are particularly useful in PET (positron emission tomography) and SPECT (single photon emission computerized tomography), all useful in brain imaging. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances (see, for instance, Shao, L., Hewitt, M C. *The kinetic isotope effect in the search for deuterated drugs. Drug News Perspect* 2010; 23(6): 398-404, which is herein incorporated by reference). Isotopically labelled compounds described herein may be prepared by carrying out the procedures disclosed herein (e.g., in the Schemes and/or in the Examples) by substituting a readily available isotopically labelled reagent for a non-isotopically labelled reagent.

The symbol "∿∿" denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, the compounds and methods described herein may be useful in the treatment of smoking tobacco (e.g., cessation or reduction); tobacco use (e.g., cessation or reduction); a nicotine use disorder (e.g., nicotine craving, nicotine addiction, nicotine dependence, or nicotine withdrawal) or a symptom thereof; substance abuse or a symptom thereof; a *cannabis* use disorder (e.g., *cannabis* craving, *cannabis* addiction, *cannabis* dependence, or *cannabis* withdrawal) or a symptom thereof; a cocaine use disorder (e.g., cocaine craving, cocaine addiction, cocaine dependence, or cocaine withdrawal) or a symptom thereof; an opioid use disorder (e.g., opioid craving, opioid addiction, opioid dependence, or opioid withdrawal) or a symptom thereof; an opiate use disorder (e.g., opiate craving, opiate addiction, opiate dependence, or opiate withdrawal) or a symptom thereof; an amphetamine use disorder (e.g., amphetamine craving, amphetamine addiction, amphetamine dependence, or amphetamine withdrawal) or a symptom thereof; a methamphetamine use disorder (e.g., methamphetamine craving, methamphetamine addiction, methamphetamine dependence, or methamphetamine withdrawal) or a symptom thereof; or an alcohol use disorder (e.g., alcohol craving, alcohol addiction, alcohol dependence, alcohol withdrawal, or alcohol induced delirium) or a symptom thereof; an eating disorder (e.g., bulimia nervosa, anorexia nervosa, a binge eating disorder, or an eating disorder not otherwise specified (EDNOS)) or a symptom thereof; anxiety or a symptom thereof, post-traumatic stress disorder or a symptom thereof; schizophrenia or a symptom thereof; a mood disorder (e.g., bipolar disorder type I, bipolar disorder type II, cyclothymia, substance-induced mood disorder, depression, atypical depression, psychotic major depression, post-partum depression, dysthymia, catatonic depression, melancholic depression, or a depressive disorder not otherwise specified (DDNOS)) or a symptom thereof; pain (e.g., nociceptive pain, neuropathic pain, inflammatory pain, non-inflammatory pain, or pain associated with a chronic condition) or a symptom thereof; or ocular glaucoma or a symptom thereof; or for modulating (e.g., increasing) appetite, or for treating inflammation or a symptom thereof.

An "effective amount" is an amount sufficient to accomplish a stated purpose (e.g. achieve the effect for which it is administered, treat a disease, reduce enzyme activity, increase enzyme activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist (inhibitor) required to decrease the activity of an enzyme or protein relative to the absence of the antagonist. An "activity increasing amount," as used herein, refers to an amount of agonist (activator) required to increase the activity of an enzyme or protein relative to the absence of the agonist. A "function disrupting amount," as used herein, refers to the amount of antagonist (inhibitor) required to disrupt the function of an enzyme or protein relative to the absence of the antagonist. A "function increasing amount," as used herein, refers to the amount of agonist (activator) required to increase the function of an enzyme or protein relative to the absence of the agonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme.

As defined herein, the term "inhibition", "inhibit", "inhibiting" and the like in reference to a protein-inhibitor (e.g. antagonist) interaction means negatively affecting (e.g. decreasing) the activity or function of the protein relative to the activity or function of the protein in the absence of the inhibitor. In some embodiments inhibition refers to reduction of a disease or symptoms of disease. Thus, inhibition includes, at least in part, partially or totally blocking stimulation, decreasing, preventing, or delaying activation, or inactivating, desensitizing, or down-regulating signal transduction or enzymatic activity or the amount of a protein.

The term "modulator" refers to a composition that increases or decreases the level of a target molecule or the function of a target molecule.

"Patient" or "subject in need thereof" refers to a living organism suffering from or prone to a disease or condition that can be treated by administration of a compound or pharmaceutical composition, as provided herein. Non-limiting examples include humans, other mammals, bovines, rats, mice, dogs, monkeys, goat, sheep, cows, deer, and other non-mammalian animals. In some embodiments, a patient is human.

"Disease" or "condition" refer to a state of being or health status of a patient or subject capable of being treated with a compound, pharmaceutical composition, or method provided herein.

Examples of diseases, disorders, or conditions include, but are not limited to smoking tobacco; tobacco use; a nicotine use disorder (e.g., nicotine craving, nicotine addiction, nicotine dependence, or nicotine withdrawal); substance abuse; a *cannabis* use disorder (e.g., *cannabis* craving, *cannabis* addiction, *cannabis* dependence, or *cannabis* withdrawal); a cocaine use disorder (e.g., cocaine craving, cocaine addiction, cocaine dependence, or cocaine withdrawal); an opioid use disorder (e.g., opioid craving, opioid addiction, opioid dependence, or opioid withdrawal); an opiate use disorder (e.g., opiate craving, opiate addiction, opiate dependence, or opiate withdrawal); an amphetamine use disorder (e.g., amphetamine craving, amphetamine addiction, amphetamine dependence, or amphetamine withdrawal); a methamphetamine use disorder (e.g., methamphetamine craving, methamphetamine addiction, methamphetamine dependence, or methamphetamine withdrawal); or an alcohol use disorder (e.g., alcohol craving, alcohol addiction, alcohol dependence, alcohol withdrawal, or alcohol induced delirium); an eating disorder (e.g., bulimia nervosa, anorexia nervosa, a binge eating disorder, or an eating disorder not otherwise specified (EDNOS)); anxiety or a symptom thereof, post-traumatic stress disorder; schizophrenia; a mood disorder (e.g., bipolar disorder type I, bipolar disorder type II, cyclothymia, substance-induced mood disorder, depression, atypical depression, psychotic major depression, post-partum depression, dysthymia, catatonic depression, melancholic depression, or a depressive disorder not otherwise specified (DDNOS)); pain (e.g., nociceptive pain, neuropathic pain, inflammatory pain, non-inflammatory pain, or pain associated with a chronic condition); inflammation; or ocular glaucoma; or reduced appetite.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

A pharmaceutical composition may include another active ingredient. The term "carrier" refers to a vehicle, excipient, diluent, or adjuvant with which the therapeutic or active ingredient is administered. Any carrier and/or excipient suitable for the form of preparation desired for administration is contemplated for use with the compounds described herein. The carrier may take a wide variety of forms depending on the form of preparation desired for administration, e.g. oral or parenteral (including intravenous). In preparing the compositions for oral dosage form, any of the pharmaceutical media commonly used in the art for oral dosage forms may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents, and the like in the case of oral solid preparations such as, for example, powders, hard and soft capsules and tablets, with the solid oral preparations being preferred over the liquid preparations.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies. The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym.* Ed. 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles.

Pharmaceutical compositions provided by the present invention include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule, and/or reducing, eliminating, or slowing the progression of disease symptoms. Determination of a therapeutically effective amount of a compound of the invention is well within the capabilities of those skilled in the art, especially in light of the detailed disclosure herein.

If desired, tablets may be coated by standard aqueous or non-aqueous techniques. In embodiments, such compositions and preparations can include at least 0.1 percent of active compound. The percentage of active compound in these compositions may be varied and may conveniently be between about 1 percent to about 60 percent of the weight of the unit. The amount of active compound in such therapeutically useful compositions is such that therapeutically active dosage will be obtained. The active compounds can also be administered intranasally as, for example, liquid drops or spray.

The tablets, pills, capsules, and the like may include a binder such as gum tragacanth, acacia, corn starch or gelatin; excipients such as dicalcium phosphate; a disintegrating agent such as corn starch, potato starch, alginic acid; a lubricant such as magnesium stearate; or a sweetening agent such as sucrose, lactose or saccharin. When a dosage unit form is a capsule, it may include, in addition to materials of the above type, a liquid carrier such as a fatty oil. Various other materials may be included as coatings or to modify the physical form of the dosage unit. For instance, tablets may be coated with shellac, sugar or both. A syrup or elixir may contain, in addition to the active ingredient, sucrose as a sweetening agent, methyl or propylparabens as preservatives, a dye; or a flavoring agent such as cherry or orange flavor. To prevent breakdown during transit through the upper portion of the gastrointestinal tract, the composition may be an enteric coated formulation.

Compositions for topical administration include, but are not limited to, ointments, creams, lotions, solutions, pastes, gels, sticks, liposomes, nanoparticles, patches, bandages and wound dressings. In certain embodiments, the topical formulation comprises a penetration enhancer.

Compositions for pulmonary administration include, but are not limited to, dry powder compositions including the powder of a compound of Formula I (including embodiments thereof) or a salt thereof, and the powder of a suitable carrier and/or lubricant. The compositions for pulmonary administration can be inhaled from any suitable dry powder inhaler device known to a person skilled in the art.

Administration of the compositions may be performed under a protocol and at a dosage sufficient to reduce inflammation and/or pain in a subject. In some embodiments, in the pharmaceutical compositions of the present invention the active principle or active principles are generally formulated in dosage units. The dosage unit may contain from 0.1 to 1000 mg of a compound of Formula I (including embodiments thereof) per dosage unit for daily administration.

In some embodiments, the amount effective for topical formulation will depend on the severity of the disease, disorder or condition, previous therapy, the individual's health status and response to the drug. In some embodiments, the dose is in the range from 0.001% by weight to about 60% by weight of the formulation.

When used in combination with one or more other active ingredients, a compound described herein (e.g., Formula I, including embodiments) and the other active ingredient may be used in lower doses than when each is used singly.

With respect to formulations with respect to any variety of routes of administration, methods and formulations for the administration of drugs are disclosed in *Remington's Pharmaceutical Sciences,* $17^{th}$ *Edition*, Gennaro et al. Eds., Mack Publishing Co., 1985, and *Remington's Pharmaceutical Sciences*, Gennaro A R ed. $20^{th}$ *Edition,* 2000, Williams & Wilkins PA, USA, and *Remington: The Science and Practice of Pharmacy,* $21^{st}$ *Edition*, Lippincott Williams & Wilkins Eds., 2005; and in *Ansel's Pharmaceutical Dosage Forms and Drug Delivery Systems,* $8^{th}$ *Edition*, Lippincott Williams & Wilkins Eds., 2005, which are herein incorporated by reference.

Compounds

In an aspect is provided a compound having the formula:

(I)

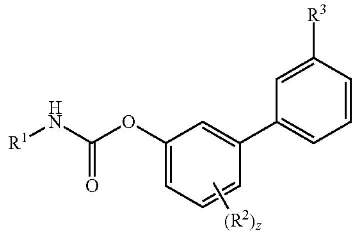

or a pharmaceutically acceptable salt thereof. $R^1$ is substituted or unsubstituted cycloalkyl, substituted or unsubstituted heterocycloalkyl, substituted or unsubstituted aryl, or substituted or unsubstituted heteroaryl. $R^2$ is independently halogen, —$CX_3$, —$OCX_3$, —$OCHX_2$, substituted or unsubstituted $C_1$-$C_8$ alkyl, or substituted or unsubstituted 2 to 8 membered heteroalkyl. $R^3$ is —$SO_2R^6$, —$SO_2NR^4R^5$, or —$C(O)NR^4R^5$. $R^4$, $R^5$, and $R^6$ are independently hydrogen, substituted or unsubstituted $C_1$-$C_8$ alkyl or substituted or unsubstituted 2 to 8 membered heteroalkyl. $R^4$ and $R^5$ may optionally be joined to form a substituted or unsubstituted 4 to 8 membered heterocycloalkyl or substituted or unsubstituted 5 to 6 membered heteroaryl, The symbol z is an integer from 1 to 4. The symbol X is —F, —Cl, —Br, or —I.

The compound may have the formula

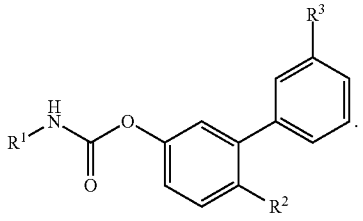

The compound may have the formula

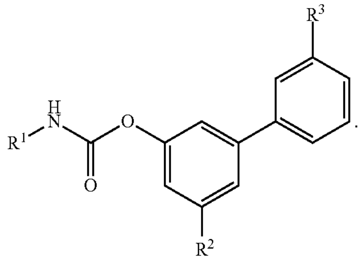

The compound may have the formula

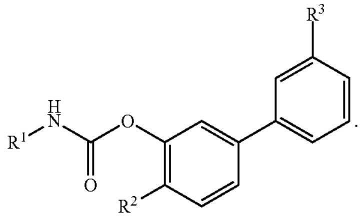

The compound may have the formula

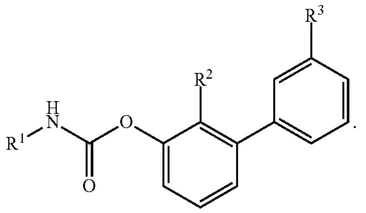

$R^1$ may be substituted or unsubstituted cycloalkyl. $R^1$ may be substituted or unsubstituted heterocycloalkyl. $R^1$ may be substituted or unsubstituted aryl. $R^1$ may be substituted or unsubstituted heteroaryl. $R^1$ may be substituted cycloalkyl. $R^1$ may be substituted heterocycloalkyl. $R^1$ may be substituted aryl. $R^1$ may be substituted heteroaryl. $R^1$ may be unsubstituted cycloalkyl. $R^1$ may be unsubstituted heterocycloalkyl. $R^1$ may be unsubstituted aryl. $R^1$ may be unsubstituted heteroaryl.

$R^1$ may be substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. $R^1$ may be substituted $C_3$-$C_8$ cycloalkyl. $R^1$ may be substituted 3 to 8 membered heterocycloalkyl. $R^1$ may be substituted $C_6$-$C_{10}$ aryl. $R^1$ may be substituted 5 to 10 membered heteroaryl. $R^1$ may be unsubstituted $C_3$-$C_8$ cycloalkyl. $R^1$ may be unsubstituted 3 to 8 membered heterocycloalkyl. $R^1$ may be unsubstituted $C_6$-$C_{10}$ aryl. $R^1$ may be unsubstituted 5 to 10 membered heteroaryl.

$R^1$ may be substituted or unsubstituted $C_4$-$C_6$ cycloalkyl, substituted or unsubstituted 4 to 6 membered heterocycloalkyl, substituted or unsubstituted phenyl, or substituted or unsubstituted 5 to 6 membered heteroaryl. $R^1$ may be substituted $C_4$-$C_6$ cycloalkyl. $R^1$ may be substituted 4 to 6 membered heterocycloalkyl. $R^1$ may be substituted phenyl. $R^1$ may be substituted 5 to 6 membered heteroaryl. $R^1$ may be unsubstituted $C_4$-$C_6$ cycloalkyl. $R^1$ may be unsubstituted 4 to 6 membered heterocycloalkyl. $R^1$ may be unsubstituted phenyl. $R^1$ may be unsubstituted 5 to 6 membered heteroaryl.

$R^1$ may be substituted or unsubstituted $C_5$-$C_6$ cycloalkyl, substituted or unsubstituted 5 to 6 membered heterocycloalkyl, substituted or unsubstituted phenyl, or substituted or unsubstituted 5 to 6 membered heteroaryl. $R^1$ may be substituted $C_5$-$C_6$ cycloalkyl. $R^1$ may be substituted 5 to 6 membered heterocycloalkyl. $R^1$ may be unsubstituted $C_5$-$C_6$ cycloalkyl. $R^1$ may be unsubstituted 5 to 6 membered heterocycloalkyl.

$R^1$ may be substituted $C_5$ cycloalkyl. $R^1$ may be substituted 5 membered heterocycloalkyl. $R^1$ may be unsubstituted $C_5$ cycloalkyl. $R^1$ may be unsubstituted 5 membered heterocycloalkyl. $R^1$ may be substituted $C_6$ cycloalkyl. $R^1$ may be substituted 6 membered heterocycloalkyl. $R^1$ may be unsubstituted $C_6$ cycloalkyl. $R^1$ may be unsubstituted 6 membered heterocycloalkyl. $R^1$ may be substituted cyclohexyl. $R^1$ may be unsubstituted cyclohexyl.

$R^1$ may be $R^{1A}$-substituted or unsubstituted cycloalkyl. $R^1$ may be $R^{1A}$-substituted or unsubstituted heterocycloalkyl. $R^1$ may be $R^{1A}$-substituted or unsubstituted aryl. $R^1$ may be $R^{1A}$-substituted or unsubstituted heteroaryl. $R^1$ may be $R^{1A}$-substituted cycloalkyl. $R^1$ may be $R^{1A}$-substituted heterocycloalkyl. $R^1$ may be $R^{1A}$-substituted aryl. $R^1$ may be $R^{1A}$-substituted heteroaryl.

$R^1$ may be $R^{1A}$-substituted or unsubstituted $C_3$-$C_8$ cycloalkyl, $R^{1A}$-substituted or unsubstituted 3 to 8 membered heterocycloalkyl, $R^{1A}$-substituted or unsubstituted $C_6$-$C_{10}$ aryl, or $R^{1A}$-substituted or unsubstituted 5 to 10 membered heteroaryl. $R^1$ may be $R^{1A}$-substituted $C_3$-$C_8$ cycloalkyl. $R^1$ may be $R^{1A}$-substituted 3 to 8 membered heterocycloalkyl. $R^1$ may be $R^{1A}$-substituted $C_6$-$C_{10}$ aryl. $R^1$ may be $R^{1A}$-substituted 5 to 10 membered heteroaryl.

$R^1$ may be $R^{1A}$-substituted or unsubstituted $C_4$-$C_6$ cycloalkyl, $R^{1A}$-substituted or unsubstituted 4 to 6 membered heterocycloalkyl, $R^{1A}$-substituted or unsubstituted phenyl, or $R^{1A}$-substituted or unsubstituted 5 to 6 membered heteroaryl. $R^1$ may be $R^{1A}$-substituted $C_4$-$C_6$ cycloalkyl. $R^1$ may be $R^{1A}$-substituted 4 to 6 membered heterocycloalkyl. $R^1$ may be $R^{1A}$-substituted phenyl. $R^1$ may be $R^{1A}$-substituted 5 to 6 membered heteroaryl.

$R^1$ may be $R^{1A}$-substituted or unsubstituted $C_5$-$C_6$ cycloalkyl, $R^{1A}$-substituted or unsubstituted 5 to 6 membered heterocycloalkyl, $R^{1A}$-substituted or unsubstituted phenyl, or $R^{1A}$-substituted or unsubstituted 5 to 6 membered heteroaryl. $R^1$ may be $R^{1A}$-substituted $C_5$-$C_6$ cycloalkyl. $R^1$ may be $R^{1A}$-substituted 5 to 6 membered heterocycloalkyl.

$R^1$ may be $R^{1A}$-substituted $C_5$ cycloalkyl. $R^1$ may be $R^{1A}$-substituted 5 membered heterocycloalkyl. $R^1$ may be $R^{1A}$-substituted $C_6$ cycloalkyl. $R^1$ may be $R^{1A}$-substituted 6 membered heterocycloalkyl. $R^1$ may be $R^{1A}$-substituted cyclohexyl.

$R^{1A}$ is halogen, oxo, $-N_3$, $-CX^{1A}_3$, $-CHX^{1A}_2$, $-CH_2X^{1A}$, $-CN$, $-CHO$, $-OH$, $-NH_2$, $-COOH$, $-CONH_2$, $-NO_2$, $-SH$, $-SO_2$, $-SO_2Cl$, $-SO_2CH_3$—$SO_3H$, $-SO_4H$, $-SO_2NH_2$, $-NHNH_2$, $-ONH_2$, $-NHC(O)NHNH_2$, $R^{1B}$-substituted or unsubstituted alkyl, $R^{1B}$-substituted or unsubstituted heteroalkyl, $R^{1B}$-substituted or unsubstituted cycloalkyl, $R^{1B}$-substituted or unsubstituted heterocycloalkyl, $R^{1B}$-substituted or unsubstituted aryl, or $R^{1B}$-substituted or unsubstituted heteroaryl. $X^{1A}$ is independently a halogen.

$R^{1A}$ may be halogen, oxo, $-N_3$, $-CX^{1A}_3$, $-CHX^{1A}_2$, $-CH_2X^{1A}$, $-CN$, $-CHO$, $-OH$, $-COOH$, $-CONH_2$, $-NO_2$, $-SH$, $-SO_2$, $-SO_2Cl$, $-SO_2CH_3$—$SO_3H$, $-SO_4H$, $-SO_2NH_2$, $-NHNH_2$, $-ONH_2$, $-NHC(O)NHNH_2$, $R^{1B}$-substituted or unsubstituted $C_1$-$C_6$ alkyl, $R^{1B}$-substituted or unsubstituted 2 to 6 membered heteroalkyl, $R^{1B}$-substituted or unsubstituted $C_3$-$C_6$ cycloalkyl, $R^{1B}$-substituted or unsubstituted 3 to 6 membered heterocycloalkyl, $R^{1B}$-substituted or unsubstituted $C_6$ aryl, or $R^{1B}$-substituted or unsubstituted 5 to 6 membered heteroaryl. $X^{1A}$ is independently a halogen.

$R^{1B}$ is halogen, oxo, $-N_3$, $-CX^{1B}_3$, $-CHX^{1B}_2$, $-CH_2X^{1B}$, $-CN$, $-CHO$, $-OH$, $-NH_2$, $-COOH$, $-CONH_2$, $-NO_2$, $-SH$, $-SO_2$, $-SO_2Cl$, $-SO_2CH_3$—$SO_3H$, $-SO_4H$, $-SO_2NH_2$, $-NHNH_2$, $-ONH_2$, $-NHC(O)NHNH_2$, $R^{1C}$-substituted or unsubstituted alkyl, $R^{1C}$-substituted or unsubstituted heteroalkyl, $R^{1C}$-substituted or unsubstituted cycloalkyl, $R^{1C}$-substituted or unsubstituted heterocycloalkyl, $R^{1C}$-substituted or unsubstituted aryl, or $R^{1C}$-substituted or unsubstituted heteroaryl. $X^{1B}$ is independently a halogen.

$R^{1B}$ may be halogen, oxo, $-N_3$, $-CX^{1B}_3$, $-CHX^{1B}_2$, $-CH_2X^{1B}$, $-CN$, $-CHO$, $-OH$, $-NH_2$, $-COOH$, $-CONH_2$, $-NO_2$, $-SH$, $-SO_2$, $-SO_2Cl$, $-SO_2CH_3$—$SO_3H$, $-SO_4H$, $-SO_2NH_2$, $-NHNH_2$, $-ONH_2$, $-NHC(O)NHNH_2$, $R^{1C}$-substituted or unsubstituted $C_1$-$C_6$ alkyl, $R^{1C}$-substituted or unsubstituted 2 to 6 membered heteroalkyl, $R^{1C}$-substituted or unsubstituted $C_3$-$C_6$ cycloalkyl, $R^{1C}$-substituted or unsubstituted 3 to 6 membered heterocycloalkyl, $R^{1C}$-substituted or unsubstituted $C_6$ aryl, or $R^{1C}$-substituted or unsubstituted 5 to 6 membered heteroaryl. $X^{1B}$ is independently a halogen.

$R^{1C}$ is halogen, oxo, —$N_3$, —$CX^{1C}_3$, —$CHX^{1C}_2$, —$CH_2X^{1C}$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —NHC(O)$NHNH_2$, unsubstituted alkyl, unsubstituted heteroalkyl, unsubstituted cycloalkyl, unsubstituted heterocycloalkyl, unsubstituted aryl, or unsubstituted heteroaryl. $X^{1C}$ is independently a halogen.

$R^{1C}$ may be halogen, oxo, —$N_3$, —$CX^{1C}_3$, —$CHX^{1C}_2$, —$CH_2X^{1C}$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —NHC(O)$NHNH_2$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted $C_6$ aryl, or unsubstituted 5 to 6 membered heteroaryl. $X^{1C}$ is independently a halogen.

In embodiments, $R^2$ is independently halogen, —$CX_3$, —$OCX_3$, —$OCHX_2$, substituted or unsubstituted $C_1$-$C_8$ alkyl, or substituted or unsubstituted 2 to 8 membered heteroalkyl. In embodiments, $R^2$ is independently halogen, —$CX_3$, —$OCX_3$, —$OCHX_2$, unsubstituted $C_1$-$C_8$ alkyl, or unsubstituted 2 to 8 membered heteroalkyl. In embodiments, $R^2$ is independently halogen, —$CX_3$, —$OCX_3$, —$OCHX_2$, substituted $C_1$-$C_8$ alkyl, or substituted 2 to 8 membered heteroalkyl. In embodiments, $R^2$ is independently halogen. In embodiments, $R^2$ is independently —$CX_3$. In embodiments, $R^2$ is independently —$OCX_3$. In embodiments, $R^2$ is independently —$OCHX_2$. In embodiments, $R^2$ is independently substituted or unsubstituted $C_1$-$C_8$ alkyl. In embodiments, $R^2$ is independently substituted or unsubstituted 2 to 8 membered heteroalkyl. X may be —F. X may be —Cl. X may be —Br. X may be —I. In embodiments, $R^2$ is independently —F. In embodiments, $R^2$ is independently —Cl. In embodiments, $R^2$ is independently —Br. In embodiments, $R^2$ is independently —I. In embodiments, $R^2$ is independently —$OCHF_2$. In embodiments, $R^2$ is independently —OCHFX. In embodiments, $R^2$ is independently —$CX_3$. In embodiments, $R^2$ is independently —$CF_3$. In embodiments, $R^2$ is independently —$CFX_2$. In embodiments, $R^2$ is independently —$CXF_2$. In embodiments, $R^2$ is independently —$OCX_3$. In embodiments, $R^2$ is independently —$OCF_3$. In embodiments, $R^2$ is independently —$OCFX_2$. In embodiments, $R^2$ is independently —$OCXF_2$. In embodiments, $R^2$ is independently halogen or —$OCHX_2$.

In embodiments, $R^2$ is independently substituted $C_1$-$C_8$ alkyl. In embodiments, $R^2$ is independently substituted 2 to 8 membered heteroalkyl. In embodiments, $R^2$ is independently unsubstituted $C_1$-$C_8$ alkyl. In embodiments, $R^2$ is independently unsubstituted 2 to 8 membered heteroalkyl. In embodiments, $R^2$ is independently substituted $C_1$-$C_6$ alkyl. In embodiments, $R^2$ is independently substituted 2 to 6 membered heteroalkyl. In embodiments, $R^2$ is independently unsubstituted $C_1$-$C_6$ alkyl. In embodiments, $R^2$ is independently unsubstituted 2 to 6 membered heteroalkyl. In embodiments, $R^2$ is independently substituted $C_1$-$C_4$ alkyl. In embodiments, $R^2$ is independently substituted 2 to 4 membered heteroalkyl. In embodiments, $R^2$ is independently unsubstituted $C_1$-$C_4$ alkyl. In embodiments, $R^2$ is independently unsubstituted 2 to 4 membered heteroalkyl.

In embodiments, $R^2$ is independently substituted $C_1$ alkyl. In embodiments, $R^2$ is independently substituted 2 membered heteroalkyl. In embodiments, $R^2$ is independently unsubstituted $C_1$ alkyl. In embodiments, $R^2$ is independently unsubstituted 2 membered heteroalkyl. In embodiments, $R^2$ is independently substituted $C_2$ alkyl. In embodiments, $R^2$ is independently unsubstituted $C_2$ alkyl. In embodiments, $R^2$ is independently substituted $C_3$ alkyl. In embodiments, $R^2$ is independently substituted 3 membered heteroalkyl. In embodiments, $R^2$ is independently unsubstituted $C_3$ alkyl. In embodiments, $R^2$ is independently unsubstituted 3 membered heteroalkyl. In embodiments, $R^2$ is independently substituted $C_4$ alkyl. In embodiments, $R^2$ is independently substituted 4 membered heteroalkyl. In embodiments, $R^2$ is independently unsubstituted $C_4$ alkyl. In embodiments, $R^2$ is independently unsubstituted 4 membered heteroalkyl.

In embodiments, $R^2$ is independently $R^{2A}$-substituted or unsubstituted $C_1$-$C_8$ alkyl. In embodiments, $R^2$ is independently $R^{2A}$-substituted or unsubstituted 2 to 8 membered heteroalkyl. In embodiments, $R^2$ is independently $R^{2A}$-substituted or unsubstituted $C_1$-$C_6$ alkyl. In embodiments, $R^2$ is independently $R^{2A}$-substituted or unsubstituted 2 to 6 membered heteroalkyl. In embodiments, $R^2$ is independently $R^{2A}$-substituted or unsubstituted $C_1$-$C_4$ alkyl. In embodiments, $R^2$ is independently $R^{2A}$-substituted or unsubstituted 2 to 4 membered heteroalkyl. In embodiments, $R^2$ is independently $R^{2A}$-substituted or unsubstituted $C_1$ alkyl. In embodiments, $R^2$ is independently $R^{2A}$-substituted or unsubstituted 2 membered heteroalkyl. In embodiments, $R^2$ is independently $R^{2A}$-substituted or unsubstituted $C_2$ alkyl. In embodiments, $R^2$ is independently $R^{2A}$-substituted or unsubstituted $C_3$ alkyl. In embodiments, $R^2$ is independently $R^{2A}$-substituted or unsubstituted 3 membered heteroalkyl. In embodiments, $R^2$ is independently $R^{2A}$-substituted or unsubstituted $C_4$ alkyl. In embodiments, $R^2$ is independently $R^{2A}$-substituted or unsubstituted 4 membered heteroalkyl.

In embodiments, $R^2$ is independently $R^{2A}$-substituted $C_1$-$C_8$ alkyl. In embodiments, $R^2$ is independently $R^{2A}$-substituted 2 to 8 membered heteroalkyl. In embodiments, $R^2$ is independently $R^{2A}$-substituted $C_1$-$C_6$ alkyl. In embodiments, $R^2$ is independently $R^{2A}$-substituted 2 to 6 membered heteroalkyl. In embodiments, $R^2$ is independently $R^{2A}$-substituted $C_1$-$C_4$ alkyl. In embodiments, $R^2$ is independently $R^{2A}$-substituted 2 to 4 membered heteroalkyl. In embodiments, $R^2$ is independently $R^{2A}$-substituted $C_1$ alkyl. In embodiments, $R^2$ is independently $R^{2A}$-substituted 2 membered heteroalkyl. In embodiments, $R^2$ is independently $R^{2A}$-substituted $C_2$ alkyl. In embodiments, $R^2$ is independently $R^{2A}$-substituted $C_3$ alkyl. In embodiments, $R^2$ is independently $R^{2A}$-substituted 3 membered heteroalkyl. In embodiments, $R^2$ is independently $R^{2A}$-substituted $C_4$ alkyl. In embodiments, $R^2$ is independently $R^{2A}$-substituted 4 membered heteroalkyl.

$R^{2A}$ is halogen, oxo, —$N_3$, —$CX^{2A}_3$, —$CHX^{2A}_2$, —$CH_2X^{2A}$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —NHC(O)$NHNH_2$, $R^{2B}$-substituted or unsubstituted alkyl, $R^{2B}$-substituted or unsubstituted heteroalkyl, $R^{2B}$-substituted or unsubstituted cycloalkyl, $R^{2B}$-substituted or unsubstituted heterocycloalkyl, $R^{2B}$-substituted or unsubstituted aryl, or $R^{2B}$-substituted or unsubstituted heteroaryl. $X^{2A}$ is independently a halogen.

$R^{2A}$ may be halogen, oxo, —$N_3$, —$CX^{2A}_3$, —$CHX^{2A}_2$, —$CH_2X^{2A}$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —NHC(O)$NHNH_2$, $R^{2B}$-substituted or unsubstituted $C_1$-$C_6$ alkyl, $R^{2B}$-substituted or unsubstituted 2 to 6 membered heteroalkyl, $R^{2B}$-substituted or unsubstituted $C_3$-$C_6$ cycloalkyl, $R^{2B}$-substituted or unsubstituted 3 to 6 membered heterocycloalkyl, $R^{2B}$-substituted or unsubstituted $C_6$ aryl, or $R^{2B}$-substituted or unsubstituted 5 to 6 membered heteroaryl. $X^{2A}$ is independently a halogen.

$R^{2B}$ is halogen, oxo, $—N_3$, $—CX^{2B}_3$, $—CHX^{2B}_2$, $—CH_2X^{2B}$, —CN, —CHO, —OH, $—NH_2$, —COOH, $—CONH_2$, $—NO_2$, —SH, $—SO_2$, $—SO_2Cl$, $—SO_2CH_3—SO_3H$, $—SO_4H$, $—SO_2NH_2$, $—NHNH_2$, $—ONH_2$, $—NHC(O)NHNH_2$, $R^{2C}$-substituted or unsubstituted alkyl, $R^{2C}$-substituted or unsubstituted heteroalkyl, $R^{2C}$-substituted or unsubstituted cycloalkyl, $R^{2C}$-substituted or unsubstituted heterocycloalkyl, $R^{2C}$-substituted or unsubstituted aryl, or $R^{2C}$-substituted or unsubstituted heteroaryl. $X^{2B}$ is independently a halogen.

$R^{2B}$ may be halogen, oxo, $—N_3$, $—CX^{2B}_3$, $—CHX^{2B}_2$, $—CH_2X^{2B}$, —CN, —CHO, —OH, $—NH_2$, —COOH, $—CONH_2$, $—NO_2$, —SH, $—SO_2$, $—SO_2Cl$, $—SO_2CH_3—SO_3H$, $—SO_4H$, $—SO_2NH_2$, $—NHNH_2$, $—ONH_2$, $—NHC(O)NHNH_2$, $R^{2C}$-substituted or unsubstituted $C_1$-$C_6$ alkyl, $R^{2C}$-substituted or unsubstituted 2 to 6 membered heteroalkyl, $R^{2C}$-substituted or unsubstituted $C_3$-$C_6$ cycloalkyl, $R^{2C}$-substituted or unsubstituted 3 to 6 membered heterocycloalkyl, $R^{2C}$-substituted or unsubstituted $C_6$ aryl, or $R^{2C}$-substituted or unsubstituted 5 to 6 membered heteroaryl. $X^{2B}$ is independently a halogen.

$R^{2C}$ is halogen, oxo, $—N_3$, $—CX^{2C}_3$, $—CHX^{2C}_2$, $—CH_2X^{2C}$, —CN, —CHO, —OH, $—NH_2$, —COOH, $—CONH_2$, $—NO_2$, —SH, $—SO_2$, $—SO_2Cl$, $—SO_2CH_3—SO_3H$, $—SO_4H$, $—SO_2NH_2$, $—NHNH_2$, $—ONH_2$, $—NHC(O)NHNH_2$, unsubstituted alkyl, unsubstituted heteroalkyl, unsubstituted cycloalkyl, unsubstituted heterocycloalkyl, unsubstituted aryl, or unsubstituted heteroaryl. $X^{2C}$ is independently a halogen.

$R^{2C}$ may be halogen, oxo, $—N_3$, $—CX^{2C}_3$, $—CHX^{2C}_2$, $—CH_2X^{2C}$, —CN, —CHO, —OH, —COOH, $—CONH_2$, $—NO_2$, —SH, $—SO_2$, $—SO_2Cl$, $—SO_2CH_3—SO_3H$, $—SO_4H$, $—SO_2NH_2$, $—NHNH_2$, $—ONH_2$, $—NHC(O)NHNH_2$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted $C_6$ aryl, or unsubstituted 5 to 6 membered heteroaryl. $X^{2C}$ is independently a halogen.

$R^3$ may be $—SO_2R^6$. $R^3$ may be $—SO_2NR^4R^5$. $R^3$ may be $—C(O)NR^4R^5$.

In embodiments, $R^4$ is independently hydrogen, substituted or unsubstituted $C_1$-$C_8$ alkyl, or substituted or unsubstituted 2 to 8 membered heteroalkyl. In embodiments, $R^4$ is independently hydrogen, unsubstituted $C_1$-$C_8$ alkyl, or unsubstituted 2 to 8 membered heteroalkyl. In embodiments, $R^4$ is independently hydrogen, substituted $C_1$-$C_8$ alkyl, or substituted 2 to 8 membered heteroalkyl. In embodiments, $R^4$ is independently hydrogen. In embodiments, $R^4$ is independently substituted or unsubstituted $C_1$-$C_8$ alkyl. In embodiments, $R^4$ is independently substituted or unsubstituted 2 to 8 membered heteroalkyl.

In embodiments, $R^4$ is independently substituted $C_1$-$C_8$ alkyl. In embodiments, $R^4$ is independently substituted 2 to 8 membered heteroalkyl. In embodiments, $R^4$ is independently unsubstituted $C_1$-$C_8$ alkyl. In embodiments, $R^4$ is independently unsubstituted 2 to 8 membered heteroalkyl. In embodiments, $R^4$ is independently substituted $C_1$-$C_6$ alkyl. In embodiments, $R^4$ is independently substituted 2 to 6 membered heteroalkyl. In embodiments, $R^4$ is independently unsubstituted $C_1$-$C_6$ alkyl. In embodiments, $R^4$ is independently unsubstituted 2 to 6 membered heteroalkyl. In embodiments, $R^4$ is independently substituted $C_1$-$C_4$ alkyl. In embodiments, $R^4$ is independently substituted 2 to 4 membered heteroalkyl. In embodiments, $R^4$ is independently unsubstituted $C_1$-$C_4$ alkyl. In embodiments, $R^4$ is independently unsubstituted 2 to 4 membered heteroalkyl.

In embodiments, $R^4$ is independently substituted $C_1$ alkyl. In embodiments, $R^4$ is independently substituted 2 membered heteroalkyl. In embodiments, $R^4$ is independently unsubstituted $C_1$ alkyl. In embodiments, $R^4$ is independently unsubstituted 2 membered heteroalkyl. In embodiments, $R^4$ is independently substituted $C_2$ alkyl. In embodiments, $R^4$ is independently unsubstituted $C_2$ alkyl. In embodiments, $R^4$ is independently substituted $C_3$ alkyl. In embodiments, $R^4$ is independently substituted 3 membered heteroalkyl. In embodiments, $R^4$ is independently unsubstituted $C_3$ alkyl. In embodiments, $R^4$ is independently unsubstituted 3 membered heteroalkyl. In embodiments, $R^4$ is independently substituted $C_4$ alkyl. In embodiments, $R^4$ is independently substituted 4 membered heteroalkyl. In embodiments, $R^4$ is independently unsubstituted $C_4$ alkyl. In embodiments, $R^4$ is independently unsubstituted 4 membered heteroalkyl. In embodiments, $R^4$ is independently substituted methyl. In embodiments, $R^4$ is independently unsubstituted methyl.

In embodiments, $R^4$ is independently $R^{4A}$-substituted or unsubstituted $C_1$-$C_8$ alkyl. In embodiments, $R^4$ is independently $R^{4A}$-substituted or unsubstituted 2 to 8 membered heteroalkyl. In embodiments, $R^4$ is independently $R^{4A}$-substituted or unsubstituted $C_1$-$C_6$ alkyl. In embodiments, $R^4$ is independently $R^{4A}$-substituted or unsubstituted 2 to 6 membered heteroalkyl. In embodiments, $R^4$ is independently $R^{4A}$-substituted or unsubstituted $C_1$-$C_4$ alkyl. In embodiments, $R^4$ is independently $R^{4A}$-substituted or unsubstituted 2 to 4 membered heteroalkyl. In embodiments, $R^4$ is independently $R^{4A}$-substituted or unsubstituted $C_1$ alkyl. In embodiments, $R^4$ is independently $R^{4A}$-substituted or unsubstituted 2 membered heteroalkyl. In embodiments, $R^4$ is independently $R^{4A}$-substituted or unsubstituted $C_2$ alkyl. In embodiments, $R^4$ is independently $R^{4A}$-substituted or unsubstituted $C_3$ alkyl. In embodiments, $R^4$ is independently $R^{4A}$-substituted or unsubstituted 3 membered heteroalkyl. In embodiments, $R^4$ is independently $R^{4A}$-substituted or unsubstituted $C_4$ alkyl. In embodiments, $R^4$ is independently $R^{4A}$-substituted or unsubstituted 4 membered heteroalkyl.

In embodiments, $R^4$ is independently $R^{4A}$-substituted $C_1$-$C_8$ alkyl. In embodiments, $R^4$ is independently $R^{4A}$-substituted 2 to 8 membered heteroalkyl. In embodiments, $R^4$ is independently $R^{4A}$-substituted $C_1$-$C_6$ alkyl. In embodiments, $R^4$ is independently $R^{4A}$-substituted 2 to 6 membered heteroalkyl. In embodiments, $R^4$ is independently $R^{4A}$-substituted $C_1$-$C_4$ alkyl. In embodiments, $R^4$ is independently $R^{4A}$-substituted 2 to 4 membered heteroalkyl. In embodiments, $R^4$ is independently $R^{4A}$-substituted $C_1$ alkyl. In embodiments, $R^4$ is independently $R^{4A}$-substituted 2 membered heteroalkyl. In embodiments, $R^4$ is independently $R^{4A}$-substituted $C_2$ alkyl. In embodiments, $R^4$ is independently $R^{4A}$-substituted $C_3$ alkyl. In embodiments, $R^4$ is independently $R^{4A}$-substituted 3 membered heteroalkyl. In embodiments, $R^4$ is independently $R^{4A}$-substituted $C_4$ alkyl. In embodiments, $R^4$ is independently $R^{4A}$-substituted 4 membered heteroalkyl.

$R^{4A}$ is halogen, oxo, $—N_3$, $—CX^{4A}_3$, $—CHX^{4A}_2$, $—CH_2X^{4A}$, —CN, —CHO, —OH, $—NH_2$, —COOH, $—CONH_2$, $—NO_2$, —SH, $—SO_2$, $—SO_2Cl$, $—SO_2CH_3—SO_3H$, $—SO_4H$, $—SO_2NH_2$, $—NHNH_2$, $—ONH_2$, $—NHC(O)NHNH_2$, $R^{4B}$-substituted or unsubstituted alkyl, $R^{4B}$-substituted or unsubstituted heteroalkyl, $R^{4B}$-substituted or unsubstituted cycloalkyl, $R^{4B}$-substituted or unsubstituted heterocycloalkyl, $R^{4B}$-substituted or unsubstituted aryl, or $R^{4B}$-substituted or unsubstituted heteroaryl. $X^{4A}$ is independently a halogen.

$R^{4A}$ may be halogen, oxo, $—N_3$, $—CX^{4A}_3$, $—CHX^{4A}_2$, $—CH_2X^{4A}$, —CN, —CHO, —OH, $—NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —NHC(O)$NHNH_2$, $R^{4B}$-substituted or unsubstituted $C_1$-$C_6$ alkyl, $R^{4B}$-substituted or unsubstituted 2 to 6 membered heteroalkyl, $R^{4B}$-substituted or unsubstituted $C_3$-$C_6$ cycloalkyl, $R^{4B}$-substituted or unsubstituted 3 to 6 membered heterocycloalkyl, $R^{4B}$-substituted or unsubstituted $C_6$ aryl, or $R^{4B}$-substituted or unsubstituted 5 to 6 membered heteroaryl. $X^{4A}$ is independently a halogen.

$R^{4B}$ is halogen, oxo, —$N_3$, —$CX^{4B}_3$, —$CHX^{4B}_2$, —$CH_2X^{4B}$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —NHC(O)$NHNH_2$, $R^{4C}$-substituted or unsubstituted alkyl, $R^{4C}$-substituted or unsubstituted heteroalkyl, $R^{4C}$-substituted or unsubstituted cycloalkyl, $R^{4C}$-substituted or unsubstituted heterocycloalkyl, $R^{4C}$-substituted or unsubstituted aryl, or $R^{4C}$-substituted or unsubstituted heteroaryl. $X^{4B}$ is independently a halogen.

$R^{4B}$ may be halogen, oxo, —$N_3$, —$CX^{4B}_3$, —$CHX^{4B}_2$, —$CH_2X^{4B}$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —NHC(O)$NHNH_2$, $R^{4C}$-substituted or unsubstituted $C_1$-$C_6$ alkyl, $R^{4C}$-substituted or unsubstituted 2 to 6 membered heteroalkyl, $R^{4C}$-substituted or unsubstituted $C_3$-$C_6$ cycloalkyl, $R^{4C}$-substituted or unsubstituted 3 to 6 membered heterocycloalkyl, $R^{4C}$-substituted or unsubstituted $C_6$ aryl, or $R^{4C}$-substituted or unsubstituted 5 to 6 membered heteroaryl. $X^{4B}$ is independently a halogen.

$R^{4C}$ is halogen, oxo, —$N_3$, —$CX^{4C}_3$, —$CHX^{4C}_2$, —$CH_2X^{4C}$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —NHC(O)$NHNH_2$, unsubstituted alkyl, unsubstituted heteroalkyl, unsubstituted cycloalkyl, unsubstituted heterocycloalkyl, unsubstituted aryl, or unsubstituted heteroaryl. $X^{4C}$ is independently a halogen.

$R^{4C}$ may be halogen, oxo, —$N_3$, —$CX^{4C}_3$, —$CHX^{4C}_2$, —$CH_2X^{4C}$, —CN, —CHO, —OH, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —NHC(O)$NHNH_2$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted $C_6$ aryl, or unsubstituted 5 to 6 membered heteroaryl. $X^{4C}$ is independently a halogen.

In embodiments, $R^5$ is independently hydrogen, substituted or unsubstituted $C_1$-$C_8$ alkyl, or substituted or unsubstituted 2 to 8 membered heteroalkyl. In embodiments, $R^5$ is independently hydrogen, unsubstituted $C_1$-$C_8$ alkyl, or unsubstituted 2 to 8 membered heteroalkyl. In embodiments, $R^5$ is independently hydrogen, substituted $C_1$-$C_8$ alkyl, or substituted 2 to 8 membered heteroalkyl. In embodiments, $R^5$ is independently hydrogen. In embodiments, $R^5$ is independently substituted or unsubstituted $C_1$-$C_8$ alkyl. In embodiments, $R^5$ is independently substituted or unsubstituted 2 to 8 membered heteroalkyl.

In embodiments, $R^5$ is independently substituted $C_1$-$C_8$ alkyl. In embodiments, $R^5$ is independently substituted 2 to 8 membered heteroalkyl. In embodiments, $R^5$ is independently unsubstituted $C_1$-$C_8$ alkyl. In embodiments, $R^5$ is independently unsubstituted 2 to 8 membered heteroalkyl. In embodiments, $R^5$ is independently substituted $C_1$-$C_6$ alkyl. In embodiments, $R^5$ is independently substituted 2 to 6 membered heteroalkyl. In embodiments, $R^5$ is independently unsubstituted $C_1$-$C_6$ alkyl. In embodiments, $R^5$ is independently unsubstituted 2 to 6 membered heteroalkyl. In embodiments, $R^5$ is independently substituted $C_1$-$C_4$ alkyl. In embodiments, $R^5$ is independently substituted 2 to 4 membered heteroalkyl. In embodiments, $R^5$ is independently unsubstituted $C_1$-$C_4$ alkyl. In embodiments, $R^5$ is independently unsubstituted 2 to 4 membered heteroalkyl.

In embodiments, $R^5$ is independently substituted $C_1$ alkyl. In embodiments, $R^5$ is independently substituted 2 membered heteroalkyl. In embodiments, $R^5$ is independently unsubstituted $C_1$ alkyl. In embodiments, $R^5$ is independently unsubstituted 2 membered heteroalkyl. In embodiments, $R^5$ is independently substituted $C_2$ alkyl. In embodiments, $R^5$ is independently unsubstituted $C_2$ alkyl. In embodiments, $R^5$ is independently substituted $C_3$ alkyl. In embodiments, $R^5$ is independently substituted 3 membered heteroalkyl. In embodiments, $R^5$ is independently unsubstituted $C_3$ alkyl. In embodiments, $R^5$ is independently unsubstituted 3 membered heteroalkyl. In embodiments, $R^5$ is independently substituted $C_4$ alkyl. In embodiments, $R^5$ is independently substituted 4 membered heteroalkyl. In embodiments, $R^5$ is independently unsubstituted $C_4$ alkyl. In embodiments, $R^5$ is independently unsubstituted 4 membered heteroalkyl. In embodiments, $R^5$ is independently substituted methyl. In embodiments, $R^5$ is independently unsubstituted methyl.

In embodiments, $R^5$ is independently $R^{5A}$-substituted or unsubstituted $C_1$-$C_8$ alkyl. In embodiments, $R^5$ is independently $R^{5A}$-substituted or unsubstituted 2 to 8 membered heteroalkyl. In embodiments, $R^5$ is independently $R^{5A}$-substituted or unsubstituted $C_1$-$C_6$ alkyl. In embodiments, $R^5$ is independently $R^{5A}$-substituted or unsubstituted 2 to 6 membered heteroalkyl. In embodiments, $R^5$ is independently $R^{5A}$-substituted or unsubstituted $C_1$-$C_4$ alkyl. In embodiments, $R^5$ is independently $R^{5A}$-substituted or unsubstituted 2 to 4 membered heteroalkyl. In embodiments, $R^5$ is independently $R^{5A}$-substituted or unsubstituted $C_1$ alkyl. In embodiments, $R^5$ is independently $R^{5A}$-substituted or unsubstituted 2 membered heteroalkyl. In embodiments, $R^5$ is independently $R^{5A}$-substituted or unsubstituted $C_2$ alkyl. In embodiments, $R^5$ is independently $R^{5A}$-substituted or unsubstituted $C_3$ alkyl. In embodiments, $R^5$ is independently $R^{5A}$-substituted or unsubstituted 3 membered heteroalkyl. In embodiments, $R^5$ is independently $R^{5A}$-substituted or unsubstituted $C_4$ alkyl. In embodiments, $R^5$ is independently $R^{5A}$-substituted or unsubstituted 4 membered heteroalkyl.

In embodiments, $R^5$ is independently $R^{5A}$-substituted $C_1$-$C_8$ alkyl. In embodiments, $R^5$ is independently $R^{5A}$-substituted 2 to 8 membered heteroalkyl. In embodiments, $R^5$ is independently $R^{5A}$-substituted $C_1$-$C_6$ alkyl. In embodiments, $R^5$ is independently $R^{5A}$-substituted 2 to 6 membered heteroalkyl. In embodiments, $R^5$ is independently $R^{5A}$-substituted $C_1$-$C_4$ alkyl. In embodiments, $R^5$ is independently $R^{5A}$-substituted 2 to 4 membered heteroalkyl. In embodiments, $R^5$ is independently $R^{5A}$-substituted $C_1$ alkyl. In embodiments, $R^5$ is independently $R^{5A}$-substituted 2 membered heteroalkyl. In embodiments, $R^5$ is independently $R^{5A}$-substituted $C_2$ alkyl. In embodiments, $R^5$ is independently $R^{5A}$-substituted $C_3$ alkyl. In embodiments, $R^5$ is independently $R^{5A}$-substituted 3 membered heteroalkyl. In embodiments, $R^5$ is independently $R^{5A}$-substituted $C_4$ alkyl. In embodiments, $R^5$ is independently $R^{5A}$-substituted 4 membered heteroalkyl.

$R^{5A}$ is halogen, oxo, —$N_3$, —$CX^{5A}_3$, —$CHX^{5A}_2$, —$CH_2X^{5A}$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —NHC(O)$NHNH_2$, $R^{5B}$-substituted or unsubstituted alkyl, $R^{5B}$-substituted or unsubstituted heteroalkyl, $R^{5B}$-substituted or unsubstituted cycloalkyl, $R^{5B}$-substituted or unsubstituted heterocycloalkyl, $R^{5B}$-substituted or unsubstituted aryl, or $R^{5B}$-substituted or unsubstituted heteroaryl. $X^{5A}$ is independently a halogen.

$R^{5A}$ may be halogen, oxo, —$N_3$, —$CX^{5A}_3$, —$CHX^{5A}_2$, —$CH_2X^{5A}$, —CN, —CHO, —OH, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —NHC(O)$NHNH_2$, $R^{5B}$-substituted or unsubstituted $C_1$-$C_6$ alkyl, $R^{5B}$-substituted or unsubstituted 2 to 6 membered heteroalkyl, $R^{5B}$-substituted or unsubstituted $C_3$-$C_6$ cycloalkyl, $R^{5B}$-substituted or unsubstituted 3 to 6 membered heterocycloalkyl, $R^{5B}$-substituted or unsubstituted $C_6$ aryl, or $R^{5B}$-substituted or unsubstituted 5 to 6 membered heteroaryl. $X^{5A}$ is independently a halogen.

$R^{5B}$ is halogen, oxo, —$N_3$, —$CX^{5B}_3$, —$CHX^{5B}_2$, —$CH_2X^{5B}$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —NHC(O)$NHNH_2$, $R^{5C}$-substituted or unsubstituted alkyl, $R^{5C}$-substituted or unsubstituted heteroalkyl, $R^{5C}$-substituted or unsubstituted cycloalkyl, $R^{5C}$-substituted or unsubstituted heterocycloalkyl, $R^{5C}$-substituted or unsubstituted aryl, or $R^{5C}$-substituted or unsubstituted heteroaryl. $X^{5B}$ is independently a halogen.

$R^{5B}$ may be halogen, oxo, —$N_3$, —$CX^{5B}_3$, —$CHX^{5B}_2$, —$CH_2X^{5B}$, —CN, —CHO, —OH, —COOH, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —NHC(O)$NHNH_2$, $R^{5C}$-substituted or unsubstituted $C_1$-$C_6$ alkyl, $R^{5C}$-substituted or unsubstituted 2 to 6 membered heteroalkyl, $R^{5C}$-substituted or unsubstituted $C_3$-$C_6$ cycloalkyl, $R^{5C}$-substituted or unsubstituted 3 to 6 membered heterocycloalkyl, $R^{5C}$-substituted or unsubstituted $C_6$ aryl, or $R^{5C}$-substituted or unsubstituted 5 to 6 membered heteroaryl. $X^{5B}$ is independently a halogen.

$R^{5C}$ is halogen, oxo, —$N_3$, —$CX^{5C}_3$, —$CHX^{5C}_2$, —$CH_2X^{5C}$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —NHC(O)$NHNH_2$, unsubstituted alkyl, unsubstituted heteroalkyl, unsubstituted cycloalkyl, unsubstituted heterocycloalkyl, unsubstituted aryl, or unsubstituted heteroaryl. $X^{5C}$ is independently a halogen.

$R^{5C}$ may be halogen, oxo, —$N_3$, —$CX^{5C}_3$, —$CHX^{5C}_2$, —$CH_2X^{5C}$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —NHC(O)$NHNH_2$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted $C_6$ aryl, or unsubstituted 5 to 6 membered heteroaryl. $X^{5C}$ is independently a halogen.

$R^4$ and $R^5$ bonded to the same nitrogen atom, may be joined to independently form a substituted or unsubstituted 4 to 8 membered heterocycloalkyl or substituted or unsubstituted 5 to 6 membered heteroaryl.

In embodiments, $R^4$ and $R^5$ are joined to independently form a substituted or unsubstituted 4 to 8 membered heterocycloalkyl. In embodiments, $R^4$ and $R^5$ are joined to independently form a substituted or unsubstituted 5 to 6 membered heteroaryl. In embodiments, $R^4$ and $R^5$ are joined to independently form a substituted 4 to 8 membered heterocycloalkyl. In embodiments, $R^4$ and $R^5$ are joined to independently form a substituted 5 to 6 membered heteroaryl. In embodiments, $R^4$ and $R^5$ are joined to independently form an unsubstituted 4 to 8 membered heterocycloalkyl. In embodiments, $R^4$ and $R^5$ are joined to independently form an unsubstituted 5 to 6 membered heteroaryl. In embodiments, $R^4$ and $R^5$ are joined to independently form a substituted 5 to 6 membered heterocycloalkyl. In embodiments, $R^4$ and $R^5$ are joined to independently form an unsubstituted 5 to 6 membered heterocycloalkyl.

In embodiments, $R^4$ and $R^5$ are joined to independently form a substituted 5 membered heterocycloalkyl. In embodiments, $R^4$ and $R^5$ are joined to independently form an unsubstituted 5 membered heterocycloalkyl. In embodiments, $R^4$ and $R^5$ are joined to independently form a substituted 5 membered heteroaryl. In embodiments, $R^4$ and $R^5$ are joined to independently form an unsubstituted 5 membered heteroaryl. In embodiments, $R^4$ and $R^5$ are joined to independently form a substituted 6 membered heterocycloalkyl. In embodiments, $R^4$ and $R^5$ are joined to independently form an unsubstituted 6 membered heterocycloalkyl. In embodiments, $R^4$ and $R^5$ are joined to independently form a substituted 6 membered heteroaryl. In embodiments, $R^4$ and $R^5$ are joined to independently form an unsubstituted 6 membered heteroaryl. In embodiments, $R^4$ and $R^5$ are joined to independently form a substituted 7 membered heterocycloalkyl. In embodiments, $R^4$ and $R^5$ are joined to independently form an unsubstituted 7 membered heterocycloalkyl. In embodiments, $R^4$ and $R^5$ are joined to independently form a substituted 4 membered heterocycloalkyl. In embodiments, $R^4$ and $R^5$ are joined to independently form an unsubstituted 4 membered heterocycloalkyl.

$R^4$ and $R^5$ bonded to the same nitrogen atom, may be joined to independently form a $R^{5A}$-substituted or unsubstituted 4 to 8 membered heterocycloalkyl or $R^{5A}$-substituted or unsubstituted 5 to 6 membered heteroaryl.

In embodiments, $R^4$ and $R^5$ are joined to independently form a $R^{5A}$-substituted or unsubstituted 4 to 8 membered heterocycloalkyl. In embodiments, $R^4$ and $R^5$ are joined to independently form a $R^{5A}$-substituted or unsubstituted 5 to 6 membered heteroaryl. In embodiments, $R^4$ and $R^5$ are joined to independently form a $R^{5A}$-substituted 4 to 8 membered heterocycloalkyl. In embodiments, $R^4$ and $R^5$ are joined to independently form a $R^{5A}$-substituted 5 to 6 membered heteroaryl. In embodiments, $R^4$ and $R^5$ are joined to independently form a $R^{5A}$-substituted 5 to 6 membered heterocycloalkyl.

In embodiments, $R^4$ and $R^5$ are joined to independently form a $R^{5A}$-substituted 5 membered heterocycloalkyl. In embodiments, $R^4$ and $R^5$ are joined to independently form a $R^{5A}$-substituted 5 membered heteroaryl. In embodiments, $R^4$ and $R^5$ are joined to independently form a $R^{5A}$-substituted 6 membered heterocycloalkyl. In embodiments, $R^4$ and $R^5$ are joined to independently form a $R^{5A}$-substituted 6 membered heteroaryl. In embodiments, $R^4$ and $R^5$ are joined to independently form a $R^{5A}$-substituted 7 membered heterocycloalkyl. In embodiments, $R^4$ and $R^5$ are joined to independently form a $R^{5A}$-substituted 4 membered heterocycloalkyl.

In embodiments, $R^6$ is independently hydrogen, substituted or unsubstituted $C_1$-$C_8$ alkyl, or substituted or unsubstituted 2 to 8 membered heteroalkyl. In embodiments, $R^6$ is independently hydrogen, unsubstituted $C_1$-$C_8$ alkyl, or unsubstituted 2 to 8 membered heteroalkyl. In embodiments, $R^6$ is independently hydrogen, substituted $C_1$-$C_8$ alkyl, or substituted 2 to 8 membered heteroalkyl. In embodiments, $R^6$ is independently hydrogen. In embodiments, $R^6$ is independently substituted or unsubstituted $C_1$-$C_8$ alkyl. In embodiments, $R^6$ is independently substituted or unsubstituted 2 to 8 membered heteroalkyl.

In embodiments, $R^6$ is independently substituted $C_1$-$C_8$ alkyl. In embodiments, $R^6$ is independently substituted 2 to 8 membered heteroalkyl. In embodiments, $R^6$ is independently unsubstituted $C_1$-$C_8$ alkyl. In embodiments, $R^6$ is independently unsubstituted 2 to 8 membered heteroalkyl. In embodiments, $R^6$ is independently substituted $C_1$-$C_6$ alkyl. In embodiments, $R^6$ is independently substituted 2 to 6 membered heteroalkyl. In embodiments, $R^6$ is independently unsubstituted $C_1$-$C_6$ alkyl. In embodiments, $R^6$ is independently unsubstituted 2 to 6 membered heteroalkyl. In embodiments, $R^6$ is independently substituted $C_1$-$C_4$ alkyl. In embodiments, $R^6$ is independently substituted 2 to 4 membered heteroalkyl. In embodiments, $R^6$ is independently unsubstituted $C_1$-$C_4$ alkyl. In embodiments, $R^6$ is independently unsubstituted 2 to 4 membered heteroalkyl.

In embodiments, $R^6$ is independently substituted $C_1$ alkyl. In embodiments, $R^6$ is independently substituted 2 membered heteroalkyl. In embodiments, $R^6$ is independently unsubstituted $C_1$ alkyl. In embodiments, $R^6$ is independently unsubstituted 2 membered heteroalkyl. In embodiments, $R^6$ is independently substituted $C_2$ alkyl. In embodiments, $R^6$ is independently unsubstituted $C_2$ alkyl. In embodiments, $R^6$ is independently substituted $C_3$ alkyl. In embodiments, $R^6$ is independently substituted 3 membered heteroalkyl. In embodiments, $R^6$ is independently unsubstituted $C_3$ alkyl. In embodiments, $R^6$ is independently unsubstituted 3 membered heteroalkyl. In embodiments, $R^6$ is independently substituted $C_4$ alkyl. In embodiments, $R^6$ is independently substituted 4 membered heteroalkyl. In embodiments, $R^6$ is independently unsubstituted $C_4$ alkyl. In embodiments, $R^6$ is independently unsubstituted 4 membered heteroalkyl. In embodiments, $R^6$ is independently substituted methyl. In embodiments, $R^6$ is independently unsubstituted methyl.

In embodiments, $R^6$ is independently $R^{6A}$-substituted or unsubstituted $C_1$-$C_8$ alkyl. In embodiments, $R^6$ is independently $R^{6A}$-substituted or unsubstituted 2 to 8 membered heteroalkyl. In embodiments, $R^6$ is independently $R^{6A}$-substituted or unsubstituted $C_1$-$C_6$ alkyl. In embodiments, $R^6$ is independently $R^{6A}$-substituted or unsubstituted 2 to 6 membered heteroalkyl. In embodiments, $R^6$ is independently $R^{6A}$-substituted or unsubstituted $C_1$-$C_4$ alkyl. In embodiments, $R^6$ is independently $R^{6A}$-substituted or unsubstituted 2 to 4 membered heteroalkyl. In embodiments, $R^6$ is independently $R^{6A}$-substituted or unsubstituted $C_1$ alkyl. In embodiments, $R^6$ is independently $R^{6A}$-substituted or unsubstituted 2 membered heteroalkyl. In embodiments, $R^6$ is independently $R^{6A}$-substituted or unsubstituted $C_2$ alkyl. In embodiments, $R^6$ is independently $R^{6A}$-substituted or unsubstituted $C_3$ alkyl. In embodiments, $R^6$ is independently $R^{6A}$-substituted or unsubstituted 3 membered heteroalkyl. In embodiments, $R^6$ is independently $R^{6A}$-substituted or unsubstituted $C_4$ alkyl. In embodiments, $R^6$ is independently $R^{6A}$-substituted or unsubstituted 4 membered heteroalkyl.

In embodiments, $R^6$ is independently $R^{6A}$-substituted $C_1$-$C_8$ alkyl. In embodiments, $R^6$ is independently $R^{6A}$-substituted 2 to 8 membered heteroalkyl. In embodiments, $R^6$ is independently $R^{6A}$-substituted $C_1$-$C_6$ alkyl. In embodiments, $R^6$ is independently $R^{6A}$-substituted 2 to 6 membered heteroalkyl. In embodiments, $R^6$ is independently $R^{6A}$-substituted $C_1$-$C_4$ alkyl. In embodiments, $R^6$ is independently $R^{6A}$-substituted 2 to 4 membered heteroalkyl. In embodiments, $R^6$ is independently $R^{6A}$-substituted $C_1$ alkyl. In embodiments, $R^6$ is independently $R^{6A}$-substituted 2 membered heteroalkyl. In embodiments, $R^6$ is independently $R^{6A}$-substituted $C_2$ alkyl. In embodiments, $R^6$ is independently $R^{6A}$-substituted $C_3$ alkyl. In embodiments, $R^6$ is independently $R^{6A}$-substituted 3 membered heteroalkyl. In embodiments, $R^6$ is independently $R^{6A}$-substituted $C_4$ alkyl. In embodiments, $R^6$ is independently $R^{6A}$-substituted 4 membered heteroalkyl.

$R^{6A}$ is halogen, oxo, —$N_3$, —$CX^{6A}_3$, —$CHX^{6A}_2$, —$CH_2X^{6A}$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —NHC(O)$NHNH_2$, $R^{6B}$-substituted or unsubstituted alkyl, $R^{6B}$-substituted or unsubstituted heteroalkyl, $R^{6B}$-substituted or unsubstituted cycloalkyl, $R^{6B}$-substituted or unsubstituted heterocycloalkyl, $R^{6B}$-substituted or unsubstituted aryl, or $R^{6B}$-substituted or unsubstituted heteroaryl. $X^{6A}$ is independently a halogen.

$R^{6A}$ may be halogen, oxo, —$N_3$, —$CX^{6A}_3$, —$CHX^{6A}_2$, —$CH_2X^{6A}$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —NHC(O)$NHNH_2$, $R^{6B}$-substituted or unsubstituted $C_1$-$C_6$ alkyl, $R^{6B}$-substituted or unsubstituted 2 to 6 membered heteroalkyl, $R^{6B}$-substituted or unsubstituted $C_3$-$C_6$ cycloalkyl, $R^{6B}$-substituted or unsubstituted 3 to 6 membered heterocycloalkyl, $R^{6B}$-substituted or unsubstituted $C_6$ aryl, or $R^{6B}$-substituted or unsubstituted 5 to 6 membered heteroaryl. $X^{6A}$ is independently a halogen.

$R^{6B}$ is halogen, oxo, —$N_3$, —$CX^{6B}_3$, —$CHX^{6B}_2$, —$CH_2X^{6B}$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —NHC(O)$NHNH_2$, $R^{6C}$-substituted or unsubstituted alkyl, $R^{6C}$-substituted or unsubstituted heteroalkyl, $R^{6C}$-substituted or unsubstituted cycloalkyl, $R^{6C}$-substituted or unsubstituted heterocycloalkyl, $R^{6C}$-substituted or unsubstituted aryl, or $R^{6C}$-substituted or unsubstituted heteroaryl. $X^{6B}$ is independently a halogen.

$R^{6B}$ may be halogen, oxo, —$N_3$, —$CX^{6B}_3$, —$CHX^{6B}_2$, —$CH_2X^{6B}$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —NHC(O)$NHNH_2$, $R^{6C}$-substituted or unsubstituted $C_1$-$C_6$ alkyl, $R^{6C}$-substituted or unsubstituted 2 to 6 membered heteroalkyl, $R^{6C}$-substituted or unsubstituted $C_3$-$C_6$ cycloalkyl, $R^{6C}$-substituted or unsubstituted 3 to 6 membered heterocycloalkyl, $R^{6C}$-substituted or unsubstituted $C_6$ aryl, or $R^{6C}$-substituted or unsubstituted 5 to 6 membered heteroaryl. $X^{6B}$ is independently a halogen.

$R^{6C}$ is halogen, oxo, —$N_3$, —$CX^{6C}_3$, —$CHX^{6C}_2$, —$CH_2X^{6C}$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —NHC(O)$NHNH_2$, unsubstituted alkyl, unsubstituted heteroalkyl, unsubstituted cycloalkyl, unsubstituted heterocycloalkyl, unsubstituted aryl, or unsubstituted heteroaryl. $X^{6C}$ is independently a halogen.

$R^{6C}$ may be halogen, oxo, —$N_3$, —$CX^{6C}_3$, —$CHX^{6C}_2$, —$CH_2X^{6C}$, —CN, —CHO, —OH, —$NH_2$, —COOH, —$CONH_2$, —$NO_2$, —SH, —$SO_2$, —$SO_2Cl$, —$SO_2CH_3$—$SO_3H$, —$SO_4H$, —$SO_2NH_2$, —$NHNH_2$, —$ONH_2$, —NHC(O)$NHNH_2$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted $C_6$ aryl, or unsubstituted 5 to 6 membered heteroaryl. $X^6$ is independently a halogen.

The symbol z may be an integer from 2 to 4. The symbol z may be an integer from 3 to 4. The symbol z may be an integer from 1 to 3. The symbol z may be an integer from 1 to 2. The symbol z may be 1. The symbol z may be 2. The symbol z may be 3. The symbol z may be 4.

In embodiments, $R^1$ is cyclobutyl, cyclopentyl, or cyclohexyl; $R^2$ is —F or —$OCHF_2$; $R^3$ is —$SO_2NH_2$, —$SO_2NHMe$, —$SO_2NMe_2$, —$CONH_2$, —CONHMe, —$CONMe_2$, or —$SO_2Me$; and z is 1.
In embodiments, $R^1$ is cyclobutyl, cyclopentyl, or cyclohexyl; $R^2$ is —F or —$OCHF_2$; and $R^3$ is —$SO_2NH_2$, —$SO_2NHMe$, —$SO_2NMe_2$, —$CONH_2$, —CONHMe, —$CONMe_2$, or —$SO_2Me$.
In embodiments, the compound is
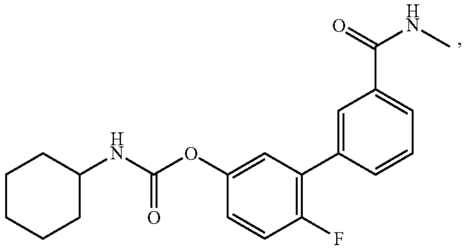
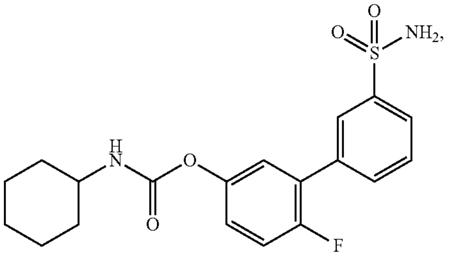
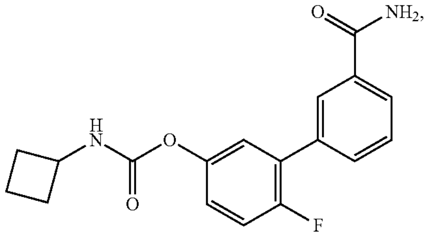
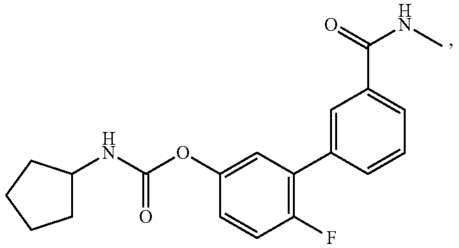
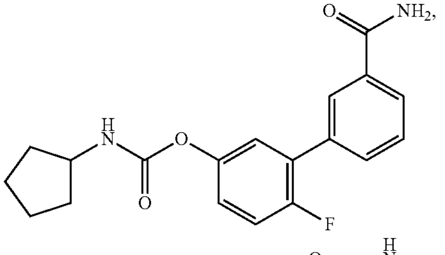
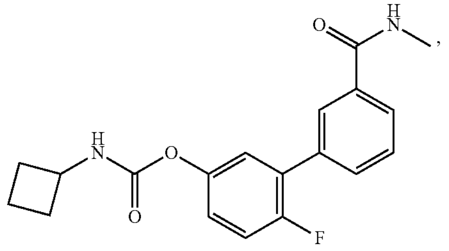
-continued
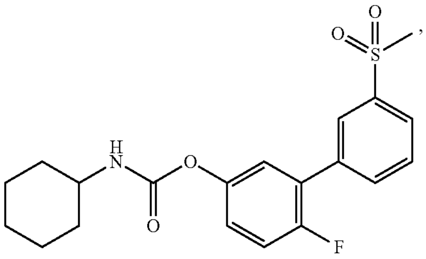
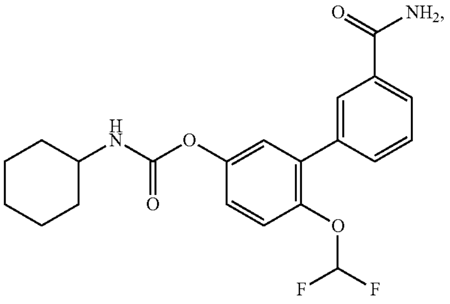
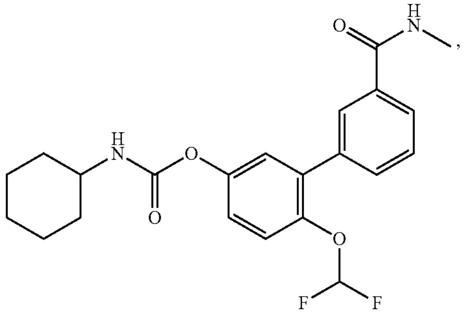
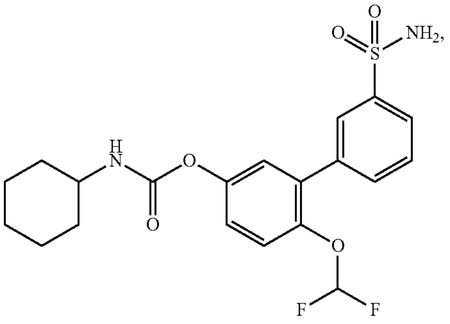
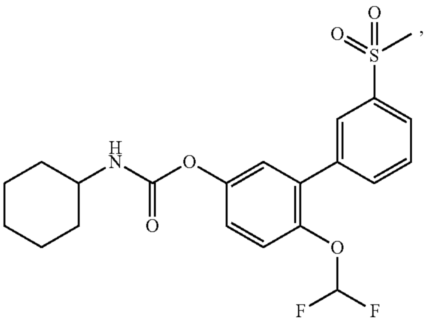

-continued
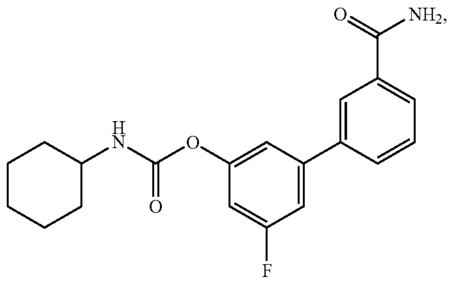
or
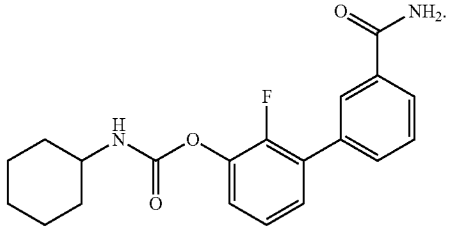
In embodiments, the compound is
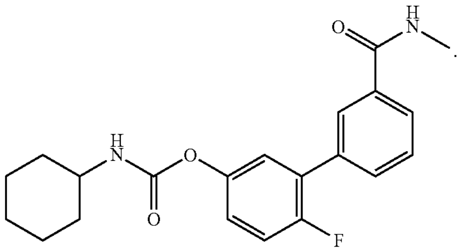 [SMILES: CNC(=O)c1cccc(-c2cc(OC(=O)NC3CCCCC3)ccc2F)c1]
In embodiments, the compound is
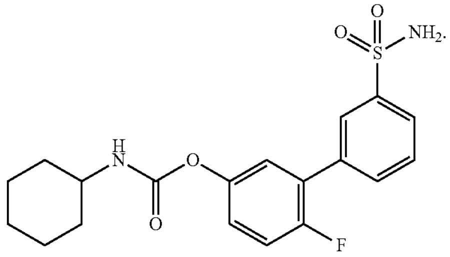 [SMILES: NS(=O)(=O)c1cccc(-c2cc(OC(=O)NC3CCCCC3)ccc2F)c1]
In embodiments, the compound is
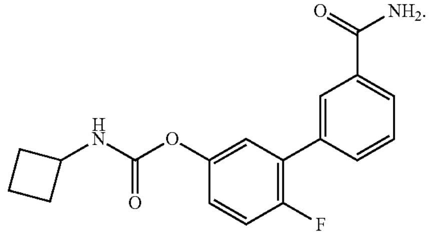 [SMILES: NC(=O)c1cccc(-c2cc(OC(=O)NC3CCC3)ccc2F)c1]
In embodiments, the compound is
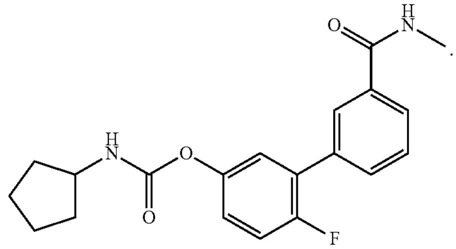 [SMILES: CNC(=O)c1cccc(-c2cc(OC(=O)NC3CCCC3)ccc2F)c1]
In embodiments, the compound is
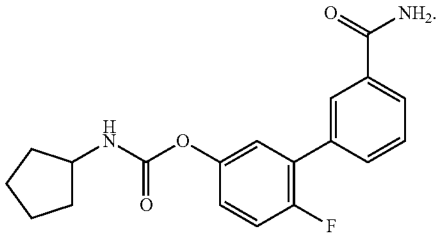 [SMILES: NC(=O)c1cccc(-c2cc(OC(=O)NC3CCCC3)ccc2F)c1]
In embodiments, the compound is
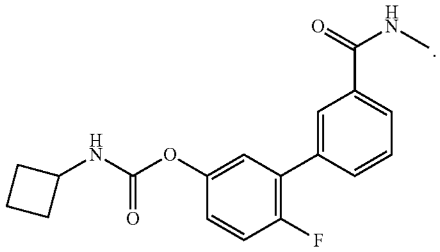 [SMILES: CNC(=O)c1cccc(-c2cc(OC(=O)NC3CCC3)ccc2F)c1]
In embodiments, the compound is
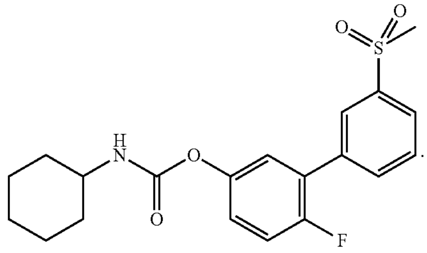 [SMILES: CS(=O)(=O)c1cccc(-c2cc(OC(=O)NC3CCCCC3)ccc2F)c1]
In embodiments, the compound is
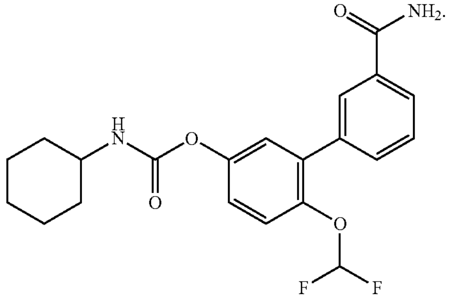 [SMILES: NC(=O)c1cccc(-c2cc(OC(=O)NC3CCCCC3)ccc2OC(F)F)c1]

In embodiments, the compound is

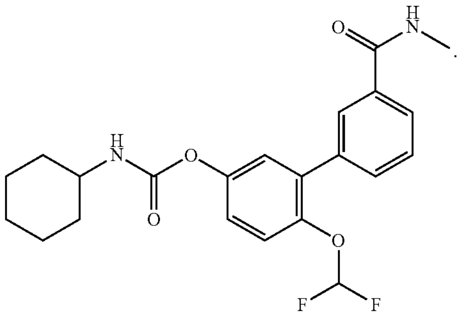 [SMILES: CNC(=O)c1cccc(-c2cc(OC(=O)NC3CCCCC3)ccc2OC(F)F)c1]

In embodiments, the compound is

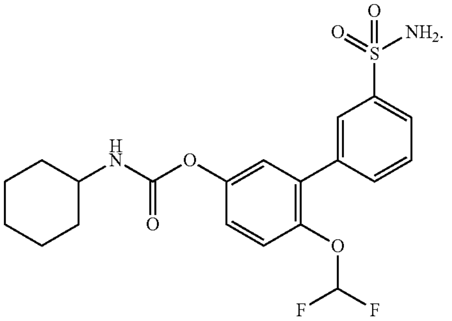 [SMILES: NS(=O)(=O)c1cccc(-c2cc(OC(=O)NC3CCCCC3)ccc2OC(F)F)c1]

In embodiments, the compound is

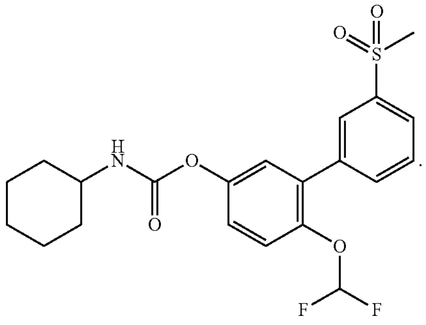 [SMILES: CS(=O)(=O)c1cccc(-c2cc(OC(=O)NC3CCCCC3)ccc2OC(F)F)c1]

In embodiments, the compound is

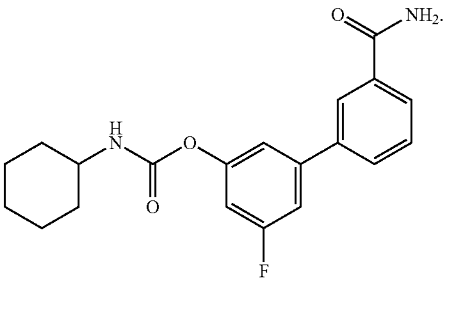 [SMILES: NC(=O)c1cccc(-c2cc(F)cc(OC(=O)NC3CCCCC3)c2)c1]

In embodiments, the compound is

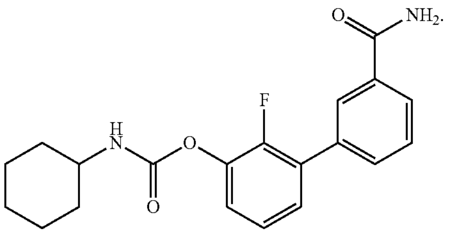 [SMILES: NC(=O)c1cccc(-c2cccc(OC(=O)NC3CCCCC3)c2F)c1]

In embodiments, the compound is [4-fluoro-3-[3-(methylcarbamoyl)phenyl]phenyl] N-cyclohexylcarbamate. In embodiments, the compound is [4-fluoro-3-(3-sulfamoylphenyl)phenyl] N-cyclohexylcarbamate. In embodiments, the compound is [3-(3-carbamoylphenyl)-4-fluoro-phenyl] N-cyclobutylcarbamate. In embodiments, the compound is [4-fluoro-3-[3-(methylcarbamoyl)phenyl]phenyl] N-cyclopentylcarbamate. In embodiments, the compound is [3-(3-carbamoylphenyl)-4-fluoro-phenyl] N-cyclopentylcarbamate. In embodiments, the compound is [4-fluoro-3-[3-(methylcarbamoyl)phenyl]phenyl] N-cyclobutylcarbamate. In embodiments, the compound is [4-fluoro-3-(3-methylsulfonylphenyl)phenyl] N-cyclohexylcarbamate. In embodiments, the compound is [3-(3-carbamoylphenyl)-4-(difluoromethoxy)phenyl] N-cyclohexylcarbamate. In embodiments, the compound is [4-(difluoromethoxy)-3-[3-(methylcarbamoyl)phenyl]phenyl] N-cyclohexylcarbamate. In embodiments, the compound is [4-(difluoromethoxy)-3-(3-sulfamoylphenyl)phenyl] N-cyclohexylcarbamate. In embodiments, the compound is [4-(difluoromethoxy)-3-(3-methylsulfonylphenyl)phenyl] N-cyclohexylcarbamate. In embodiments, the compound is [3-(3-carbamoylphenyl)-5-fluoro-phenyl] N-cyclohexylcarbamate. In embodiments, the compound is [3-(3-carbamoylphenyl)-2-fluoro-phenyl] N-cyclohexylcarbamate.

In another aspect is provided a compound of Formula (I)

(I)

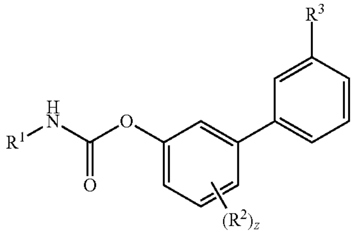

wherein $R^1$ is a cycloalkyl group; $R^3$ is $SO_2NR^4R^5$, $CONR^4R^5$, or $SO_2R^6$, where $R^4$ and $R^5$ can be, independently, hydrogen, alkyl or $R^4$ and $R^5$ together with the N atom to which they are connected may form a 4- to 6-membered ring, and $R^6$ is an alkyl group; z is an integer selected from 1 or 2; $R^2$ is F or $OCHF_2$, and can be attached to any position of the ring with the proviso that when $R^1$ is cyclohexyl, $R^3$ is $CONH_2$, z is 1 and $R^2$ is F, then $R^2$ is not attached in position para to the carbamate.

In an embodiment, the compound includes: $R^1$ is cyclobutyl, cyclopentyl, or cyclohexyl; $R^3$ is $SO_2NH_2$, $SO_2NHMe$, $SO_2NMe_2$, $CONH_2$, CONHMe, $CONMe_2$, or $SO_2Me$; z is 1; $R^2$ is F or $OCHF_2$ and can be attached to any position of the ring; with the proviso that when $R^1$ is cyclohexyl, $R^3$ is $CONH_2$ and $R^2$ is F, then $R^2$ is not attached in position para to the carbamate.

In an embodiment, the compound includes: $R^1$ is cyclobutyl, cyclopentyl or cyclohexyl; $R^3$ is $SO_2NH_2$, $SO_2NHMe$, $SO_2NMe_2$, $CONH_2$, CONHMe, $CONMe_2$, or $SO_2Me$; z is 1; $R^2$ is F or $OCHF_2$ and is attached in position para to the carbamate, with the proviso that when $R^1$ is cyclohexyl and $R^3$ is $CONH_2$, then $R^2$ is not F.

In embodiments, the compound is described in an aspect, embodiment, example, figure, table, drawing, or claim herein.

In embodiments, the compound modulates (e.g., decreases, inhibits) the level of activity of FAAH. In embodiments, the compound is a FAAH inhibitor. In embodiments, the compound is peripherally restricted (i.e., reduced concentration in the brain relative to outside the brain, reduced concentration in the brain relative to in circulation, reduced concentration immediately inside the blood brain barrier relative to immediately outside the blood brain barrier).

In embodiments, the compound has an oral bioavailability of greater than 35% in a subject. In embodiments, the compound has an oral bioavailability of greater than 45% in a subject. In embodiments, the compound has an oral bioavailability of greater than 55% in a subject. In embodiments, the compound has an oral bioavailability of greater than 65% in a subject. In embodiments, the compound has an oral bioavailability of greater than 75% in a subject. In embodiments, the compound has an oral bioavailability of greater than 85% in a subject. In embodiments, the compound has an oral bioavailability of greater than 95% in a subject.

In an aspect is provided a compound having the formula:

(I)

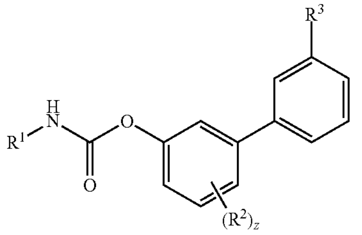

or a pharmaceutically acceptable salt thereof, wherein $R^1$ is substituted or unsubstituted cycloalkyl, substituted or unsubstituted heterocycloalkyl, substituted or unsubstituted aryl, or substituted or unsubstituted heteroaryl (e.g., unsubstituted cyclohexyl); $R^2$ is —OH or a physiologically hydrolyzable ester thereof (e.g., —OH); and (a) $R^3$ is $—SO_2R^6$ or $—SO_2NR^4R^5$ and $R^4$, $R^5$, and $R^6$ are independently hydrogen, substituted or unsubstituted $C_1$-$C_8$ alkyl or substituted or unsubstituted 2 to 8 membered heteroalkyl (e.g., $R^4$ and $R^5$ are H, $R^4$ is H and $R^5$ is $—CH_3$, or $R^6$ is $—CH_3$); or (b) $R^3$ is $—C(O)NR^4R^5$ and $R^4$ is independently hydrogen, substituted or unsubstituted $C_1$-$C_8$ alkyl or substituted or unsubstituted 2 to 8 membered heteroalkyl and $R^5$ is substituted or unsubstituted $C_1$-$C_8$ alkyl or substituted or unsubstituted 2 to 8 membered heteroalkyl (e.g., $R^4$ is H and $R^5$ is $—CH_3$). $R^4$ and $R^5$ may optionally be joined to form a substituted or unsubstituted 4 to 8 membered heterocycloalkyl or substituted or unsubstituted 5 to 6 membered heteroaryl. The symbol z is 1. The symbol X is —F, —Cl, —Br, or —I. In embodiments, the compound may have a formula described herein (e.g., $R^2$ is para to the carbamate-$R^1$ and ortho to the phenyl).

In embodiments, a compound described herein is not

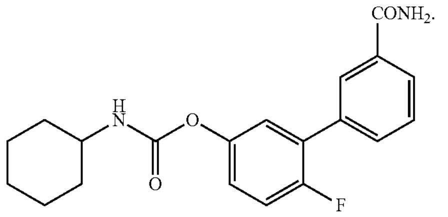 [SMILES: NC(=O)c1cccc(-c2cc(OC(=O)NC3CCCCC3)ccc2F)c1]

In embodiments, a compound described herein is not

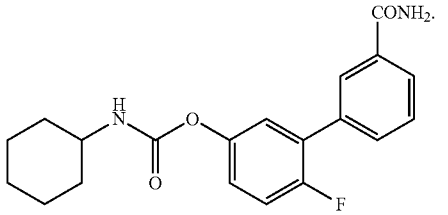 [SMILES: NC(=O)c1cccc(-c2cc(OC(=O)NC3CCCCC3)ccc2F)c1]

In embodiments, a compound described herein is not

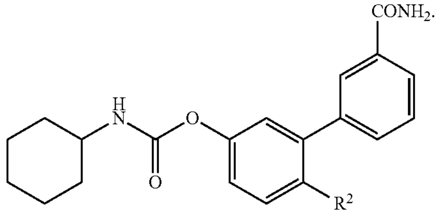

In embodiments, a compound described herein is not

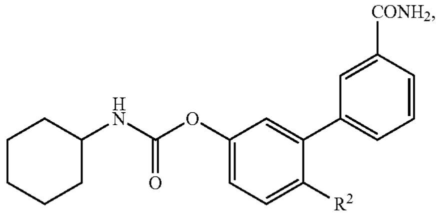

wherein $R^2$ is halogen, $—CX_3$, $—OCX_3$, $—OCHX_2$, substituted or unsubstituted $C_1$-$C_8$ alkyl, or substituted or unsubstituted 2 to 8 membered heteroalkyl. In embodiments, a compound described herein is not

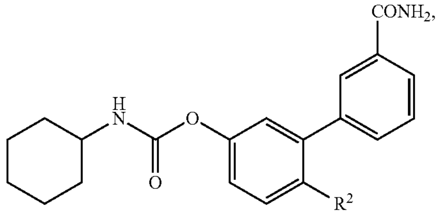

wherein $R^2$ is halogen, $—CX_3$, $—OCX_3$, $—OCHX_2$, substituted or unsubstituted $C_1$-$C_4$ alkyl, or substituted or unsubstituted 2 to 4 membered heteroalkyl. In embodiments, a compound described herein is not

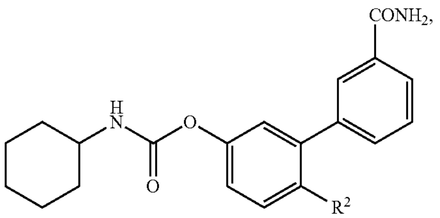

wherein $R^2$ is halogen, $-CX_3$, $-OCX_3$, or $-OCHX_2$. In embodiments, a compound described herein is not

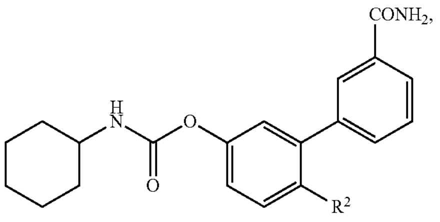

wherein $R^2$ is halogen or $-OCHX_2$. In embodiments, a compound described herein is not

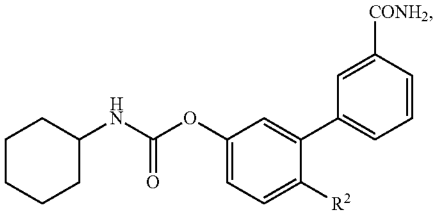

wherein $R^2$ is $-OCHX_2$. In embodiments, a compound described herein is not

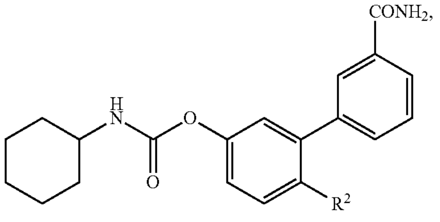

wherein $R^2$ is halogen.

In embodiments, the compound is not a compound having the formula:

(Iz)

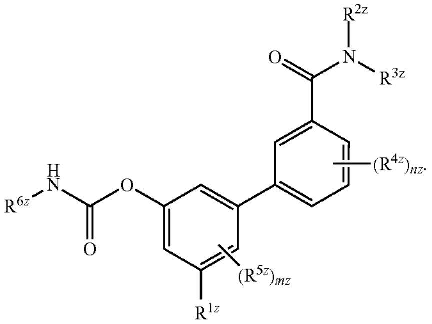

or a pharmaceutically acceptable salts thereof. In Formula Iz, $R^{1z}$ is hydrogen, hydroxy or the physiologically hydrolyzable esters thereof, —SH, carboxy or the physiologically hydrolysable esters thereof, hydroxy $(C_1\text{-}C_3)$alkyl (e.g., $-CH_2OH$ or $-CH_2CH_2OH$) or the physiologically hydrolyzable esters thereof, $-NR^{7z}R^{8z}$, or $-NHSO_2R^{9z}$. In Formula Iz, $R^{7z}$ and $R^{8z}$ are independently hydrogen or $(C_1\text{-}C_3)$ alkyl. In Formula Iz, $R^{9z}$ is hydrogen, methyl, ethyl, trifluoromethyl or trifluoroethyl. In Formula Iz, $R^{2z}$ and $R^{3z}$ are independently hydrogen or substituted or unsubstituted $(C_1\text{-}C_3)$alkyl. In Formula Iz, each $R^{4z}$ is independently a hydrogen, a substituted or unsubstituted $(C_1\text{-}C_3)$alkyl. In Formula Iz, $n^z$ is an integer from 0 to 4. In Formula Iz, $R^{5z}$ is independently hydrogen, halogen, hydroxy or the physiologically hydrolyzable esters thereof, carboxy or the physiologically hydrolysable esters thereof, hydroxyl-$(C_1\text{-}C_3)$ alkyl or the physiologically hydrolyzable esters thereof, $-(C_1\text{-}C_3)$alkoxy, or $-NR^{20z}R^{21z}$. In Formula Iz, $R^{20z}$ and $R^{21z}$ are independently hydrogen or $(C_1\text{-}C_3)$alkyl. In Formula Iz, $m^z$ is an integer from 0 to 3. In Formula Iz, $R^{6z}$ is an unsubstituted or substituted cyclohexyl, cyclopentyl, cyclobutyl or tetrahydropyran-4-yl.

In embodiments of formula Iz, $m^z$ and $n^z$ are each 0, and $R^{2z}$ and $R^{3z}$ are each H. In embodiments of formula Iz, $R^{1z}$ is hydroxy, carboxy, or hydroxymethyl. In embodiments of formula Iz, $R^{1z}$ hydrogen. In embodiments of formula Iz, $R^{1z}$ is hydroxy or the physiologically hydrolyzable esters thereof. In embodiments of formula Iz, $R^{1z}$ is —SH. In embodiments of formula Iz, $R^{1z}$ is carboxy or the physiologically hydrolysable esters thereof. In embodiments of formula Iz, $R^{1z}$ is hydroxyl-$(C_1\text{-}C_3)$alkyl. In embodiments of formula Iz, $R^{1z}$ is $-CH_2OH$ or $-CH_2CH_2OH$ or the physiologically hydrolyzable esters thereof. In embodiments of formula Iz, $R^{1z}$ is $-NR^{7z}R^{8z}$. In embodiments of formula Iz, $R^{1z}$ is $-NHSO_2R^{9z}$. In embodiments of formula Iz, $R^{7z}$ and $R^{8z}$ are independently hydrogen or $(C_1\text{-}C_3)$alkyl. In embodiments of formula Iz, $R^{7z}$ and $R^{8z}$ are independently methyl, ethyl, propyl, isopropyl, butyl, t-butyl, isobutyl, n-butyl, pentyl, hexyl, heptyl, or octyl. In embodiments of formula Iz, $R^{9z}$ is hydrogen, methyl, ethyl, trifluoromethyl or trifluoroethyl.

In embodiments of formula Iz, $R^{6z}$ is substituted or unsubstituted. In embodiments of formula Iz, $R^{6z}$ is cyclohexyl. In embodiments of formula Iz, the cyclohexyl is unsubstituted. In embodiments of formula Iz, the compound is a physiologically acceptable ester of any of the embodiments of the compound of formula Iz. In embodiments of formula Iz, $R^{7z}$ and $R^{8z}$ are each H and $R^{9z}$ is methyl, ethyl, trifluoromethyl or trifluoroethyl.

In embodiments of formula Iz, $m^z$ is 0 and $n^z$ is 0, 1, 2, 3, or 4. In embodiments of formula Iz, $m^z$ is 1 and $n^z$ is 0, 1, 2, 3, or 4. In embodiments of formula Iz, $m^z$ is 2 and $n^z$ is 0, 1, 2, 3, or 4. In embodiments of formula Iz, $m^z$ is 3, and $n^z$ is 0, 1, 2, 3, or 4. In embodiments of formula Iz, the sum of $m^z$ and $n^z$ is 0, 1, 2, or 3. In embodiments of formula Iz, each $R^{1z}$, $R^{2z}$, $R^{3z}$, $R^{4z}$, $R^{6z}$, $R^{7z}$, and $R^{8z}$ member is also unsubstituted.

In embodiments of formula Iz, $R^{1z}$ is hydroxy or a hydroxy($C_1$-$C_3$)alkyl group or a physiologically hydrolysable ester of the hydroxyl or hydroxy($C_1$-$C_3$)alkyl group. In embodiments of formula Iz, $R^{1z}$ has the formula —OC(O)$R^{10z}$, —(O)COR$^{10z}$, —$CH_2$OC(O)$R^{10z}$, —$CH_2$(O)COR$^{10z}$, —$CH_2CH_2$OC(O)$R^{10z}$, $CH_2CH_2$(O)COR$^{10z}$, —CH($CH_3$)(O)COR$^{10z}$), —CH($CH_3$)(O)COR$^{10z}$. In embodiments of formula Iz, $R^{10z}$ is substituted or unsubstituted hydrocarbyl. In embodiments of formula Iz, $R^{10z}$ is substituted or unsubstituted alkyl, alkenyl, cycloalkyl, heteroalkyl, heterocycloalkyl, heteroalkenyl, heterocycloalkenyl, and cycloalkenyl. In embodiments of formula Iz, $R^{10z}$ is substituted or unsubstituted ($C_1$-$C_3$)alkyl. In embodiments of formula Iz, $R^{10z}$ is methyl, ethyl, propyl, or trifluoromethyl. In embodiments of formula Iz, $R^{10z}$ is a substituted or unsubstituted ($C_1$-$C_3$) hydrocarbyl selected from the group consisting of alkenyl, cycloalkyl, heteroalkyl, heterocycloalkyl, heteroalkenyl, heterocycloalkenyl, and cycloalkenyl. In embodiments of formula Iz, $m^z$ is 0 and $n^z$ is 0, 1, 2; $m^z$ is 1 and $n^z$ is 0, 1, or 2; or $m^z$ is 2 and $n^z$ is 0, 1, or 2.

In embodiments of formula Iz, in the case where $R^{1z}$ is a carboxy group or physiologically hydrolysable ester thereof, $R^{1z}$ is —$CO_2$H, or —$CO_2R^{10z}$ wherein $R^{10z}$ is substituted or unsubstituted hydrocarbyl, optionally, substituted or unsubstituted alkyl, alkenyl, cycloalkyl, heteroalkyl, heterocycloalkyl, heteroalkenyl, heterocycloalkenyl, or cycloalkenyl and still further optionally, substituted or unsubstituted ($C_1$-$C_3$)alkyl (e.g., methyl, ethyl, propyl, trifluoromethyl) or a substituted or unsubstituted ($C_1$-$C_3$) hydrocarbyl selected from alkenyl, cycloalkyl, heteroalkyl, heterocycloalkyl, heteroalkenyl, heterocycloalkenyl, and cycloalkenyl. In embodiments of formula Iz, $m^z$ is 0 and $n^z$ is 0, 1, 2; $m^z$ is 1 and $n^z$ is 0, 1, or 2; or $m^z$ is 2 and $n^z$ is 0, 1, or 2.

In embodiments of formula Iz, $R^{2z}$ and $R^{3z}$ are hydrogen. In embodiments of formula Iz, $m^z$ is 0 and $n^z$ is 0, 1, or 2; $m^z$ is 1 and $n^z$ is 0, 1, or 2; or $m^z$ is 2 and $n^z$ is 0, 1, or 2. In embodiments of formula Iz, $m^z$ is 0 and $n^z$ is 0, 1, 2; $m^z$ is 1 and $n^z$ is 0, 1, or 2; or $m^z$ is 2 and $n^z$ is 0, 1, or 2.

In embodiments of formula Iz, $R^{1z}$ is hydroxy and at least one of $R^{2z}$ and $R^{3z}$ is hydrogen. In embodiments of formula Iz, both of $R^{2z}$ and $R^{3z}$ are hydrogen. In embodiments of formula Iz, in which $R^{1z}$ is hydroxy, $R^{2z}$ and $R^{3z}$ are independently selected from substituted or unsubstituted ($C_1$-$C_3$)alkyl (e.g., methyl, ethyl, propyl), and H. In embodiments of formula Iz, $m^z$ is 0 and $n^z$ is 0, 1, 2; $m^z$ is 1 and $n^z$ is 0, 1, 2; or $m^z$ is 2 and $n^z$ is 0, 1, 2.

In embodiments of formula Iz, $R^{6z}$ is substituted or unsubstituted cyclohexyl. Substituents for the cyclohexyl include alkyl (e.g., methyl, ethyl), halo (F, Cl, I, Br and optionally F or Cl), and trifluoromethyl. In embodiments of formula Iz, $m^z$ is 0 and $n^z$ is 0, 1, 2; $m^z$ is 1 and $n^z$ is 0, 1, 2; or $m^z$ is 2 and $n^z$ is 0, 1, 2.

In embodiments of formula Iz, $R^{1z}$ is hydroxy or hydroxy ($C_1$-$C_3$)alkyl or a physiologically hydrolyzable ester thereof in which the hydrolysis releases the corresponding compound wherein $R^{1z}$ is hydroxyl or hydroxy($C_1$-$C_3$)alkyl, $R^{6z}$ is unsubstituted cyclohexyl, $m^z$ is 0 and $n^z$ is 0, 1, or 2; or $m^z$ is 1 and $n^z$ is 0, 1, or 2, or $m^z$ is 2 and $n^z$ is 0, 1, or 2. In embodiments of formula Iz, $R^{2z}$ and $R^{3z}$ are each H. In embodiments of formula Iz, the ester is of the formula —OC(O)$R^{10z}$ wherein $R^{10z}$ is substituted or unsubstituted hydrocarbyl, optionally, substituted or unsubstituted alkyl, alkenyl, cycloalkyl, heteroalkyl, heterocycloalkyl, heteroalkenyl, heterocycloalkenyl, and cycloalkenyl and still further optionally, substituted or unsubstituted ($C_1$-$C_3$)alkyl (e.g., methyl, ethyl, propyl, trifluoromethyl) or a substituted or unsubstituted ($C_1$-$C_3$) hydrocarbyl selected from alkenyl, cycloalkyl, heteroalkyl, heterocycloalkyl, heteroalkenyl, heterocycloalkenyl, and cycoalkenyl. In embodiments of formula Iz, $R^{10z}$ is unsubstituted hydrocarbyl, unsubstituted alkyl, unsubstituted alkenyl, unsubstituted cycloalkyl, unsubstituted heteroalkyl, unsubstituted heterocycloalkyl, unsubstituted heteroalkenyl, unsubstituted heterocycloalkenyl, or unsubstituted cycloalkenyl; or unsubstituted ($C_1$-$C_3$)alkyl (e.g., methyl, ethyl, propyl, trifluoromethyl) or unsubstituted ($C_1$-$C_3$) hydrocarbyl selected from alkenyl, cycloalkyl, heteroalkyl, heterocycloalkyl, heteroalkenyl, heterocycloalkenyl, and cycloalkenyl.

In embodiments of formula Iz, $R^{5z}$ is independently hydrogen, halogen, hydroxy or the physiologically hydrolyzable esters thereof, carboxy or the physiologically hydrolysable esters thereof, hydroxyl-($C_1$-$C_3$)alkyl or the physiologically hydrolyzable esters thereof, —($C_1$-$C_3$)alkoxy, or $NR^{20z}R^{21z}$; and $R^{20z}$ and $R^{21z}$ are independently hydrogen or ($C_1$-$C_3$)alkyl. In embodiments of formula Iz, $R^{5z}$ is independently hydrogen or halogen. In embodiments of formula Iz, $R^{5z}$ is independently hydrogen, halogen, or hydroxy or the physiologically hydrolyzable esters thereof. In embodiments of formula Iz, $R^{5z}$ is independently hydroxy or the physiologically hydrolyzable esters thereof, carboxy or the physiologically hydrolysable esters thereof, hydroxyl-($C_1$-$C_3$)alkyl or the physiologically hydrolyzable esters thereof, or —($C_1$-$C_3$)alkoxy. In embodiments of formula Iz, $R^{5z}$ is hydroxy or the physiologically hydrolyzable esters thereof. In embodiments of formula Iz, $R^{5z}$ is carboxy or the physiologically hydrolysable esters thereof. In embodiments of formula Iz, $R^{5z}$ is hydroxyl-($C_1$-$C_3$)alkyl or the physiologically hydrolyzable esters thereof. In embodiments of formula Iz, $R^{5z}$ is —($C_1$-$C_3$)alkoxy. In embodiments of formula Iz, $R^{5z}$ is $NR^{20z}R^{21z}$ and $R^{20z}$ and $R^{21z}$ are independently hydrogen or ($C_1$-$C_3$)alkyl. In embodiments of formula Iz, $R^{5z}$ is $NR^{20z}R^{21z}$ and $R^{20z}$ and $R^{21z}$ are hydrogen. In embodiments of formula Iz, $R^{5z}$ is as described herein and $m^z$ is 1.

In embodiments of formula Iz, $R^{5z}$ is independently —($C_1$-$C_3$)alkoxy or —$NR^{20z}R^{21z}$; and $R^{20z}$ and $R^{21z}$ are independently hydrogen or ($C_1$-$C_3$)alkyl. In embodiments of formula Iz, $R^{5z}$ is independently hydrogen, halogen, hydroxy or the physiologically hydrolyzable esters thereof, or carboxy or the physiologically hydrolysable esters thereof. In embodiments of formula Iz, $R^{5z}$ is independently hydrogen, hydroxy or the physiologically hydrolyzable esters thereof, carboxy or the physiologically hydrolysable esters thereof, or hydroxyl-($C_1$-$C_3$)alkyl or the physiologically hydrolyzable esters thereof.

In embodiments of formula Iz, $R^{5z}$ is hydroxyl. In embodiments of formula Iz, $R^{5z}$ is hydroxyl and $m^z$ is 1. In embodiments of formula Iz, $R^{5z}$ is COOH. In embodiments of formula Iz, $R^{5z}$ is COOH and $m^z$ is 1. In embodiments of formula Iz, $R^{5z}$ is $CH_2OH$. In embodiments of formula Iz, $R^{5z}$ is $CH_2OH$ and $m^z$ is 1. In embodiments of formula Iz, $R^{5z}$ is $OCH_3$. In embodiments of formula Iz, $R^{5z}$ is $OCH_3$ and $m^z$ is 1. In embodiments of formula Iz, $R^{5z}$ is $CH_3$. In embodiments of formula Iz, $R^{5z}$ is $CH_3$ and $m^z$ is 1. In embodiments of formula Iz, $R^{5z}$ is F. In embodiments of formula Iz, $R^{5z}$ is F and $m^z$ is 1. In embodiments of formula Iz, $R^{5z}$ is $NH_2$. In embodiments of formula Iz, $R^{5z}$ is $NH_2$ and $m^z$ is 1.

In embodiments of formula Iz, the compound is one of:

1

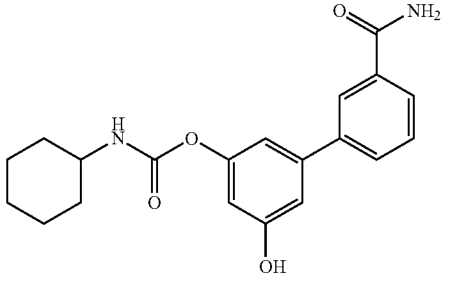

2

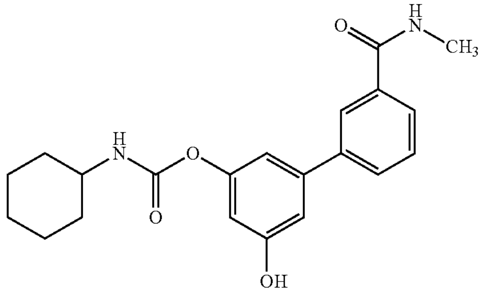

3

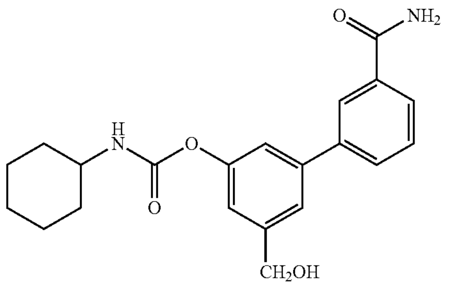

4

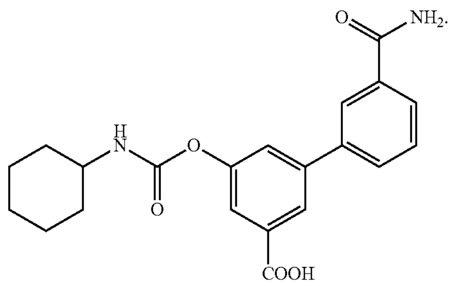

In embodiments of formula Iz, the compound is a compound immediately above provided as a physiologically hydrolysable ester as described herein.

In embodiments of formula Iz, the compound is:

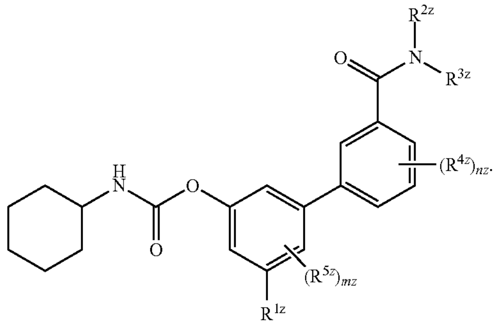

In embodiments of formula Iz, the compound is:

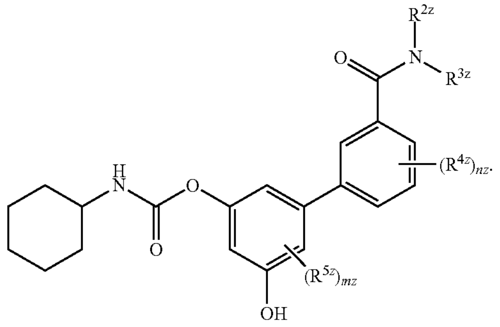

In embodiments of formula Iz, the compound is:

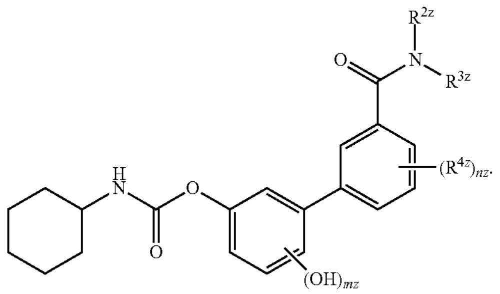

In embodiments of formula Iz, the compound is:

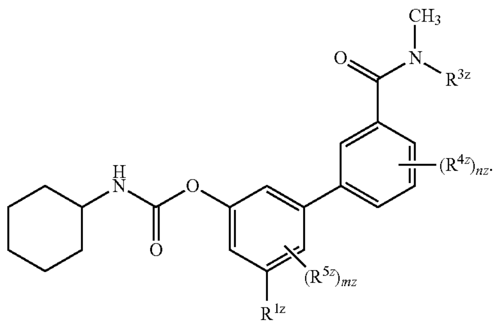

In embodiments of formula Iz, the compound is:
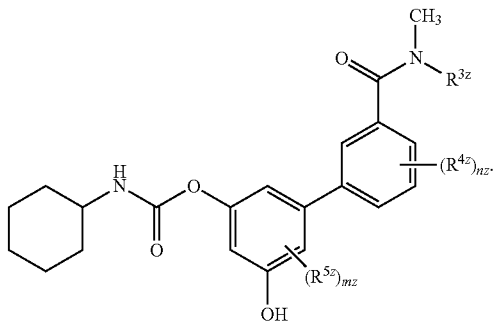
In embodiments of formula Iz, the compound is:
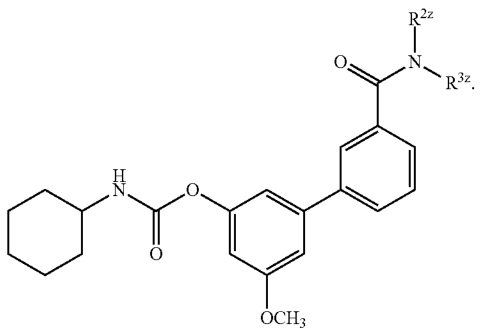
In embodiments of formula Iz, the compound is:
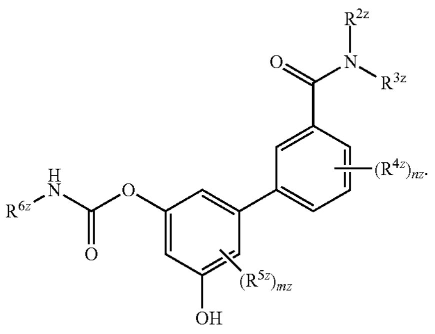
In embodiments of formula Iz, the compound is:
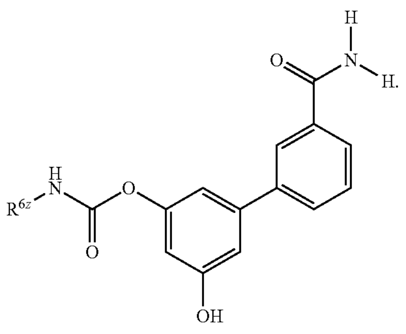
In embodiments of formula Iz, the compound is:
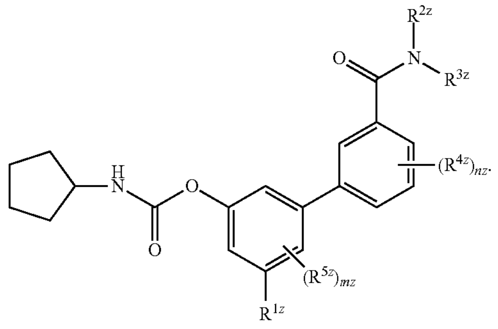
In embodiments of formula Iz, the compound is:
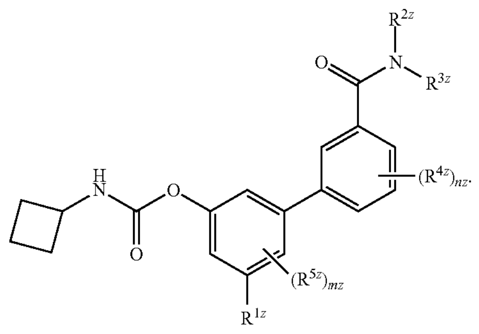
In embodiments of formula Iz, the compound is:
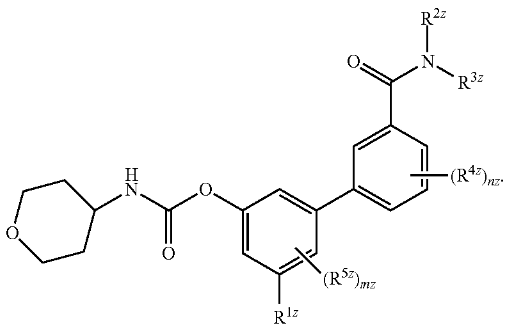
In embodiments of formula Iz, the compound is:
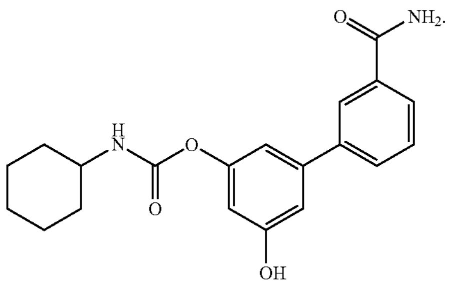 [SMILES: NC(=O)c1cccc(-c2cc(O)cc(OC(=O)NC3CCCCC3)c2)c1]

In embodiments of formula Iz, the compound is:
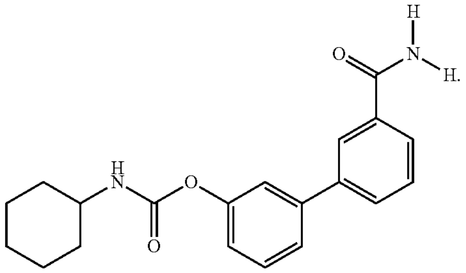
In embodiments of formula Iz, the compound is:
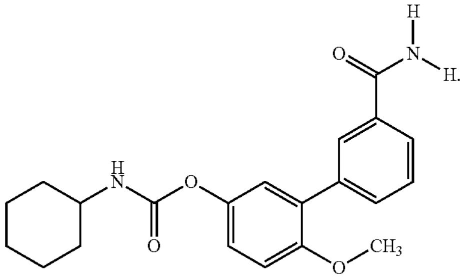
In embodiments of formula Iz, the compound is:
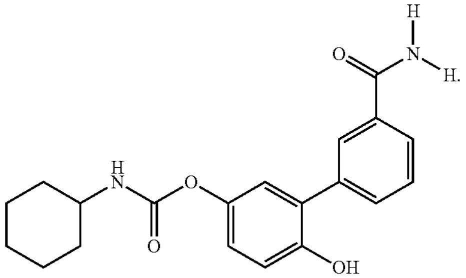
In embodiments of formula Iz, the compound is:
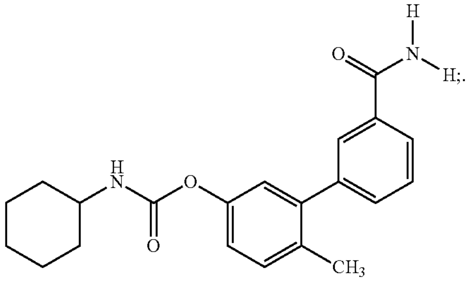
In embodiments of formula Iz, the compound is:
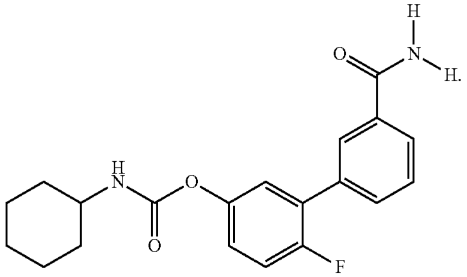
In embodiments of formula Iz, the compound is:
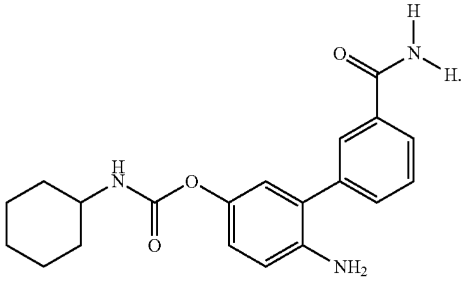
In embodiments of formula Iz, the compound is:
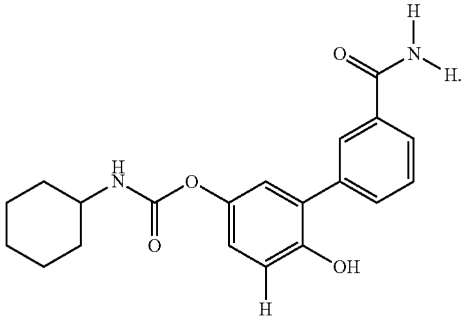
In embodiments of formula Iz, the compound is:
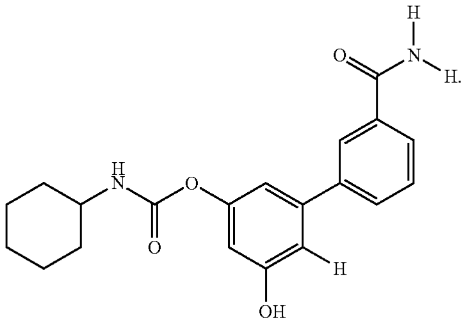

In embodiments of formula Iz, the compound is

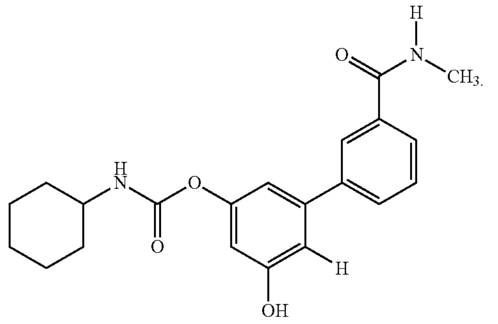 [SMILES: CNC(=O)c1cccc(-c2cc(O)cc(OC(=O)NC3CCCCC3)c2)c1]

In embodiments of formula Iz, the compound is:

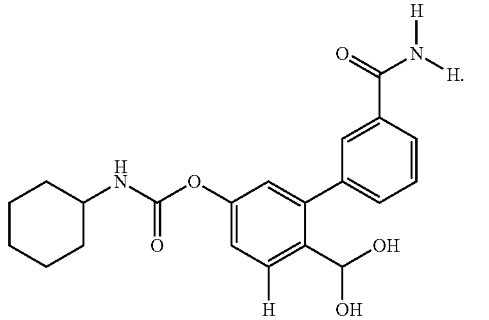

In embodiments of formula Iz, the compound is:

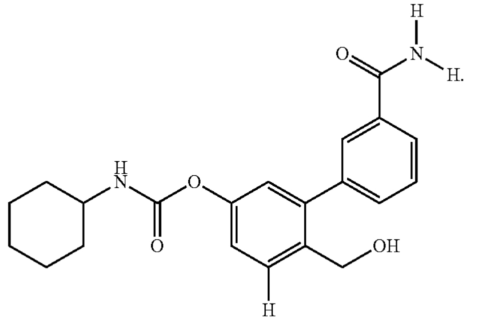

In embodiments of formula Iz, the compound is:

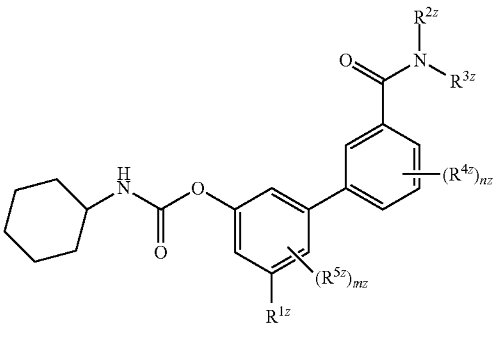

wherein $R^{1z}$, $R^{2z}$, $R^{3z}$, and $R^{4z}$ are hydrogen, $R^{5z}$ is —OH, $m^z$ is 1, and $n^z$ is 0. In embodiments, the compound is not a compound of an embodiment of the compound of formula Iz. In embodiments, the compound is not a compound of an embodiment of the compound of formula Iz, as described herein.

As used to describe compounds of formula Iy or Iz, the term "hydrocarbyl" refers to a ($C_1$-$C_8$ hydrocarbon radical that is a ($C_1$-$C_8$)alkyl, ($C_1$-$C_8$)alkenyl, ($C_3$-$C_8$)cycloalkyl, ($C_3$-$C_8$)cycloalkenyl, ($C_1$-$C_8$)heteroalkyl, ($C_1$-$C_8$)heteroalkenyl, ($C_3$-$C_8$)heterocycloalkyl, or ($C_3$-$C_8$)heterocycloalkenyl radical. More preferably, the hydrocarbyl in each instance is a substituted or unsubstituted ($C_1$ to $C_6$), ($C_1$ to $C_3$), or ($C_1$ to $C_2$)hydrocarbyl, and more preferably still an unsubstituted ($C_1$ to $C_3$)alkyl. Still more preferably the hydrocarbyl in each instance is methyl or ethyl or trifluoromethyl. The term "hydrocarbyl" also includes those groups having up to 1, 2, or 3 atoms of a hydrocarbyl group as set forth above replaced by a heteroatom with the proviso that the heteroatoms of the hydrocarbyl are not contiguous to each other and the hydrocarbyl is not attached to the remainder of the compound by a heteroatom of the hydrocarbyl.

As used to describe compounds of formula Iy or Iz, a physiologically cleavable ester is one which is a substrate for carboxyesterases in vivo. Physiologically cleavable esters are typically rapidly hydrolyzed such that the concentration of the corresponding alcohol comes to exceed that of the ester in blood or plasma. For instance, a physiologically cleavable ester is one which is rapidly hydrolyzed to the corresponding alcohol and acid in vivo with a half time of less than ½, 1, 2 or 3 hours at a therapeutically relevant dosages.

In embodiments, the compound is not a compound having the formula:

(Iy)

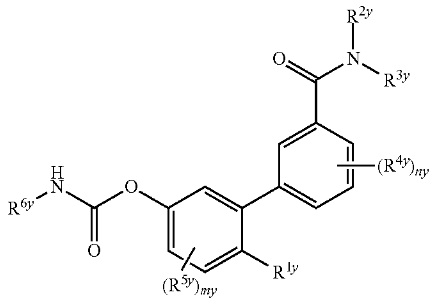

or the pharmaceutically acceptable salts thereof. In Formula Iy, $R^{1y}$ is a polar group. In embodiments of formula Iy, $R^{1y}$ is hydroxy or the physiologically hydrolysable esters thereof, —SH, —O-carboxamido, —OC(O)$R^{7y}$, —O—CO—$N^{8y}R^{9y}$ or —$NR^{8y}R^{9y}$. In Formula Iy, $R^{7y}$ is substituted or unsubstituted hydrocarbyl and $R^{8y}$ and $R^{9y}$ are independently hydrogen or substituted or unsubstituted hydrocarbyl. In Formula Iy, $R^{2y}$ and $R^{3y}$ are independently hydrogen or substituted or unsubstituted hydrocarbyl. In Formula Iy, each $R^{4y}$ is independently halogen or substituted or unsubstituted hydrocarbyl and $n^y$ is an integer from 0 to 4. In Formula Iy, each $R^{5y}$ is independently halo or substituted or unsubstituted hydrocarbyl and $m^y$ is an integer from 0 to 3. In Formula Iy, $R^{6y}$ is substituted or unsubstituted cyclohexyl.

In embodiments of formula Iy, each of $R^{2y}$, $R^{3y}$, $R^{7y}$, $R^{8y}$, and $R^{9y}$ are independently selected from hydrogen and unsubstituted hydrocarbyl. In embodiments of formula Iy, each of $R^{2y}$, $R^{3y}$, $R^{7y}$, $R^{8y}$, and $R^{9y}$ are independently hydrogen or unsubstituted $C_1$ to $C_3$ hydrocarbyl. In embodiments of formula Iy, each $R^{4y}$ and $R^{5y}$ member are independently halogen or $C_1$ to $C_3$ hydrocarbyl. In embodiments of formula Iy, the compounds having formula Iy, and embodiments thereof, are peripherally restricted.

In embodiments of formula Iy, $m^y$ is 0 and $n^y$ is 0, 1, 2, 3, or 4. In embodiments of formula Iy, $m^y$ is 1 and $n^y$ is 0, 1, 2, 3, or 4. In embodiments of formula Iy, $m^y$ is 2 and $n^y$ is 0, 1, 2, 3, or 4. In embodiments of formula Iy, $m^y$ is 3, and $n^y$ is 0, 1, 2, 3, or 4. In embodiments of formula Iy, the sum of $m^y$ and $n^y$ is 0, 1, 2, or 3. In embodiments of formula Iy, each hydrocarbyl member is unsubstituted.

In embodiments of formula Iy, $R^{1y}$ is hydroxy or a physiologically hydrolysable ester of the hydroxy. In embodiments of formula Iy, these esters include those of the formula —OC(O)$R^{7y}$ wherein $R^{7y}$ is substituted or unsubstituted hydrocarbyl, optionally, substituted or unsubstituted alkyl, alkenyl, cycloalkyl, heteroalkyl, heterocycloalkyl, heteroalkenyl, heterocycloalkenyl, or cycloalkenyl and further optionally, substituted or unsubstituted ($C_1$-$C_3$)alkyl (e.g., methyl, ethyl, propyl, trifluoromethyl) or a substituted or unsubstituted ($C_1$-$C_3$) hydrocarbyl selected from alkenyl, cycloalkyl, heteroalkyl, heterocycloalkyl, heteroalkenyl, heterocycloalkenyl, and cycloalkenyl. In embodiments of formula Iy, $m^y$ is 0 and $n^y$ is 0, 1, 2; $m^y$ is 1 and $n^y$ is 0, 1, or 2; or $m^y$ is 2 and $n^y$ is 0, 1, or 2.

In embodiments of formula Iy, $R^{2y}$ and $R^{3y}$ are hydrogen or a substituted or unsubstituted ($C_1$-$C_3$)hydrocarbyl selected from alkyl, alkenyl, cycloalkyl, heteroalkyl, heterocycloalkyl, heteroalkenyl, heterocycloalkenyl, and cycoalkenyl. In embodiments of formula Iy, $m^y$ is 0 and $n^y$ is 0, 1, or 2; $m^y$ is 1 and $n^y$ is 0, 1, or 2; or $m^y$ is 2 and $N^y$ is 0, 1, or 2. In embodiments of formula Iy, at least one or both of $R^{2y}$ and $R^{3y}$ is hydrogen. In embodiments of formula Iy, $m^y$ is 0 and $n^y$ is 0, 1, 2; $M^y$ is 1 and $n^y$ is 0, 1, or 2; or $m^y$ is 2 and $n^y$ is 0, 1, or 2. In embodiments of formula Iy, the $R^2$ and/or $R^{2y}$ hydrocarbyl member is unsubstituted.

In embodiments of formula Iy, $R^{1y}$ is hydroxy and at least one of $R^{2y}$ and $R^{3y}$ is hydrogen. In embodiments of formula Iy, both of $R^{2y}$ and $R^{3y}$ are hydrogen. In embodiments of formula Iy, in which $R^{1y}$ is hydroxy, $R^{2y}$ and $R^{3y}$ are independently substituted or unsubstituted ($C_1$-$C_3$)alkyl (e.g., methyl, ethyl, propyl), or H. In embodiments of formula Iy, $m^y$ is 0 and $n^y$ is 0, 1, 2; $m^y$ is 1 and $n^y$ is 0, 1, 2; or $m^y$ is 2 and $n^y$ is 0, 1, 2.

In embodiments of formula Iy, $R^{6y}$ is substituted or unsubstituted cyclohexyl. In embodiments of formula Iy, substituents for the cyclohexyl include alkyl (e.g., methyl, ethyl), halo (F, Cl, I, Br or optionally F or Cl), or trifluoromethyl. In embodiments of formula Iy, $m^y$ is 0 and $n^y$ is 0, 1, 2; $m^y$ is 1 and $n^y$ is 0, 1, 2; or $m^y$ is 2 and $n^y$ is 0, 1, 2.

In embodiments of formula Iy, $R^{4y}$ is substituted or unsubstituted alkyl, alkenyl, cycloalkyl, heteroalkyl, heterocycloalkyl, heteroalkenyl, heterocycloalkenyl, or cycloalkenyl and optionally, substituted or unsubstituted ($C_1$-$C_3$) alkyl (e.g., methyl, ethyl, propyl, trifluoromethyl) or a substituted or unsubstituted ($C_1$-$C_3$) hydrocarbyl selected from alkenyl, cycloalkyl, heteroalkyl, heterocycloalkyl, heteroalkenyl, heterocycloalkenyl, and cycoalkenyl. In embodiments of formula Iy, $R^{4y}$ is selected from ($C_1$-$C_3$) alkyl (e.g., methyl, ethyl, propyl), and $n^y$ is 0, 1, 2, or 3. In embodiments of formula Iy, each $R^{4y}$ is halogen or haloalkyl (e.g., trifluoromethyl). In embodiments of formula Iy, each $R^{4y}$ is halogen or unsubstituted ($C_1$-$C_3$)alkyl (e.g., methyl, ethyl, propyl). In embodiments of formula Iy, $m^y$ is 0 or 1.

In embodiments of formula Iy, $R^{5y}$ is substituted or unsubstituted alkyl, alkenyl, cycloalkyl, heteroalkyl, heterocycloalkyl, heteroalkenyl, heterocycloalkenyl, or cycloalkenyl and optionally, substituted or unsubstituted ($C_1$-$C_3$) alkyl (e.g., methyl, ethyl, propyl, trifluoromethyl) or a substituted or unsubstituted ($C_1$-$C_3$) hydrocarbyl selected from alkenyl, cycloalkyl, heteroalkyl, heterocycloalkyl, heteroalkenyl, heterocycloalkenyl, and cycoalkenyl. In embodiments of formula Iy, $R^{5y}$ is selected from ($C_1$-$C_3$) alkyl (e.g., methyl, ethyl, propyl), and $m^y$ is 1, 2, or 3. In embodiments of formula Iy, each $R^{5y}$ is halogen or haloalkyl (e.g., trifluoromethyl). In embodiments of formula Iy, each $R^{5y}$ is halogen or unsubstituted ($C_1$-$C_3$)alkyl (e.g., methyl, ethyl, propyl). In embodiments of formula Iy, $n^y$ is 0 or 1.

In embodiments of formula Iy, $R^{1y}$ is hydroxy or a physiologically hydrolyzable ester thereof in which the hydrolysis releases the corresponding compound wherein $R^{1y}$ is hydroxy, $R^{6y}$ is unsubstituted cyclohexyl, $m^y$ is 0 and $n^y$ is 0, 1, or 2; or $m^y$ is 1 and $n^y$ is 0, 1, or 2, or $m^y$ is 2 and $n^y$ is 0, 1, or 2. In embodiments of formula Iy, the ester is of the formula —OC(O)$R^{7y}$ wherein $R^{7y}$ is substituted or unsubstituted hydrocarbyl, more optionally, substituted or unsubstituted alkyl, alkenyl, cycloalkyl, heteroalkyl, heterocycloalkyl, heteroalkenyl, heterocycloalkenyl, or cycloalkenyl and further optionally, substituted or unsubstituted ($C_1$-$C_3$)alkyl (e.g., methyl, ethyl, propyl, trifluoromethyl) or a substituted or unsubstituted ($C_1$-$C_3$) hydrocarbyl selected from alkenyl, cycloalkyl, heteroalkyl, heterocycloalkyl, heteroalkenyl, heterocycloalkenyl, and cycoalkenyl. In embodiments of formula Iy, $R^{7y}$ is unsubstituted hydrocarbyl, unsubstituted alkyl, unsubstituted alkenyl, unsubstituted cycloalkyl, unsubstituted heteroalkyl, unsubstituted heterocycloalkyl, unsubstituted heteroalkenyl, unsubstituted heterocycloalkenyl, or unsubstituted cycoalkenyl; or unsubstituted ($C_1$-$C_3$)alkyl (e.g., methyl, ethyl, propyl, trifluoromethyl) or unsubstituted ($C_1$-$C_3$) hydrocarbyl selected from alkenyl, cycloalkyl, heteroalkyl, heterocycloalkyl, heteroalkenyl, heterocycloalkenyl, and cycoalkenyl.

In embodiments of formula Iy, the compound has the formula:

(IIy)

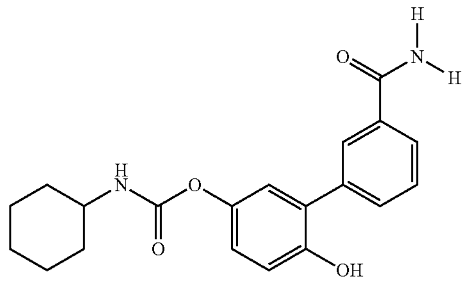

3'-carbamoyl-6-hydroxybiphenyl-3-yl cyclohexylcarbamate or is a physiologically hydrolyzable ester thereof in which the hydrolysis releases 3'-carbamoyl-6-hydroxybiphenyl-3-yl cyclohexylcarbamate or the pharmaceutically acceptable salts thereof. In embodiments, the compound is not a compound of an embodiment of the compound of formula Iy. In embodiments, the compound is not a compound of an embodiment of the compound of formula Iy, as described herein.

Pharmaceutical Compositions

In another aspect is provided a pharmaceutical composition including a compound described herein (including embodiments thereof).

The pharmaceutical composition may include a composition made by admixing a compound described herein and a pharmaceutically acceptable carrier. The pharmaceutical composition may include a composition made by admixing a compound described herein and a pharmaceutically acceptable excipient. Such compositions may be (e.g., are) suitable for pharmaceutical use in an animal (e.g., human).

The pharmaceutical composition may include a compound described herein and a pharmaceutically acceptable carrier. The pharmaceutical composition may include a therapeutically effective amount of one or more compounds described herein (e.g., Formula I (including embodiments thereof)) and a pharmaceutically acceptable carrier.

The pharmaceutical composition may include a therapeutically effective amount of one or more compounds described herein (e.g., Formula I (including embodiments thereof)) and a pharmaceutically acceptable excipient.

In embodiments, the compound can be combined as the active ingredient in intimate admixture with a suitable pharmaceutical carrier and/or excipient according to conventional pharmaceutical compounding techniques.

Methods of Modulating Levels of a Fatty Acid Ethanolamide

In another aspect is provided a method for modulating the level of a fatty acid ethanolamide (FAE) in a subject including administering an effective amount of a composition described herein (e.g., compound described herein (e.g., including embodiments thereof) or a pharmaceutical composition described herein).

In an aspect is provided a composition as described herein (including in an aspect, embodiment, table, figure, claim, sequence listing, or example) (e.g., a compound described herein or a pharmaceutical composition described herein) for use in the manufacture of a medicament for modulating (e.g., increasing, increasing relative to control) the level of a fatty acid ethanolamide (FAE) a subject.

In an aspect is provided a composition as described herein (including in an aspect, embodiment, table, figure, claim, sequence listing, or example) (e.g., a compound described herein or a pharmaceutical composition described herein) for use in modulating (e.g., increasing, increasing relative to control) the level of a fatty acid ethanolamide (FAE) in a subject. The use may include administering to the subject an effective amount of a composition described herein (including in an aspect, embodiment, table, figure, claim, sequence listing, or example) (e.g., a compound described herein or a pharmaceutical composition described herein).

In embodiments, the method or use includes treating a condition associated with an aberrant (e.g, reduced, reduced relative to control) level of AEA and/or OEA and/or PEA. In embodiments, the method or use includes administering an effective (e.g., therapeutically effective) amount of a composition described herein (e.g., compound described herein (e.g., including embodiments thereof) or a pharmaceutical composition described herein). In embodiments, the fatty acid ethanolamide (FAE) is anandamide (AEA). In embodiments, the fatty acid ethanolamide (FAE) is oleoylethanolamide (OEA). In embodiments, the fatty acid ethanolamide (FAE) is palmitoylethanolamide (PEA). In embodiments, the method or use includes modulating (e.g., increasing, increasing relative to control) the level of a fatty acid ethanolamide (FAE) in a subject. In embodiments, the method or use includes treating a condition that may benefit (e.g., the subject may benefit from or the disease or symptom may be treated by) an increased level of AEA and/or OEA and/or PEA.

In an aspect is provided a method of modulating (e.g., reducing, inhibiting) the level of activity of FAAH in a subject, the method including administering an effective amount of a composition as described herein (including in an aspect, embodiment, table, figure, claim, sequence listing, or example) (e.g., a compound described herein or a pharmaceutical composition described herein). The method may include administering to the subject an effective amount of a composition described herein (including in an aspect, embodiment, table, figure, claim, sequence listing, or example) (e.g., a compound described herein or a pharmaceutical composition described herein).

In an aspect is provided a composition as described herein (including in an aspect, embodiment, table, figure, claim, sequence listing, or example) (e.g., a compound described herein or a pharmaceutical composition described herein) for use in the manufacture of a medicament for modulating (e.g., reducing, inhibiting) the level of activity of FAAH in a subject.

In an aspect is provided a composition as described herein (including in an aspect, embodiment, table, figure, claim, sequence listing, or example) (e.g., a compound described herein or a pharmaceutical composition described herein) for use in modulating (e.g., reducing, inhibiting) the level of activity of FAAH in a subject. The use may include administering to the subject an effective amount of a composition described herein (including in an aspect, embodiment, table, figure, claim, sequence listing, or example) (e.g., a compound described herein or a pharmaceutical composition described herein).

Methods of Treatment

In an aspect is provided a method of treating or preventing a disease in a subject in need of the treatment, the method including administering an effective amount of a composition as described herein (including in an aspect, embodiment, table, figure, claim, sequence listing, or example) (e.g., a compound described herein or a pharmaceutical composition described herein), wherein the disease is reduced appetite, gastric damage, enteric damage, a nicotine use disorder, tobacco smoking, substance abuse, a *cannabis* use disorder, a cocaine use disorder, an opioid use disorder, an amphetamine use disorder, a methamphetamine use disorder, an alcohol use disorder, an eating disorder, anxiety, post-traumatic stress disorder, schizophrenia, a mood disorder, pain, inflammation, or ocular glaucoma. The method may include administering to the subject a therapeutically effective amount of a composition described herein (including in an aspect, embodiment, table, figure, claim, sequence listing, or example) (e.g., a compound described herein or a pharmaceutical composition described herein).

In an aspect is provided a composition as described herein (including in an aspect, embodiment, table, figure, claim, sequence listing, or example) (e.g., a compound described herein or a pharmaceutical composition described herein) for use in the manufacture of a medicament for treatment of a disease, wherein the disease is reduced appetite, gastric damage, enteric damage, a nicotine use disorder, tobacco smoking, substance abuse, a *cannabis* use disorder, a cocaine use disorder, an opioid use disorder, an amphetamine use disorder, a methamphetamine use disorder, an alcohol use disorder, an eating disorder, anxiety, post-traumatic stress disorder, schizophrenia, a mood disorder, pain, inflammation, or ocular glaucoma.

In an aspect is provided a composition as described herein (including in an aspect, embodiment, table, figure, claim, sequence listing, or example) (e.g., a compound described herein or a pharmaceutical composition described herein) for use in the treatment or prevention of a disease in a subject, wherein the disease is reduced appetite, gastric damage, enteric damage, a nicotine use disorder, tobacco smoking, substance abuse, a *cannabis* use disorder, a cocaine use disorder, an opioid use disorder, an amphetamine use disorder, a methamphetamine use disorder, an alcohol use disorder, an eating disorder, anxiety, post-traumatic stress disorder, schizophrenia, a mood disorder, pain, inflammation, or ocular glaucoma. The use includes administering to the subject a composition described herein (including in an aspect, embodiment, table, figure, claim, sequence listing, or example) (e.g., a compound described herein or a pharmaceutical composition described herein). The use may include administering to the subject a therapeutically effective amount of a composition described herein (including in an aspect, embodiment, table, figure, claim, sequence listing, or example) (e.g., a compound described herein or a pharmaceutical composition described herein).

In embodiments, the disease is reduced appetite.

In embodiments, the disease is gastric damage. In embodiments, the gastric damage is caused by a non-steroidal anti-inflammatory drug (e.g. aspirin, diclofenac, ibuprofen, or naproxen).

In embodiments, the disease is enteric damage. In embodiments, the enteric damage is caused by a non-steroidal anti-inflammatory drug (e.g. aspirin, diclofenac, ibuprofen, or naproxen).

In embodiments, the disease is a nicotine use disorder. In embodiments, the nicotine use disorder is nicotine craving, nicotine addiction, nicotine dependence, or nicotine withdrawal.

In embodiments, the disease is tobacco smoking.

In embodiments, the disease is tobacco use.

In embodiments, the disease is substance abuse.

In embodiments, the disease is a *cannabis* use disorder. In embodiments, the *cannabis* use disorder is *cannabis* craving, *cannabis* addiction, *cannabis* dependence, or *cannabis* withdrawal.

In embodiments, the disease is a cocaine use disorder. In embodiments, the cocaine use disorder is cocaine craving, cocaine addiction, cocaine dependence, or cocaine withdrawal.

In embodiments, the disease is an opioid use disorder. In embodiments, the opioid use disorder is opioid craving, opioid addiction, opioid dependence, or opioid withdrawal.

In embodiments, the disease is an opiate use disorder. In embodiments, the opiate use disorder is opiate craving, opiate addiction, opiate dependence, or opiate withdrawal.

In embodiments, the disease is an amphetamine use disorder. In embodiments, the amphetamine use disorder is amphetamine craving, amphetamine addiction, amphetamine dependence, or amphetamine withdrawal.

In embodiments, the disease is a methamphetamine use disorder. In embodiments, the methamphetamine use disorder is methamphetamine craving, methamphetamine addiction, methamphetamine dependence, or methamphetamine withdrawal.

In embodiments, the disease is an alcohol use disorder. In embodiments, the alcohol use disorder is alcohol craving, alcohol addiction, alcohol dependence, alcohol withdrawal, or alcohol induced delirium.

In embodiments, the disease is an eating disorder. In embodiments, the eating disorder is bulimia nervosa, anorexia nervosa, a binge eating disorder, or an eating disorder not otherwise specified (EDNOS). In embodiments, the eating disorder is bulimia nervosa, anorexia nervosa, or a binge eating disorder.

In embodiments, the disease is post-traumatic stress disorder.

In embodiments, the disease is schizophrenia.

In embodiments, the disease is a mood disorder. In embodiments, the mood disorder is bipolar disorder type I, bipolar disorder type II, cyclothymia, substance-induced mood disorder, depression, atypical depression, psychotic major depression, post-partum depression, dysthymia, catatonic depression, melancholic depression, or a depressive disorder not otherwise specified (DDNOS). In embodiments, the mood disorder is bipolar disorder type I, bipolar disorder type II, cyclothymia, substance-induced mood disorder, depression, atypical depression, psychotic major depression, post-partum depression, dysthymia, catatonic depression, or melancholic depression.

In embodiments, the disease is pain. In embodiments, the pain is nociceptive pain, neuropathic pain, inflammatory pain, non-inflammatory pain, or pain associated with a chronic condition.

In embodiments, the disease is inflammation. In embodiments, the inflammation is associated with pulmonary edema, kidney stones, minor injuries, wound healing, skin wound healing, vaginitis, candidiasis, lumbar spondylanhrosis, lumbar spondylarthrosis, vascular diseases, migraine headaches, sinus headaches, tension headaches, dental pain, periarteritis *nodosa*, thyroiditis, aplastic anemia, Hodgkin's disease, sclerodoma, rheumatic fever, type I diabetes, type II diabetes, myasthenia gravis, multiple sclerosis, sarcoidosis, nephrotic syndrome, Behcet's syndrome, polymyositis, gingivitis, hypersensitivity, swelling occurring after injury, or myocardial ischemia, or osteoarthritis.

In embodiments, the disease is ocular glaucoma.

In embodiments, the disease is anxiety.

In an aspect is provided a method of reducing tobacco use by a subject, the method including administering an effective amount of a composition as described herein (including in an aspect, embodiment, table, figure, claim, sequence listing, or example) (e.g., a compound described herein or a pharmaceutical composition described herein). In embodiments, the tobacco use is tobacco smoking. In embodiments, the method includes effecting smoking cessation in a subject.

In an aspect is provided a composition as described herein (including in an aspect, embodiment, table, figure, claim, sequence listing, or example) (e.g., a compound described herein or a pharmaceutical composition described herein) for use in the manufacture of a medicament for reducing tobacco smoking by a subject.

In an aspect is provided a composition as described herein (including in an aspect, embodiment, table, figure, claim, sequence listing, or example) (e.g., a compound described herein or a pharmaceutical composition described herein) for use in reducing tobacco use by a subject. In embodiments, the tobacco use is tobacco smoking. In embodiments, the use includes effecting smoking cessation in a subject.

In embodiments, the method or use includes preventing or treating pathological behaviour (e.g., compulsive gambling, compulsive shopping, compulsive hoarding, or kleptomania).

In an aspect is provided a method of preventing or treating pathological behaviour in a subject, the method including administering an effective amount of a composition as described herein (including in an aspect, embodiment, table, figure, claim, sequence listing, or example) (e.g., a compound described herein or a pharmaceutical composition described herein). In embodiments, the pathological behavior is compulsive gambling, compulsive shopping, compulsive hoarding, or kleptomania.

In an aspect is provided a composition as described herein (including in an aspect, embodiment, table, figure, claim, sequence listing, or example) (e.g., a compound described herein or a pharmaceutical composition described herein) for use in the manufacture of a medicament for preventing or treating pathological behaviour in a subject. In embodiments, the pathological behavior is compulsive gambling, compulsive shopping, compulsive hoarding, or kleptomania.

In an aspect is provided a composition as described herein (including in an aspect, embodiment, table, figure, claim, sequence listing, or example) (e.g., a compound described herein or a pharmaceutical composition described herein) for use in preventing or treating pathological behavior in a subject. In embodiments, the pathological behavior is compulsive gambling, compulsive shopping, compulsive hoarding, or kleptomania.

In embodiments, the method or use includes treating or preventing syndromes associated with the consumption of substances of abuse or addiction related disorders (e.g., tobacco craving and addiction, tobacco dependence, tobacco withdrawal, *cannabis* craving and addiction; *cannabis* dependence; *cannabis* withdrawal; cocaine use disorders, including cocaine craving and addiction, cocaine dependence, or cocaine withdrawal; opioid use disorders, including opioid craving and addiction, opioid dependence, or opioid withdrawal; opiate use disorders, including opiate craving and addiction, opiate dependence, or opiate withdrawal; amphetamine use disorders, including amphetamine craving and addiction, amphetamine dependence, or amphetamine withdrawal; methamphetamine use disorders, including methamphetamine craving and addiction, methamphetamine dependence, or methamphetamine withdrawal; alcohol use disorders, including alcohol craving and addiction, alcohol dependence, alcohol withdrawal, or alcohol induced delirium in a mammal (e.g., human).

In embodiments, the method or use includes modulating appetite or body weight in a subject (e.g., mammal).

In embodiments, the method or use includes preventing or treating eating disorders (e.g., bulimia nervosa, anorexia nervosa, binge eating disorder, eating disorder not otherwise specified (EDNOS); in a mammal (e.g., human)). In embodiments, the method or use includes preventing or treating eating disorders (e.g., bulimia nervosa, anorexia nervosa, or binge eating disorder; in a mammal (e.g., human)).

In embodiments, the method or use includes treating anxiety in a mammal.

In embodiments, the method or use includes preventing or treating a mood disorder (e.g., bipolar disorder type I, bipolar disorder type II, cyclothymia, substance-induced mood disorder, depression, atypical depression, psychotic major depression, post-partum depression, dysthymia, catatonic depression, melancholic depression, or depressive disorder not otherwise specified (DDNOS). In embodiments, the method or use includes preventing or treating a mood disorder (e.g., bipolar disorder type I, bipolar disorder type II, cyclothymia, substance-induced mood disorder, depression, atypical depression, psychotic major depression, post-partum depression, dysthymia, catatonic depression, or melancholic depression.

In embodiments, the method or use includes treating post-traumatic stress disorder in a mammal.

In embodiments, the method or use includes treating a pain syndrome, disorder, disease or condition characterized by nociceptive pain, neuropathic pain, inflammatory pain, non-inflammatory pain, or pain associated with chronic conditions such as diabetes.

In embodiments, the method or use includes treating or preventing ocular glaucoma.

In embodiments, the method or use includes preventing or treating gastric and/or enteric damage caused by various agents, including gastric and/or enteric damage produced by non-steroidal anti-inflammatory drugs such as aspirin, diclofenac, ibuprofen or naproxen.

In embodiments, the method or use includes administering a therapeutically effective amount of a composition described herein (including in an aspect, embodiment, table, figure, claim, sequence listing, or example) (e.g., a compound described herein or a pharmaceutical composition described herein).

In embodiments, the method or use includes systemic administration of the composition described herein. In embodiments, the method or use includes parenteral administration of the composition described herein. In embodiments, the method or use includes intravenous administration of the composition described herein. In embodiments, the method or use includes local administration. In embodiments, the method or use includes oral administration.

In an aspect is provided a method of treating or preventing a disease in a subject in need of the treatment, the method including administering an effective amount of a composition as described herein (including in an aspect, embodiment, table, figure, claim, sequence listing, or example) (e.g., a compound described herein or a pharmaceutical composition described herein), wherein the disease is a wound (e.g., treating is wound healing), dermatitis, mucositis, or the over reactivity of peripheral sensory neurons, neurodermatitis, overactive bladder, or cough. The method may include administering to the subject a therapeutically effective amount of a composition described herein (including in an aspect, embodiment, table, figure, claim, sequence listing, or example) (e.g., a compound described herein or a pharmaceutical composition described herein).

In an aspect is provided a composition as described herein (including in an aspect, embodiment, table, figure, claim, sequence listing, or example) (e.g., a compound described herein or a pharmaceutical composition described herein) for use in the manufacture of a medicament for treatment of a disease, wherein the disease is a wound (e.g., treating is wound healing), dermatitis, mucositis, or the over reactivity of peripheral sensory neurons, neurodermatitis, overactive bladder, or cough.

In an aspect is provided a composition as described herein (including in an aspect, embodiment, table, figure, claim, sequence listing, or example) (e.g., a compound described herein or a pharmaceutical composition described herein) for use in the treatment or prevention of a disease in a subject, wherein the disease is a wound (e.g., treating is wound healing), dermatitis, mucositis, or the over reactivity of peripheral sensory neurons, neurodermatitis, overactive bladder, or cough. The use includes administering to the subject a composition described herein (including in an aspect, embodiment, table, figure, claim, sequence listing, or example) (e.g., a compound described herein or a pharmaceutical composition described herein). The use may include administering to the subject a therapeutically effective amount of a composition described herein (including in an aspect, embodiment, table, figure, claim, sequence listing, or example) (e.g., a compound described herein or a pharmaceutical composition described herein).

Methods of Preparing a Compound

In another aspect is provided a method for preparing a compound described herein (including embodiments thereof). In embodiments, the method includes synthetic transformations (e.g., in Michael Smith, Jerry March—*March's Advanced Organic Chemistry: Reactions mechanisms and structure—6th Edition*, John Wiley & Sons Inc., 2007, which is herein incorporated by reference). It is well known to one of ordinary skill in the art that transformation of a chemical function into another may require that one or more reactive centres in the compound containing this function be protected in order to avoid undesired side reactions. Protection of such reactive centres, and subsequent de-protection at the end of the synthetic transformations, can be accomplished following standard procedures described, for instance, in Theodora W. Green and Peter G. M. Wuts—*Protective Groups in Organic Synthesis, Fourth Edition*, John Wiley & Sons Inc., 2006, which is herein incorporated by reference.

The synthesis of compound described herein (including embodiments thereof), according to the synthetic processes described below, can be conducted in a stepwise manner, whereby each intermediate is isolated and purified by standard purification techniques such as, for example, column chromatography, before carrying out the subsequent reaction. Alternatively, two or more steps of the synthetic sequence can be carried out in a so-called "one-pot" procedure, as known in the art, whereby only the compound resulting from the two or more steps is isolated and purified.

Compound described herein (including embodiments thereof) may be synthesized using standard synthetic techniques known to those skilled in the art or using methods known in the art in combination with methods described herein. As a further guide the following synthetic methods may also be utilized to synthesize the compounds provided here or using methodologies analogues to those described below by the use of appropriate alternative starting materials.

In embodiments, are methods for preparing the compounds of general Formula I

I

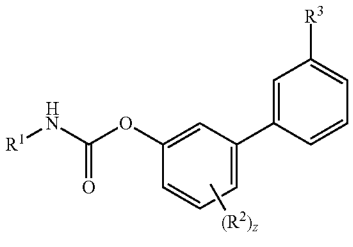

wherein $R^1$, $R^2$, $R^3$, and z have the meanings as defined above, are provided, said methods comprising a carbamoylation reaction of compounds of Formula III, as described in Scheme I.

Scheme I: Synthesis of compounds of Formula I (Method A and B)

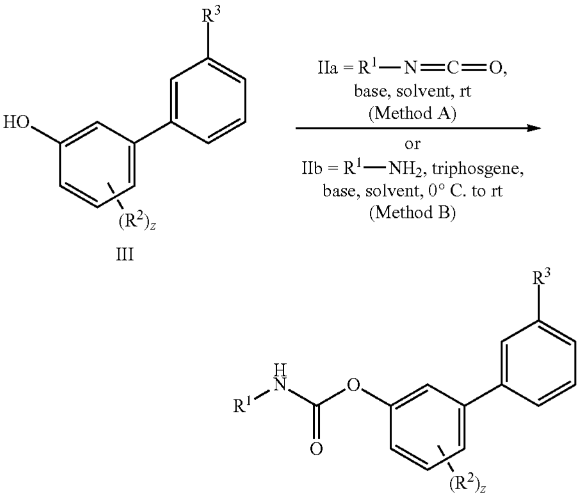

III

I

Compounds of Formula I, wherein $R^1$, $R^2$, $R^3$, and z are as defined above, can be prepared, according to Scheme I (Method A), by reaction of an isocyanate of Formula IIa, wherein $R^1$ is as defined in Formula I, with a compound of Formula III, wherein $R^2$, $R^3$, and z are as defined in Formula I, in the presence of a base, such as 4-dimethylaminopyridine or N,N-diisopropylethylamine, in an organic solvent, such as acetonitrile, at room temperature. Alternatively, compounds of Formula I, wherein $R^1$, $R^2$, $R^3$, and z are as defined above, can be prepared according to Scheme I (Method B) by reaction of compounds of Formula III upon activation as chloroformates using triphosgene in the presence of a base, such as N,N-diisopropylethylamine in an organic solvent, such as dichloromethane, at a temperature from 0° C. to room temperature, as described by Forster et al. *Angew Chem Int Ed Engl,* 1987; 26(9): 894-895, and then reaction with amines of Formula IIb, wherein R is as defined in Formula I.

Alternatively, amines of Formula IIb, wherein $R^1$ is as defined in Formula I, can react with a compound of Formula III, wherein $R^2$, $R^3$, and z are as defined in Formula I, upon activation of the amines of Formula IIb by reaction with triphosgene in the presence of a base, such as 4-dimethylaminopyridine, in dichloromethane, at a temperature from 0° C. to room temperature, to produce compounds of Formula I.

In accordance with certain embodiments, compounds of Formula III are substituted phenols as those herein represented:

IIIa

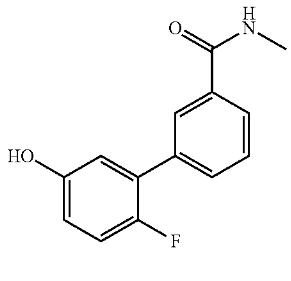

-continued

IIIb

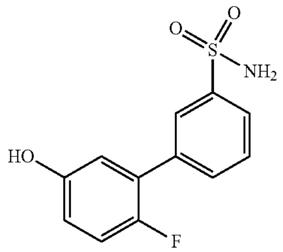

IIIc

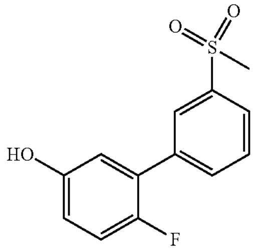

IIId

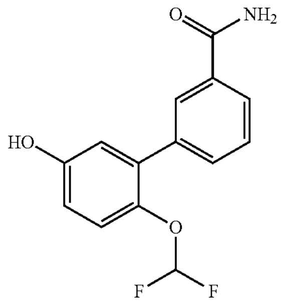

IIIe

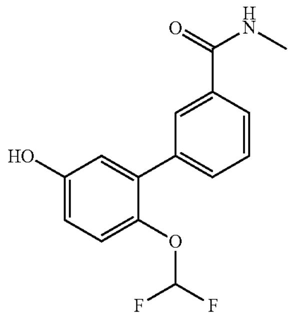

IIIf

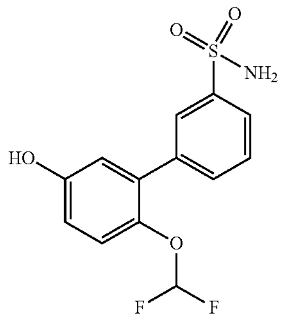

-continued

IIIg

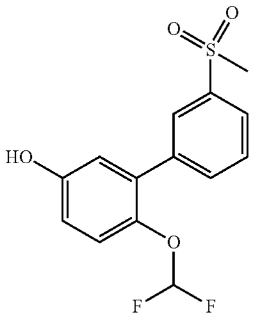

IIIh

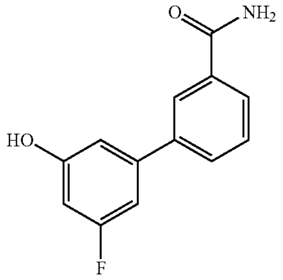

IIIi

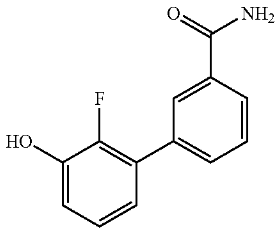

According to Scheme II, compounds of Formula III or the corresponding benzyl ethers of Formula III' wherein, $R^2$, $R^3$, and z are as defined in Formula I, can be prepared by palladium-catalyzed reaction between boronic acids of Formula IV, wherein $R^3$ is as defined in Formula I, or the corresponding boronic esters, and phenolic halides or triflates of Formula V or the corresponding benzyl ethers V' in which $R^2$ and z are as defined above and Y is bromine, chlorine, iodine or triflate.

Scheme II: Synthesis of compounds of Formula III or the corresponding benzyl ethers III'

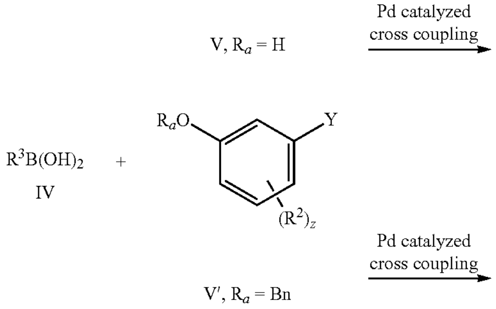

-continued

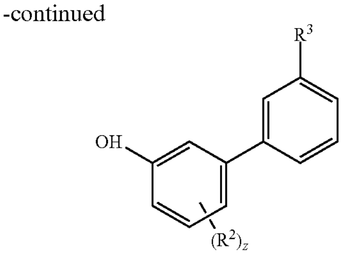

III

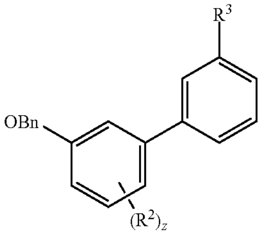

III'

In accordance with certain embodiments, compounds of Formula III' are substituted phenyl benzyl ethers as those herein represented:

IId'

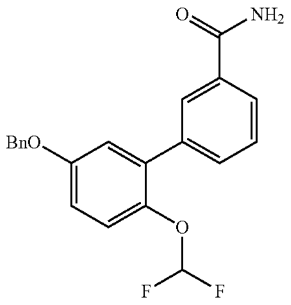

IIIe'

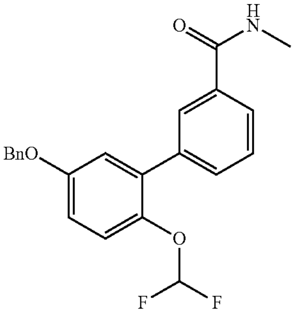

IIIf'

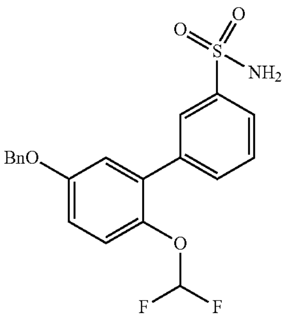

-continued

IIIg'

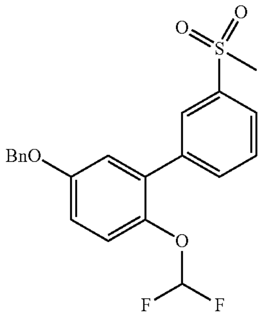

IIIh'

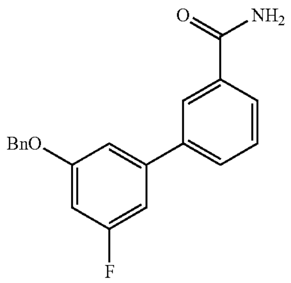

In accordance with certain embodiments, compounds of Formula V or the corresponding benzyl ethers of Formula V' are phenyl bromides as those herein represented:

Va

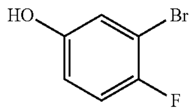

Vb

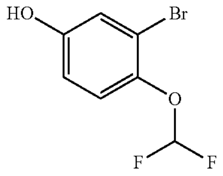

Vc

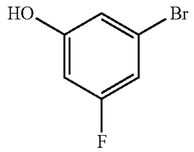

Vd

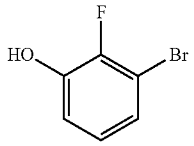

Va'

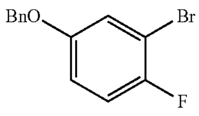

-continued

Vb'

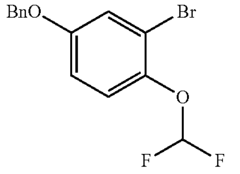

Vc'

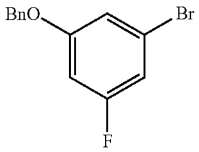

Alternatively, compounds of Formula I can be prepared according to Scheme III by palladium-catalyzed reaction between boronic acids of Formula IV wherein $R^3$ is as defined in Formula I, or the corresponding boronic esters and phenyl halides or triflates of Formula VI wherein $R^1$, $R^2$, and z are as defined in Formula I and Y is bromine, chlorine, iodine or triflate.

Scheme III: Synthesis of compounds of Formula I

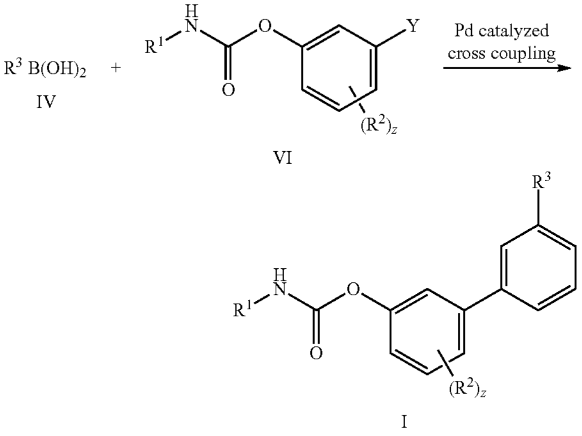

Palladium-catalyzed reactions of boronic acids of Formula IV, as described above, or the corresponding boronic esters, with compounds of Formula V, V', and VI, as described above, are conducted according to or in analogy to literature procedures reported, for instance, in Miyaura, N., Suzuki, A. *Chem Rev,* 1995; 95: 2457-2483; Kotha et al. *Tetrahedron* 2002; 58: 9633-9695; Suzuki, A. *Angew Chem Int Ed Engl,* 2011; 50: 6722-6737, and references cited therein, which are herein incorporated as references.

In accordance with certain embodiments, compounds of Formula VI are cyclic alkyl carbamates as those herein represented:

VIa

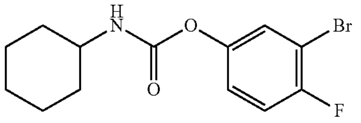

-continued

VIb

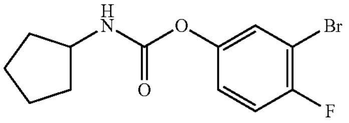

VIc

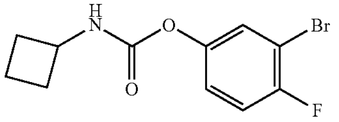

Compounds of Formula VI wherein $R^1$, $R^2$, and z are as defined in Formula I and Y is bromine, chlorine, iodine or triflate can be prepared according to Scheme IV by a carbamoylation reaction of compounds of Formula V wherein $R^2$ and z are as defined above and Y is bromine, chlorine, iodine or triflate.

Scheme IV: Synthesis of compounds of Formula VI

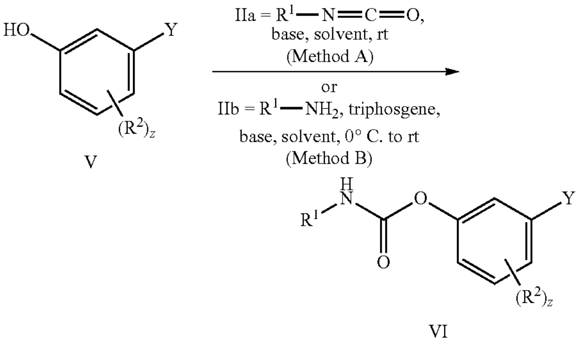

Treatment of compounds of Formula V, wherein $R^2$ and z are as defined above and Y is bromine, chlorine, iodine or triflate, with isocyanates of Formula IIa, wherein $R^1$ is as defined in Formula I, in the presence of a base, such as 4-dimethylaminopyridine in an organic solvent, such as acetonitrile (Method A), at room temperature, results in the formation of compounds of Formula VI, wherein $R^1$, $R^2$, and z are as defined in Formula I and Y is bromine, chlorine, iodine or triflate. Alternatively, compounds of Formula VI, wherein $R^1$, $R^2$, and z are as defined in Formula I and Y is bromine, chlorine, iodine or triflate can be prepared according to Scheme IV (Method B) by reaction of compounds of Formula V, wherein $R^2$ and z are as defined above and Y is bromine, chlorine, iodine or triflate, upon activation as chloroformates using triphosgene in the presence of a base, such as pyridine in an organic solvent, such as dichloromethane, at a temperature from 0° C. to room temperature, and then reaction with amines of Formula IIb, wherein $R^1$ is as defined in Formula I. Alternatively, amines of Formula IIb, wherein $R^1$ is as defined in Formula I, can react with a compound of Formula V, wherein $R^2$ and z are as defined above and Y is bromine, chlorine, iodine or triflate, upon activation of the amines of Formula IIb, wherein $R^1$ is as defined in Formula I, by reaction with triphosgene in the presence of a base, such as 4-dimethylaminopyridine, in dichloromethane, at a temperature from 0° C. to room temperature, to produce compounds of Formula VI, wherein $R^1$, $R^2$, and z are as defined in Formula I and Y is bromine, chlorine, iodine or triflate.

Isocyanates of Formula IIa and amines of Formula IIb, wherein $R^1$ is as defined in Formula I, boronic acids of Formula IV or the corresponding boronic esters, wherein $R^3$ is as defined in Formula I, compounds of Formula V or the corresponding benzyl ethers of Formula V', wherein $R^2$ and z are as defined above and Y is bromine, chlorine, iodine or triflate, are either commercially available or can be prepared from commercially available compounds according to general synthetic procedures described for instance in Michael Smith, Jerry March—*March's Advanced Organic Chemistry: Reactions mechanisms and structure—6th Edition*, John Wiley & Sons Inc., 2007, or in Molina P., Tarraga A., Argues A. in Katritzky A. R., Taylor R. J. K., *Comprehensive Organic Functional Group Transformations II*, Elsevier, 2004, Vol. 5, pag. 949-973, and references cited therein, which are herein incorporated by reference.

Any combination of the substituents or groups as defined or described above for the various variables is contemplated herein.

The compounds of Formula I, prepared with the methods described herein above, may be treated or purified by conventional techniques such as, for example, filtration, distillation, chromatography, recrystallization and combinations thereof.

Additional Embodiments Section

1. A compound having the formula:

(I)

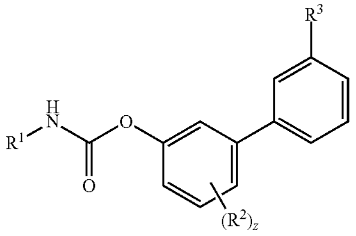

, wherein, $R^1$ is substituted or unsubstituted cycloalkyl, substituted or unsubstituted heterocycloalkyl, substituted or unsubstituted aryl, or substituted or unsubstituted heteroaryl; $R^2$ is independently halogen, $—CX_3$, $—OCX_3$, $—OCHX_2$, substituted or unsubstituted $C_1$-$C_8$ alkyl, or substituted or unsubstituted 2 to 8 membered heteroalkyl; $R^3$ is $—SO_2R^6$, $—SO_2NR^4R^5$, or $—C(O)NR^4R^5$. $R^4$, $R^5$, and $R^6$ are independently hydrogen, substituted or unsubstituted $C_1$-$C_8$ alkyl or substituted or unsubstituted 2 to 8 membered heteroalkyl; where $R^4$ and $R^5$ are bonded to the same nitrogen atom, they may optionally be joined to form a substituted or unsubstituted 4 to 8 membered heterocycloalkyl or substituted or unsubstituted 5 to 6 membered heteroaryl; the symbol z is an integer from 1 to 4; and the symbol X is —F, —Cl, —Br, or —I; or a pharmaceutically acceptable salt thereof.

2 The compound of embodiment 1, having the formula:

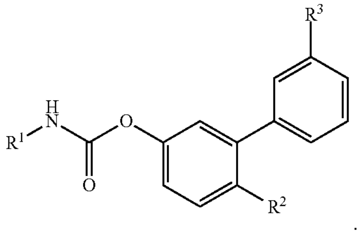

.

3 The compound of embodiment 1, having the formula:

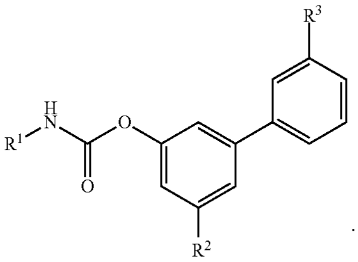

.

4 The compound of embodiment 1, having the formula:

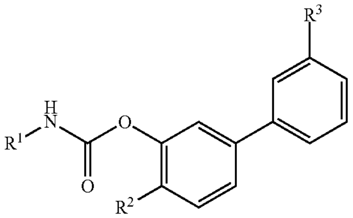

.

5 The compound of embodiment 1, having the formula:

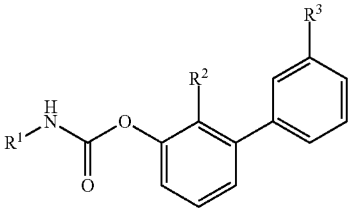

.

6 The compound of one of embodiments 1 to 5, wherein $R^1$ is substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl.

7 The compound of one of embodiments 1 to 6, wherein $R^1$ is unsubstituted $C_3$-$C_8$ cycloalkyl, unsubstituted 3 to 8 membered heterocycloalkyl, unsubstituted $C_6$-$C_{10}$ aryl, or unsubstituted 5 to 10 membered heteroaryl.

8 The compound of one of embodiments 1 to 7, wherein $R^1$ is unsubstituted $C_3$-$C_8$ cycloalkyl or unsubstituted 3 to 8 membered heterocycloalkyl.

9 The compound of one of embodiments 1 to 8, wherein $R^1$ is unsubstituted $C_3$-$C_8$ cycloalkyl.

10 The compound of one of embodiments 1 to 9, wherein $R^1$ is unsubstituted $C_4$-$C_8$ cycloalkyl.

11 The compound of one of embodiments 1 to 10, wherein $R^1$ is unsubstituted $C_4$-$C_6$ cycloalkyl (e.g., cyclobutyl, cyclopentyl, or cyclohexyl).

12 The compound of one of embodiments 1 to 11, wherein $R^1$ is unsubstituted $C_6$ cycloalkyl.

13 The compound of one of embodiments 1 to 12, wherein $R^1$ is unsubstituted cyclohexyl.

14 The compound of one of embodiments 1 to 13, wherein $R^2$ is independently halogen, $—CX_3$, $—OCX_3$, $—OCHX_2$, substituted or unsubstituted $C_1$-$C_8$ alkyl, or substituted or unsubstituted 2 to 8 membered heteroalkyl.

15 The compound of one of embodiments 1 to 14, wherein $R^2$ is independently halogen, —$CX_3$, —$OCX_3$, —$OCHX_2$, substituted or unsubstituted $C_1$-$C_4$ alkyl, or substituted or unsubstituted 2 to 4 membered heteroalkyl.

16 The compound of one of embodiments 1 to 15, wherein $R^2$ is independently halogen, —$CX_3$, —$OCX_3$, or —$OCHX_2$.

17 The compound of one of embodiments 1 to 16, wherein $R^2$ is independently halogen or —$OCHX_2$.

18 The compound of one of embodiments 1 to 17, wherein $R^2$ is independently —$OCHX_2$.

19 The compound of one of embodiments 1 to 17, wherein $R^2$ is independently halogen.

20 The compound of one of embodiments 1 to 18, wherein X is —F.

21 The compound of one of embodiments 1 to 17 and 19, wherein $R^2$ is —F.

22 The compound of one of embodiments 1 to 21, wherein $R^3$ is —$C(O)NR^4R^5$.

23 The compound of one of embodiments 1 to 21, wherein $R^3$ is —$SO_2NR^4R^5$.

24 The compound of one of embodiments 1 to 23, wherein $R^4$ is hydrogen, substituted or unsubstituted $C_1$-$C_6$ alkyl or substituted or unsubstituted 2 to 6 membered heteroalkyl.

25 The compound of one of embodiments 1 to 23, wherein $R^4$ is hydrogen, substituted or unsubstituted $C_1$-$C_4$ alkyl or substituted or unsubstituted 2 to 4 membered heteroalkyl.

26 The compound of one of embodiments 1 to 23, wherein $R^4$ is hydrogen, unsubstituted $C_1$-$C_4$ alkyl or unsubstituted 2 to 4 membered heteroalkyl.

27 The compound of one of embodiments 1 to 23, wherein $R^4$ is hydrogen or unsubstituted $C_1$-$C_4$ alkyl.

28 The compound of one of embodiments 1 to 23, wherein $R^4$ is hydrogen.

29 The compound of one of embodiments 1 to 23, wherein $R^4$ is unsubstituted methyl.

30 The compound of one of embodiments 1 to 30, wherein $R^5$ is hydrogen, substituted or unsubstituted $C_1$-$C_6$ alkyl or substituted or unsubstituted 2 to 6 membered heteroalkyl.

31 The compound of one of embodiments 1 to 30, wherein $R^5$ is hydrogen, substituted or unsubstituted $C_1$-$C_4$ alkyl or substituted or unsubstituted 2 to 4 membered heteroalkyl.

32 The compound of one of embodiments 1 to 30, wherein $R^5$ is hydrogen, unsubstituted $C_1$-$C_4$ alkyl or unsubstituted 2 to 4 membered heteroalkyl.

33 The compound of one of embodiments 1 to 30, wherein $R^5$ is hydrogen or unsubstituted $C_1$-$C_4$ alkyl.

34 The compound of one of embodiments 1 to 30, wherein $R^5$ is hydrogen.

35 The compound of one of embodiments 1 to 30, wherein $R^5$ is unsubstituted methyl.

36 The compound of one of embodiments 1 to 21, wherein $R^3$ is —$SO_2R^6$.

37 The compound of one of embodiments 1 to 21 and 36, wherein $R^6$ is substituted or unsubstituted $C_1$-$C_8$ alkyl or substituted or unsubstituted 2 to 8 membered heteroalkyl.

38 The compound of one of embodiments 1 to 21 and 36, wherein $R^6$ is substituted or unsubstituted $C_1$-$C_6$ alkyl or substituted or unsubstituted 2 to 6 membered heteroalkyl.

39 The compound of one of embodiments 1 to 21 and 36, wherein $R^6$ is substituted or unsubstituted $C_1$-$C_4$ alkyl or substituted or unsubstituted 2 to 4 membered heteroalkyl.

40 The compound of one of embodiments 1 to 21 and 36, wherein $R^6$ is unsubstituted $C_1$-$C_4$ alkyl or unsubstituted 2 to 4 membered heteroalkyl.

41 The compound of one of embodiments 1 to 21 and 36, wherein $R^6$ is unsubstituted $C_1$-$C_4$ alkyl.

42 The compound of one of embodiments 1 to 21 and 36, wherein $R^6$ is unsubstituted methyl.

43 The compound of one of embodiments 1 to 23, wherein $R^4$ and $R^5$ are joined to form a substituted or unsubstituted 4 to 8 membered heterocycloalkyl.

44 The compound of one of embodiments 1 to 23, wherein $R^4$ and $R^5$ are joined to form a substituted or unsubstituted 4 to 6 membered heterocycloalkyl.

45 The compound of one of embodiments 1 to 23, wherein $R^4$ and $R^5$ are joined to form an unsubstituted 4 to 6 membered heterocycloalkyl.

46 The compound of one of embodiments 1 to 23, wherein $R^4$ and $R^5$ are joined to form an unsubstituted 5 to 6 membered heterocycloalkyl.

47 The compound of one of embodiments 1 to 23, wherein $R^4$ and $R^5$ are joined to form an unsubstituted 6 membered heterocycloalkyl.

48 The compound of one of embodiments 1 to 47, wherein the symbol z is 1.

49 The compound of one of embodiments 1 to 47, wherein the symbol z is 2.

50 The compound of one of embodiments 1 to 47, wherein the symbol z is 3.

51 The compound of one of embodiments 1 to 47, wherein the symbol z is 4.

52 The compound of one of embodiments, 1 to 5, wherein $R^1$ is cyclobutyl, cyclopentyl, or cyclohexyl; $R^2$ is —F or —$OCHF_2$; $R^3$ is —$SO_2NH_2$, —$SO_2NHMe$, —$SO_2NMe_2$, —$CONH_2$, —$CONHMe$, —$CONMe_2$, or —$SO_2Me$; and z is 1.

53 The compound of embodiment 2, wherein $R^1$ is cyclobutyl, cyclopentyl, or cyclohexyl; $R^2$ is —F or —$OCHF_2$; and $R^3$ is —$SO_2NH_2$, —$SO_2NHMe$, —$SO_2NMe_2$, —$CONH_2$, —$CONHMe$, —$CONMe_2$, or —$SO_2Me$.

54 The compound of one of embodiments, 1 to 53, wherein the compound is not

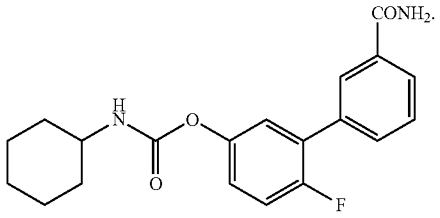

55 The compound of one of embodiments, 1 to 53, wherein the compound is not

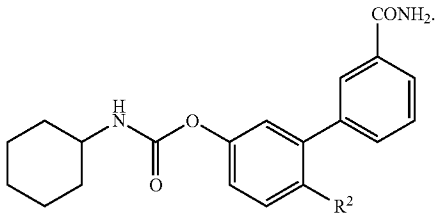

56 The compound of one of embodiments, 1 to 53, wherein the compound is not

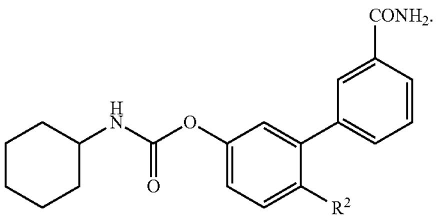

wherein $R^2$ is halogen, —$CX_3$, —$OCX_3$, —$OCHX_2$, substituted or unsubstituted $C_1$-$C_8$ alkyl, or substituted or unsubstituted 2 to 8 membered heteroalkyl.

57 The compound of one of embodiments, 1 to 53, wherein the compound is not

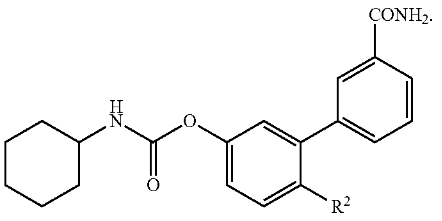

wherein $R^2$ is halogen, —$CX_3$, —$OCX_3$, —$OCHX_2$, substituted or unsubstituted $C_1$-$C_4$ alkyl, or substituted or unsubstituted 2 to 4 membered heteroalkyl.

58 The compound of one of embodiments, 1 to 53, wherein the compound is not

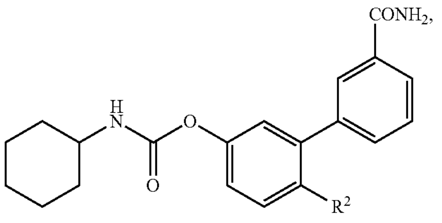

wherein $R^2$ is halogen, —$CX_3$, —$OCX_3$, or —$OCHX_2$.

59 The compound of one of embodiments, 1 to 53, wherein the compound is not

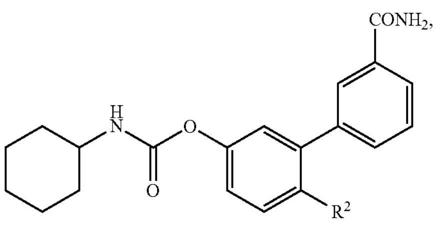

wherein $R^2$ is halogen or —$OCHX_2$.

60 The compound of one of embodiments, 1 to 53, wherein the compound is not

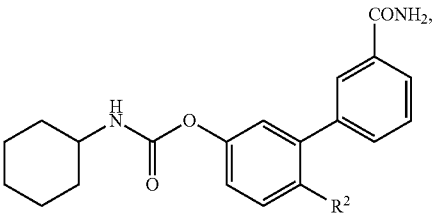

wherein $R^2$ is —$OCHX_2$.

61 The compound of one of embodiments, 1 to 53, wherein the compound is not

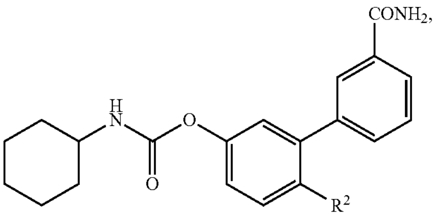

wherein $R^2$ is halogen.

62 The compound of embodiment 1, wherein the compound is

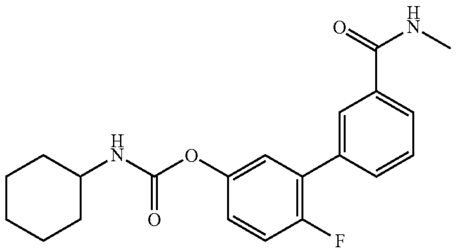

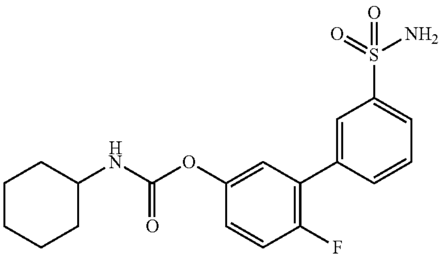

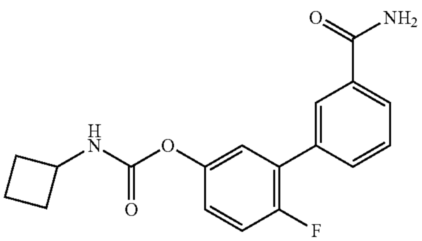

-continued

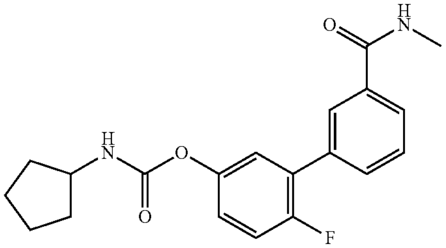

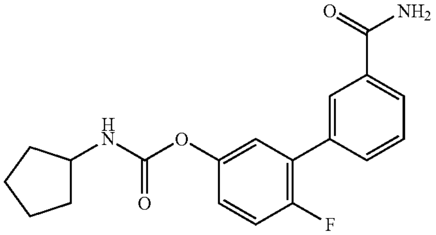

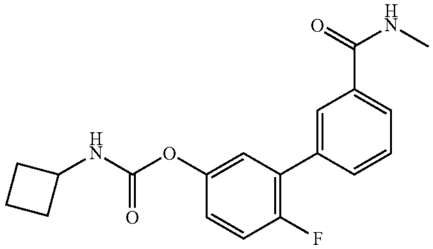

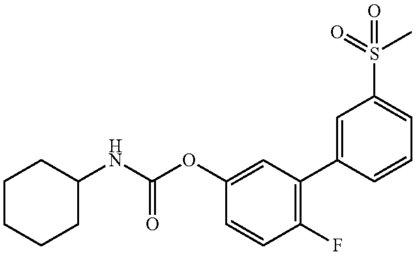

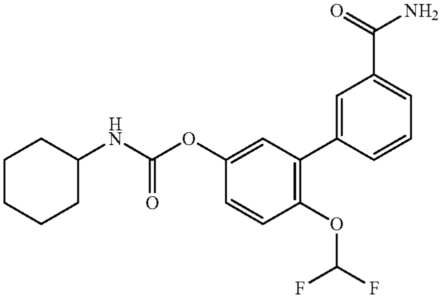

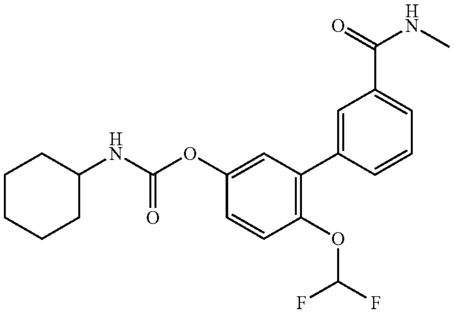

-continued

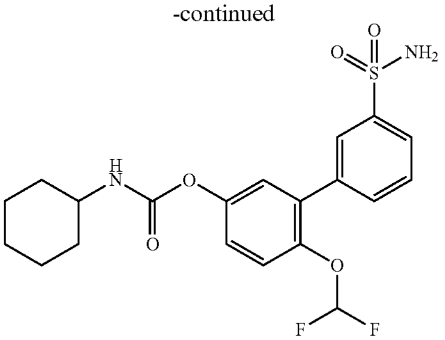

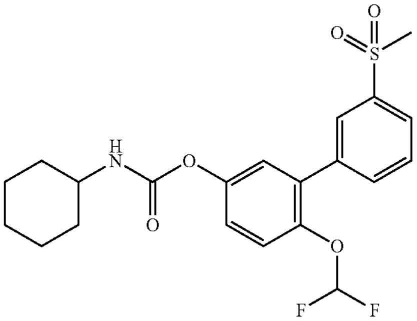

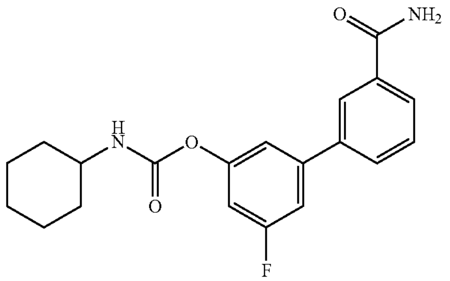

or

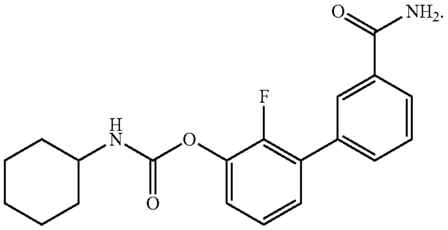

63 A pharmaceutical composition comprising a pharmaceutically acceptable excipient and a compound, or a pharmaceutically acceptable salt thereof, of any one of embodiments 1 to 62.

64 A method of reducing tobacco smoking by a patient, said method comprising administering an effective amount of a compound to said patient, wherein said compound is a compound of one of embodiments 1 to 62.

65 A method of reducing tobacco use by a patient, said method comprising administering an effective amount of a compound to said patient, wherein said compound is a compound of one of embodiments 1 to 62.

66 A method of treating a nicotine use disorder in a patient in need of such treatment, said method comprising administering a therapeutically effective amount of a compound to said patient, wherein said compound is a compound of one of embodiments 1 to 62.

67 The method of embodiment 66, wherein said nicotine use disorder is nicotine craving, nicotine addiction, nicotine dependence, or nicotine withdrawal.

68 A method of treating substance abuse in a patient in need of such treatment, said method comprising administering a therapeutically effective amount of a compound to said patient, wherein said compound is a compound of one of embodiments 1 to 62.

69 A method of treating a *cannabis* use disorder in a patient in need of such treatment, said method comprising administering a therapeutically effective amount of a compound to said patient, wherein said compound is a compound of one of embodiments 1 to 62.

70 The method of embodiment 69, wherein said *cannabis* use disorder is *cannabis* craving, *cannabis* addiction, *cannabis* dependence, or *cannabis* withdrawal.

71 A method of treating a cocaine use disorder in a patient in need of such treatment, said method comprising administering a therapeutically effective amount of a compound to said patient, wherein said compound is a compound of one of embodiments 1 to 62.

72 The method of embodiment 71, wherein said cocaine use disorder is cocaine craving, cocaine addiction, cocaine dependence, or cocaine withdrawal.

73 A method of treating an opioid use disorder in a patient in need of such treatment, said method comprising administering a therapeutically effective amount of a compound to said patient, wherein said compound is a compound of one of embodiments 1 to 62.

74 The method of embodiment 73, wherein said opioid use disorder is opioid craving, opioid addiction, opioid dependence, or opioid withdrawal.

75 A method of treating an opiate use disorder in a patient in need of such treatment, said method comprising administering a therapeutically effective amount of a compound to said patient, wherein said compound is a compound of one of embodiments 1 to 62.

76 The method of embodiment 75, wherein said opiate use disorder is opiate craving, opiate addiction, opiate dependence, or opiate withdrawal.

77 A method of treating an amphetamine use disorder in a patient in need of such treatment, said method comprising administering a therapeutically effective amount of a compound to said patient, wherein said compound is a compound of one of embodiments 1 to 62.

78 The method of embodiment 77, wherein said amphetamine use disorder is amphetamine craving, amphetamine addiction, amphetamine dependence, or amphetamine withdrawal.

79 A method of treating a methamphetamine use disorder in a patient in need of such treatment, said method comprising administering a therapeutically effective amount of a compound to said patient, wherein said compound is a compound of one of embodiments 1 to 62.

80 The method of embodiment 79, wherein said methamphetamine use disorder is methamphetamine craving, methamphetamine addiction, methamphetamine dependence, or methamphetamine withdrawal.

81 A method of treating an alcohol use disorder in a patient in need of such treatment, said method comprising administering a therapeutically effective amount of a compound to said patient, wherein said compound is a compound of one of embodiments 1 to 62.

82 The method of embodiment 81, wherein said alcohol use disorder is alcohol craving, alcohol addiction, alcohol dependence, alcohol withdrawal, or alcohol induced delirium.

83 A method of treating an eating disorder in a patient in need of such treatment, said method comprising administering a therapeutically effective amount of a compound to said patient, wherein said compound is a compound of one of embodiments 1 to 62.

84 The method of embodiment 83, wherein said eating disorder is bulimia nervosa, anorexia nervosa, a binge eating disorder, or an eating disorder not otherwise specified (EDNOS).

85 A method of treating anxiety in a patient in need of such treatment, said method comprising administering a therapeutically effective amount of a compound to said patient, wherein said compound is a compound of one of embodiments 1 to 62.

86 A method of treating post-traumatic stress disorder in a patient in need of such treatment, said method comprising administering a therapeutically effective amount of a compound to said patient, wherein said compound is a compound of one of embodiments 1 to 62.

87 A method of treating schizophrenia in a patient in need of such treatment, said method comprising administering a therapeutically effective amount of a compound to said patient, wherein said compound is a compound of one of embodiments 1 to 62.

88 A method of treating a mood disorder in a patient in need of such treatment, said method comprising administering a therapeutically effective amount of a compound to said patient, wherein said compound is a compound of one of embodiments 1 to 62.

89 The method of embodiment 88, wherein said mood disorder is bipolar disorder type I, bipolar disorder type II, cyclothymia, substance-induced mood disorder, depression, atypical depression, psychotic major depression, post-partum depression, dysthymia, catatonic depression, melancholic depression, or a depressive disorder not otherwise specified (DDNOS).

90 A method of treating pain in a patient in need of such treatment, said method comprising administering a therapeutically effective amount of a compound to said patient, wherein said compound is a compound of one of embodiments 1 to 62.

91 The method of embodiment 90, wherein said pain is nociceptive pain, neuropathic pain, inflammatory pain, non-inflammatory pain, or pain associated with a chronic condition.

92 A method of treating ocular glaucoma in a patient in need of such treatment, said method comprising administering a therapeutically effective amount of a compound to said patient, wherein said compound is a compound of one of embodiments 1 to 62.

93 A method of treating reduced appetite in a patient in need of such treatment, said method comprising administering a therapeutically effective amount of a compound to said patient, wherein said compound is a compound of one of embodiments 1 to 62.

94 A method of modulating the level of a fatty acid ethanolamide (FAE) in a subject comprising administering an effective amount of a compound of one of embodiments 1 to 62 to said subject.

95 The method of embodiment 94, wherein the FAE is anandamide.

96 The method of embodiment 94, wherein the FAE is oleoylethanolamide.

97 The method of embodiment 94, wherein the FAE is palmitoylethanolamide.

98 A method of modulating the level of activity of FAAH in a subject comprising administering an effective amount of a compound of one of embodiments 1 to 62 to said subject.

99 A method of treating gastric or enteric damage in a patient in need of such treatment, said method comprising administering a therapeutically effective amount of a compound to said patient, wherein said compound is a compound of one of embodiments 1 to 62.

100 The method of embodiment 99, wherein said gastric or enteric damage is caused by a non-steroidal anti-inflammatory drug (e.g. aspirin, diclofenac, ibuprofen, or naproxen).

101 The compound of one of embodiments 1 to 62, wherein the compound has an oral bioavailability of greater than 35% in a subject.

102 The compound of one of embodiments 1 to 62, wherein the compound has an oral bioavailability of greater than 45% in a subject.

103 The compound of one of embodiments 1 to 62, wherein the compound has an oral bioavailability of greater than 55% in a subject.

104 The compound of one of embodiments 1 to 62, wherein the compound has an oral bioavailability of greater than 65% in a subject.

105 The compound of one of embodiments 1 to 62, wherein the compound has an oral bioavailability of greater than 75% in a subject.

106 The compound of one of embodiments 1 to 62, wherein the compound has an oral bioavailability of greater than 85% in a subject.

107 The compound of one of embodiments 1 to 62, wherein the compound has an oral bioavailability of greater than 95% in a subject.

108 The compound of one of embodiments 1 to 62 and 101 to 107, wherein each alkyl is a saturated alkyl.

109 The method of one of embodiments 64 to 100 comprising administering an effective amount of a compound of one of embodiments 101 to 108 to said subject.

110 The method of one of embodiments 64 to 100 and 109, wherein said compound is in a pharmaceutical composition of claim 63.

1p. A compound of Formula I (I)

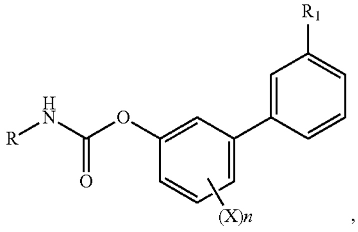

, wherein: R is cycloalkyl; $R_1$ is $SO_2NR'R''$, $CONR'R''$, or $SO_2R'''$; R' and R'' are independently hydrogen or alkyl; or R' and R'' together with the N atom to which they are connected may form a 4- to 6-membered ring, and R''' is alkyl; n is an integer selected from 1 or 2; X is F or $OCHF_2$; with the proviso that when R is cyclohexyl, $R_1$ is $CONH_2$, n is 1 and X is F, then X is not attached in position para to the carbamate.

2p. A compound according to embodiment 1p, wherein: R is cyclobutyl, cyclopentyl, or cyclohexyl; $R_1$ is $SO_2NH_2$, $SO_2NHMe$, $SO_2NMe_2$, $CONH_2$, CONHMe, $CONMe_2$, or $SO_2Me$; n is 1; X is F or $OCHF_2$, with the proviso that when R is cyclohexyl, $R_1$ is $CONH_2$ and X is F, then X is not attached in position para to the carbamate.

3p. A compound according to embodiment 2p, wherein: R is cyclobutyl, cyclopentyl or cyclohexyl; $R_1$ is $SO_2NH_2$, $SO_2NHMe$, $SO_2NMe_2$, $CONH_2$, CONHMe, $CONMe_2$, or $SO_2Me$; n is 1; X is F or $OCHF_2$ and is attached in position para to the carbamate, with the proviso that when R is cyclohexyl and $R_1$ is $CONH_2$, X is not F.

4p. A compound selected from the group consisting of: [4-fluoro-3-[3-(methylcarbamoyl)phenyl]phenyl] N-cyclohexylcarbamate, [4-fluoro-3-(3-sulfamoylphenyl)phenyl] N-cyclohexylcarbamate, [3-(3-carbamoylphenyl)-4-fluoro-phenyl] N-cyclobutylcarbamate, [4-fluoro-3-[3-(methylcarbamoyl)phenyl] phenyl] N-cyclopentylcarbamate, [3-(3-carbamoylphenyl)-4-fluoro-phenyl] N-cyclopentylcarbamate, [4-fluoro-3-[3-(methylcarbamoyl)phenyl] phenyl] N-cyclobutylcarbamate, [4-fluoro-3-(3-methylsulfonylphenyl) phenyl] N-cyclohexylcarbamate, [3-(3-carbamoylphenyl)-4-(difluoromethoxy)phenyl] N-cyclohexylcarbamate, [4-(difluoromethoxy)-3-[3-(methylcarbamoyl)phenyl]phenyl] N-cyclohexylcarbamate, [4-(difluoromethoxy)-3-(3-sulfamoylphenyl)phenyl] N-cyclohexylcarbamate, [4-(difluoromethoxy)-3-(3-methylsulfonylphenyl)phenyl] N-cyclohexylcarbamate, [3-(3-carbamoylphenyl)-5-fluoro-phenyl] N-cyclohexylcarbamate, and [3-(3-carbamoylphenyl)-2-fluoro-phenyl] N-cyclohexylcarbamate.

5p. A pharmaceutical composition comprising an effective amount of a compound of one of embodiments 1p to 4p and a pharmaceutically acceptable excipient.

6p. The compound of one of embodiments 1p to 4p or a pharmaceutical composition of embodiment 5, for use as a medicament.

7p. The compound of one of embodiments 1p to 4p or a pharmaceutical composition of embodiment 5, for use in a method for modulating the level of a fatty acid ethanolamide (FAE) in a subject.

8p. The compound of one of embodiments 1p to 4p or a pharmaceutical composition of embodiment 5, for use in a method of effecting smoking cessation or for reducing tobacco use in a mammal, or for use in a method for the treatment or prevention of nicotine use disorders in a mammal, including nicotine craving and addiction, nicotine dependence, and nicotine withdrawal.

9p. The compound of one of embodiments 1p to 4p or a pharmaceutical composition of embodiment 5, for use in a method of treating or preventing a substance abuse disorder in a mammal.

10p. The compound or pharmaceutical composition of embodiment 9p, wherein the substance abuse disorder is selected from *cannabis* use disorders, including *cannabis* craving and addiction, *cannabis* dependence, or *cannabis* withdrawal; cocaine use disorders, including cocaine craving and addiction, cocaine dependence, or cocaine withdrawal; opioid use disorders, including opioid craving and addiction, opioid dependence, or opioid withdrawal; opiate use disorders, including opiate craving and addiction, opiate dependence, or opiate withdrawal; amphetamine use disorders, including amphetamine craving and addiction, amphetamine dependence, or amphetamine withdrawal; methamphetamine use disorders, including methamphetamine craving and addiction, methamphetamine dependence, or methamphetamine withdrawal; or alcohol use disorders, including alcohol craving and addiction, alcohol dependence, alcohol withdrawal, or alcohol induced delirium.

11p. The compound of one of embodiments 1p to 4p or a pharmaceutical composition of embodiment 5, for use in a method of preventing or treating an eating disorder in a mammal.

12p. The compound or pharmaceutical composition of embodiment 11p, wherein the eating disorder is selected from bulimia nervosa and anorexia nervosa, a binge eating disorder or an eating disorder not otherwise specified (EDNOS).

13p. The compound of one of embodiments 1p to 4p or a pharmaceutical composition of embodiment 5, for use in modulating appetite in a mammal.

14p. The compound of one of embodiments 1p to 4p or a pharmaceutical composition of embodiment 5, for use in a method of preventing or treating anxiety, a post-traumatic stress disorder or schizophrenia in a mammal.

15p. A compound of one of embodiments 1p to 4p or a pharmaceutical composition of embodiment 5, for use in a method of treating or preventing a mood disorder in a mammal.

16p. The compound or pharmaceutical composition of embodiment 15p, wherein the mood disorder is selected from bipolar disorder type I, bipolar disorder type II, cyclothymia, substance-induced mood disorder, depression, atypical depression, psychotic major depression, post-partum depression, dysthymia, catatonic depression, melancholic depression, or a depressive disorder not otherwise specified (DDNOS).

17p. A compound of one of embodiments 1p to 4p or a pharmaceutical composition of embodiment 5, for use in a method of treating a pain syndrome, disorder, disease or condition in a mammal.

18p. The compound or pharmaceutical composition of embodiment 17p, wherein the pain syndrome, disorder, disease or condition is characterized by nociceptive pain, neuropathic pain, inflammatory pain, non-inflammatory pain, or pain associated with a chronic condition.

19p. A compound of one of embodiments 1p to 4p or a pharmaceutical composition of embodiment 5, for use in a method of treating ocular glaucoma in a mammal.

20p. A compound of one of embodiments 1p to 4p or a pharmaceutical composition of embodiment 5, for use in preventing or treating gastric or enteric damage caused by an agent.

21p. The compound or pharmaceutical composition of embodiment 20p, wherein the gastric or enteric damage is caused by a non-steroidal anti-inflammatory drug.

22p. The compound or pharmaceutical composition of embodiment 20p, wherein the gastric or enteric damage is caused by aspirin.

1w. A compound, or a pharmaceutically acceptable salt thereof, having the formula:

(I)

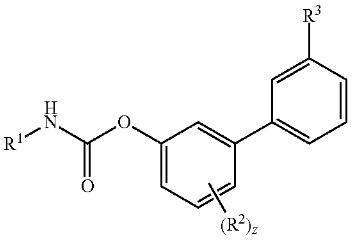

, wherein, $R^1$ is substituted or unsubstituted cycloalkyl, substituted or unsubstituted heterocycloalkyl, substituted or unsubstituted aryl, or substituted or unsubstituted heteroaryl; $R^2$ is independently halogen, $-CX_3$, $-OCX_3$, or $-OCHX_2$; $R^3$ is $-SO_2R^6$, $-SO_2NR^4R^5$, or $-C(O)NR^4R^5$; $R^4$, $R^5$, and $R^6$ are independently hydrogen, substituted or unsubstituted $C_1$-$C_8$ alkyl or substituted or unsubstituted 2 to 8 membered heteroalkyl; where $R^4$ and $R^5$ are optionally joined to form a substituted or unsubstituted 4 to 8 membered heterocycloalkyl or substituted or unsubstituted 5 to 6 membered heteroaryl; the symbol z is an integer from 1 to 4; and X is —F, —Cl, —Br, or —I; with the proviso that the compound is not

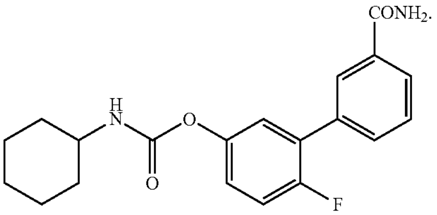

2w. The compound of embodiment 1w, having the formula:

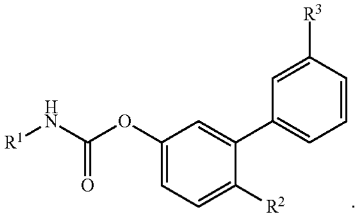

.

3w. The compound of embodiment 1w, having the formula:

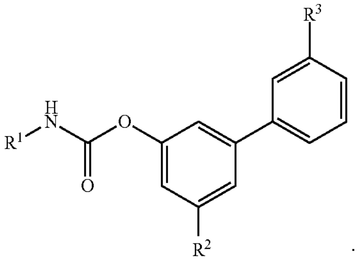

.

4w. The compound of embodiment 1w, having the formula:

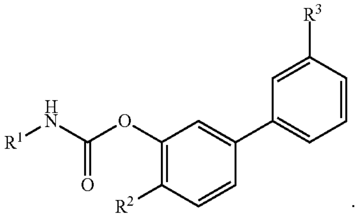

.

5w. The compound of embodiment 1w, having the formula:

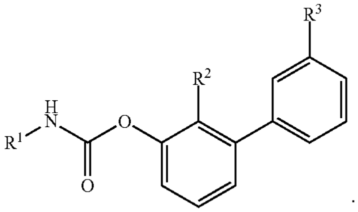

.

6w. The compound of one of embodiments 1w to 5w, wherein $R^1$ is unsubstituted $C_3$-$C_8$ cycloalkyl or unsubstituted 3 to 8 membered heterocycloalkyl.

7w. The compound of one of embodiments 1w to 5w, wherein $R^1$ is unsubstituted $C_6$ cycloalkyl.

8w. The compound of one of embodiments 1w to 7w, wherein $R^2$ is independently halogen, —$OCX_3$, or —$OCHX_2$.

9w. The compound of one of embodiments 1w to 7w, wherein $R^2$ is independently halogen or —$OCHX_2$.

10w. The compound of one of embodiments 1w to 9w, wherein $R^3$ is —$C(O)NR^4R^5$.

11w. The compound of one of embodiments 1w to 9w, wherein $R^3$ is —$SO_2NR^4R^5$.

12w. The compound of one of embodiments 1w to 11w, wherein $R^4$ is hydrogen, unsubstituted $C_1$-$C_4$ alkyl or unsubstituted 2 to 4 membered heteroalkyl.

13w. The compound of one of embodiments 1w to 11w, wherein $R^4$ is hydrogen or unsubstituted $C_1$-$C_4$ alkyl.

14w. The compound of one of embodiments 1w to 13w, wherein $R^5$ is hydrogen, unsubstituted $C_1$-$C_4$ alkyl or unsubstituted 2 to 4 membered heteroalkyl.

15w. The compound of one of embodiments 1w to 13w, wherein $R^5$ is hydrogen or unsubstituted $C_1$-$C_4$ alkyl.

16w. The compound of one of embodiments 1w to 9w, wherein $R^3$ is —$SO_2R^6$.

17w. The compound of embodiment 16w, wherein $R^6$ is unsubstituted $C_1$-$C_4$ alkyl or unsubstituted 2 to 4 membered heteroalkyl.

18w. The compound of embodiment 16w, wherein $R^6$ is unsubstituted methyl.

19w. The compound of one of embodiments 1w to 11w, wherein $R^4$ and $R^5$ are joined to form a substituted or unsubstituted 4 to 8 membered heterocycloalkyl.

20w. The compound of one of embodiments 1w to 19w, wherein the symbol z is 2 to 4.

21w. The compound of embodiment 1w, wherein $R^1$ is cyclobutyl, cyclopentyl, or cyclohexyl; $R^2$ is —F or —$OCHF_2$; $R^3$ is —$SO_2NH_2$, —$SO_2NHMe$, —$SO_2NMe_2$, —$CONH_2$, —CONHMe, —$CONMe_2$, or —$SO_2Me$; and z is 1.

22w. The compound of embodiment 1w, wherein $R^1$ is cyclobutyl, cyclopentyl, or cyclohexyl; $R^2$ is —F or —$OCHF_2$; and $R^3$ is —$SO_2NH_2$, —$SO_2NHMe$, —$SO_2NMe_2$, —$CONH_2$, —CONHMe, —$CONMe_2$, or —$SO_2Me$.

23w. The compound of one of embodiments 1w to 22w, wherein the compound is not

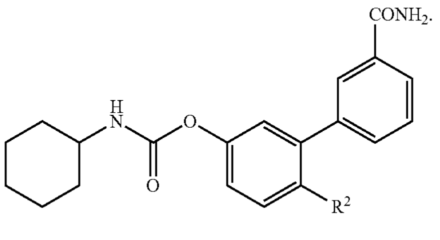

24w. The compound of embodiment 1w, wherein the compound is

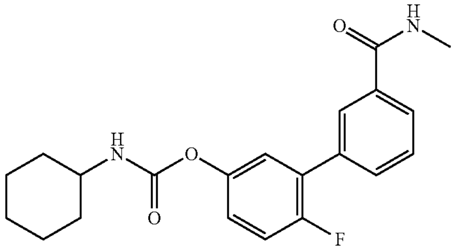

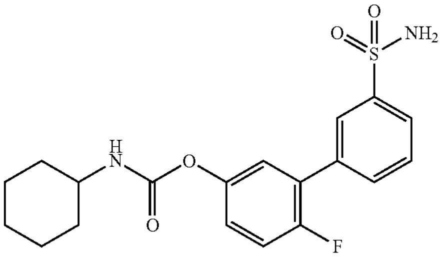

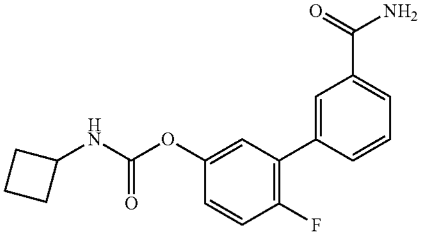

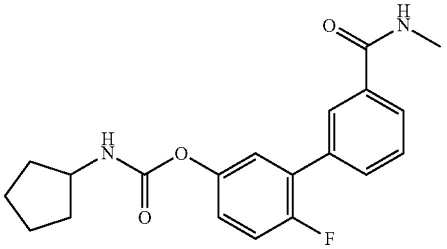

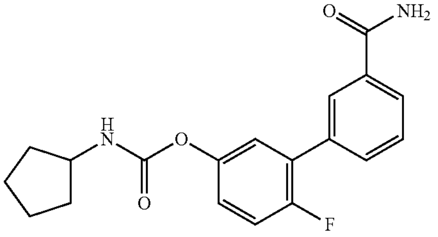

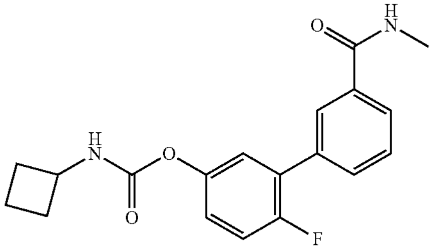

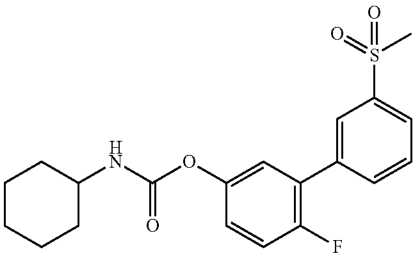

-continued

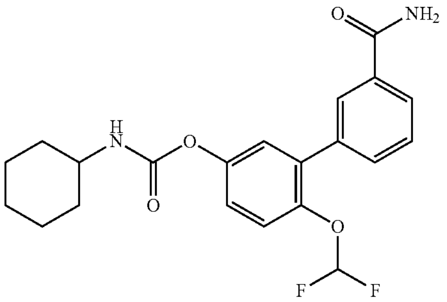

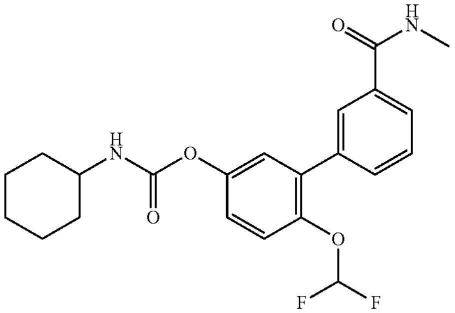

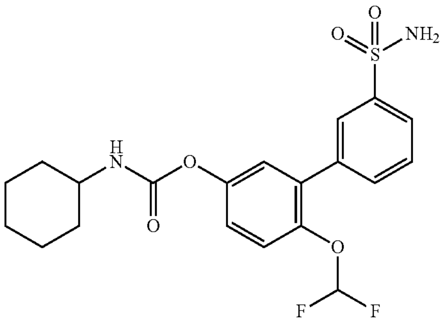

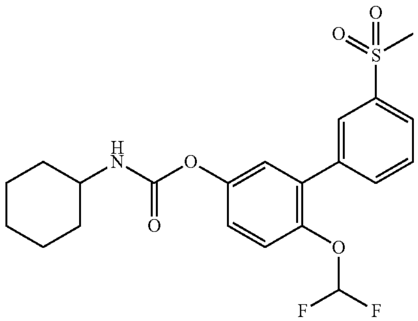

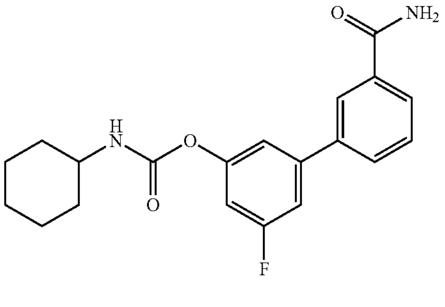

or

-continued

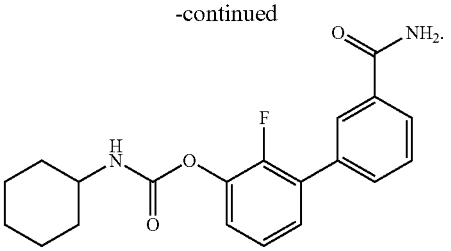

25w. The compound of one of embodiments 1w to 24w, wherein the compound has an oral bioavailability of greater than 35% in a subject.

26w. The compound of one of embodiments 1w to 24w, wherein the compound has an oral bioavailability of greater than 85% in a subject.

27w. The compound of one of embodiments 1w to 24w, wherein the compound has an oral bioavailability of greater than 95% in a subject.

28w. A pharmaceutical composition comprising a pharmaceutically acceptable excipient and a compound, or a pharmaceutically acceptable salt thereof, of one of embodiments 1w to 27w.

29w. A compound, or a pharmaceutically acceptable salt thereof, for use in treating or preventing reduced appetite, gastric damage, enteric damage, a nicotine use disorder, tobacco smoking, substance abuse, a *cannabis* use disorder, a cocaine use disorder, an opioid use disorder, an amphetamine use disorder, a methamphetamine use disorder, an alcohol use disorder, an eating disorder, anxiety, post-traumatic stress disorder, schizophrenia, a mood disorder, pain, inflammation, or ocular glaucoma, wherein the compound has the formula:

(I)

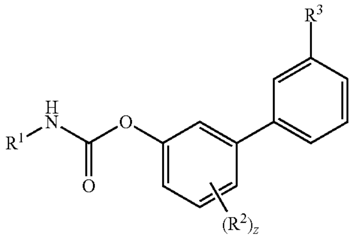

, wherein, $R^1$ is substituted or unsubstituted cycloalkyl, substituted or unsubstituted heterocycloalkyl, substituted or unsubstituted aryl, or substituted or unsubstituted heteroaryl; $R^2$ is independently halogen, $-CX_3$, $-OCX_3$, $-OCHX_2$, substituted or unsubstituted $C_1$-$C_8$ alkyl, or substituted or unsubstituted 2 to 8 membered heteroalkyl; $R^3$ is $-SO_2R^6$, $-SO_2NR^4R^5$, or $-C(O)NR^4R^5$; $R^4$, $R^5$, and $R^6$ are independently hydrogen, substituted or unsubstituted $C_1$-$C_8$ alkyl or substituted or unsubstituted 2 to 8 membered heteroalkyl; where $R^4$ and $R^5$ are optionally joined to form a substituted or unsubstituted 4 to 8 membered heterocycloalkyl or substituted or unsubstituted 5 to 6 membered heteroaryl; the symbol z is an integer from 1 to 4; and X is —F, —Cl, —Br, or —I.

30w. The compound of embodiment 29w, wherein said *cannabis* use disorder is *cannabis* craving, *cannabis* addiction, *cannabis* dependence, or *cannabis* withdrawal.

31w. The compound of embodiment 29w, wherein said cocaine use disorder is cocaine craving, cocaine addiction, cocaine dependence, or cocaine withdrawal.

32w. The compound of embodiment 29w, wherein said opioid use disorder is opioid craving, opioid addiction, opioid dependence, or opioid withdrawal.

33w. The compound of embodiment 29w, wherein said opiate use disorder is opiate craving, opiate addiction, opiate dependence, or opiate withdrawal.

34w. The compound of embodiment 29w, wherein said amphetamine use disorder is amphetamine craving, amphetamine addiction, amphetamine dependence, or amphetamine withdrawal.

35w. The compound of embodiment 29w, wherein said methamphetamine use disorder is methamphetamine craving, methamphetamine addiction, methamphetamine dependence, or methamphetamine withdrawal.

36w. The compound of embodiment 29w, wherein said alcohol use disorder is alcohol craving, alcohol addiction, alcohol dependence, alcohol withdrawal, or alcohol induced delirium.

37w. The compound of embodiment 29w, wherein said eating disorder is bulimia nervosa, anorexia nervosa, a binge eating disorder, or an eating disorder not otherwise specified (EDNOS).

38w. The compound of embodiment 29w, wherein said mood disorder is bipolar disorder type I, bipolar disorder type II, cyclothymia, substance-induced mood disorder, depression, atypical depression, psychotic major depression, post-partum depression, dysthymia, catatonic depression, melancholic depression, or a depressive disorder not otherwise specified (DDNOS).

39w. The compound of embodiment 29w, wherein said pain is nociceptive pain, neuropathic pain, inflammatory pain, non-inflammatory pain, or pain associated with a chronic condition.

40w. The compound of embodiment 29w, wherein said gastric or enteric damage is caused by a non-steroidal anti-inflammatory drug.

41w. A compound, or a pharmaceutically acceptable salt thereof, for use in modulating the level of a fatty acid ethanolamide (FAE) in a subject, wherein the compound has the formula:

(I)

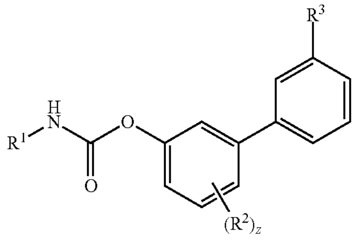

, wherein, $R^1$ is substituted or unsubstituted cycloalkyl, substituted or unsubstituted heterocycloalkyl, substituted or unsubstituted aryl, or substituted or unsubstituted heteroaryl; $R^2$ is independently halogen, $—CX_3$, $—OCX_3$, $—OCHX_2$, substituted or unsubstituted $C_1$-$C_8$ alkyl, or substituted or unsubstituted 2 to 8 membered heteroalkyl; $R^3$ is $—SO_2R^6$, $—SO_2NR^4R^5$, or $—C(O)NR^4R^5$; $R^4$, $R^5$, and $R^6$ are independently hydrogen, substituted or unsubstituted $C_1$-$C_8$ alkyl or substituted or unsubstituted 2 to 8 membered heteroalkyl; where $R^4$ and $R^5$ are optionally joined to form a substituted or unsubstituted 4 to 8 membered heterocycloalkyl or substituted or unsubstituted 5 to 6 membered heteroaryl; the symbol z is an integer from 1 to 4; and X is —F, —Cl, —Br, or —I.

42w. The compound of embodiment 41w, wherein the FAE is anandamide.

43w. The compound of embodiment 41w, wherein the FAE is oleoylethanolamide.

44w. The compound of embodiment 41w, wherein the FAE is palmitoylethanolamide.

45w. A compound, or a pharmaceutically acceptable salt thereof, for use in modulating the level of activity of FAAH in a subject, wherein the compound has the formula:

(I)

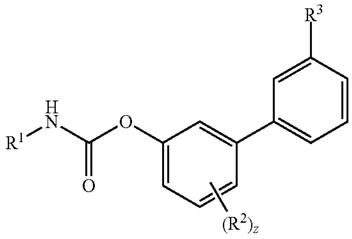

, wherein, $R^1$ is substituted or unsubstituted cycloalkyl, substituted or unsubstituted heterocycloalkyl, substituted or unsubstituted aryl, or substituted or unsubstituted heteroaryl; $R^2$ is independently halogen, $—CX_3$, $—OCX_3$, $—OCHX_2$, substituted or unsubstituted $C_1$-$C_8$ alkyl, or substituted or unsubstituted 2 to 8 membered heteroalkyl; $R^3$ is $—SO_2R^6$, $—SO_2NR^4R^5$, or $—C(O)NR^4R^5$; $R^4$, $R^5$, and $R^6$ are independently hydrogen, substituted or unsubstituted $C_1$-$C_8$ alkyl or substituted or unsubstituted 2 to 8 membered heteroalkyl; where $R^4$ and $R^5$ are optionally joined to form a substituted or unsubstituted 4 to 8 membered heterocycloalkyl or substituted or unsubstituted 5 to 6 membered heteroaryl; the symbol z is an integer from 1 to 4; and X is —F, —Cl, —Br, or —I.

46w. The compound of one of embodiments 29w to 45w, having the formula:

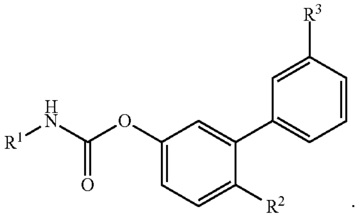

.

47w. The compound of one of embodiments 29w to 45w, having the formula:

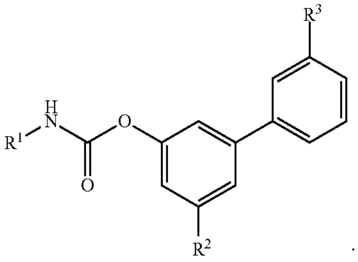

.

48w. The compound of one of embodiments 29w to 45w, having the formula:

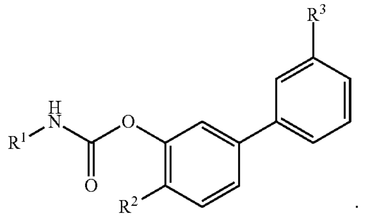

49w. The compound of one of embodiments 29w to 45w, having the formula:

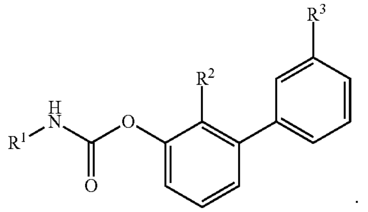

50w. The compound of one of embodiments 29w to 49w, wherein $R^1$ is unsubstituted $C_3$-$C_8$ cycloalkyl or unsubstituted 3 to 8 membered heterocycloalkyl.

51w. The compound of one of embodiments 29w to 49w, wherein $R^1$ is unsubstituted $C_6$ cycloalkyl.

52w. The compound of one of embodiments 29w to 51w, wherein $R^2$ is independently halogen, $-CX_3$, $-OCX_3$, $-OCHX_2$, substituted or unsubstituted $C_1$-$C_4$ alkyl, or substituted or unsubstituted 2 to 4 membered heteroalkyl.

53w. The compound of one of embodiments 29w to 51w, wherein $R^2$ is independently halogen or $-OCHX_2$.

54w. The compound of one of embodiments 29w to 53w, wherein $R^3$ is $-C(O)NR^4R^5$.

55w. The compound of one of embodiments 29w to 53w, wherein $R^3$ is $-SO_2NR^4R^5$.

56w. The compound of one of embodiments 29w to 55w, wherein $R^4$ is hydrogen, unsubstituted $C_1$-$C_4$ alkyl or unsubstituted 2 to 4 membered heteroalkyl.

57w. The compound of one of embodiments 29w to 55w, wherein $R^4$ is hydrogen or unsubstituted $C_1$-$C_4$ alkyl.

58w. The compound of one of embodiments 29w to 57w, wherein $R^5$ is hydrogen, unsubstituted $C_1$-$C_4$ alkyl or unsubstituted 2 to 4 membered heteroalkyl.

59w. The compound of one of embodiments 29 to 57w, wherein $R^5$ is hydrogen or unsubstituted $C_1$-$C_4$ alkyl.

60w. The compound of one of embodiments 29w to 53w, wherein $R^3$ is $-SO_2R^6$.

61w. The compound of embodiment 60w, wherein $R^6$ is unsubstituted $C_1$-$C_4$ alkyl or unsubstituted 2 to 4 membered heteroalkyl.

62w. The compound of embodiment 60w, wherein $R^6$ is unsubstituted methyl.

63w. The compound of one of embodiments 29 to 59w, wherein $R^4$ and $R^5$ are joined to form a substituted or unsubstituted 4 to 8 membered heterocycloalkyl.

64w. The compound of one of embodiments 29w to 63w, wherein the symbol z is 1.

65w. The compound of one of embodiments 29w to 45w, wherein $R^1$ is cyclobutyl, cyclopentyl, or cyclohexyl; $R^2$ is $-F$ or $-OCHF_2$; $R^3$ is $-SO_2NH_2$, $-SO_2NHMe$, $-SO_2NMe_2$, $-CONH_2$, $-CONHMe$, $-CONMe_2$, or $-SO_2Me$; and z is 1.

66w. The compound of one of embodiments 29w to 45w, wherein $R^1$ is cyclobutyl, cyclopentyl, or cyclohexyl; $R^2$ is $-F$ or $-OCHF_2$; and $R^3$ is $-SO_2NH_2$, $-SO_2NHMe$, $-SO_2NMe_2$, $-CONH_2$, $-CONHMe$, $-CONMe_2$, or $-SO_2Me$.

67w. The compound of one of embodiments 29w to 66w, wherein the compound is not

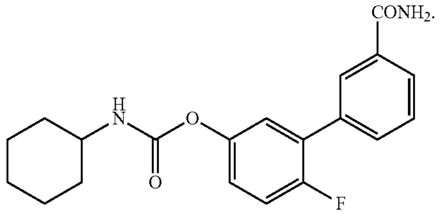 [SMILES: NC(=O)c1cccc(-c2cc(OC(=O)NC3CCCCC3)ccc2F)c1]

68w. The compound of one of embodiments 29w to 66w, wherein the compound is not

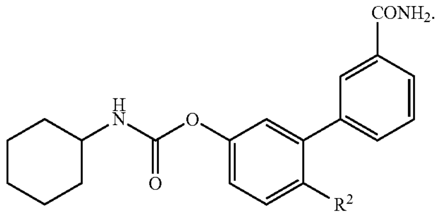

69w. The compound of one of embodiments 29w to 45w, wherein the compound is

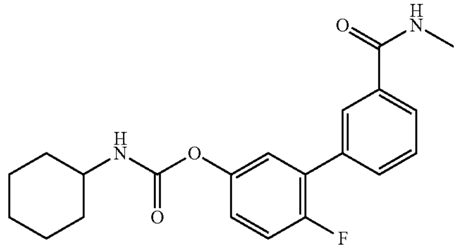 [SMILES: CNC(=O)c1cccc(-c2cc(OC(=O)NC3CCCCC3)ccc2F)c1]

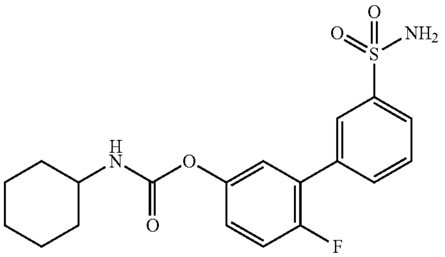 [SMILES: NS(=O)(=O)c1cccc(-c2cc(OC(=O)NC3CCCCC3)ccc2F)c1]

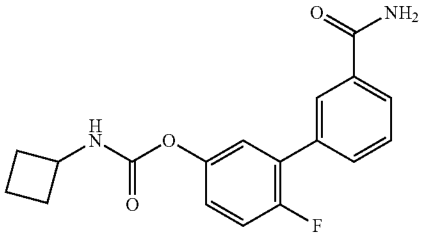 [SMILES: NC(=O)c1cccc(-c2cc(OC(=O)NC3CCC3)ccc2F)c1]

-continued

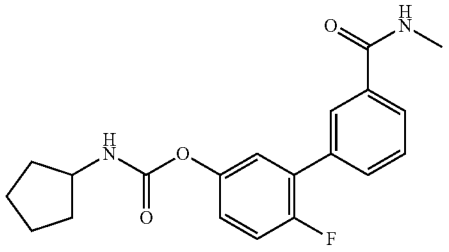 [SMILES: CNC(=O)c1cccc(-c2cc(OC(=O)NC3CCCC3)ccc2F)c1]

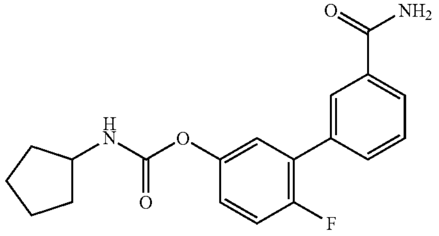 [SMILES: NC(=O)c1cccc(-c2cc(OC(=O)NC3CCCC3)ccc2F)c1]

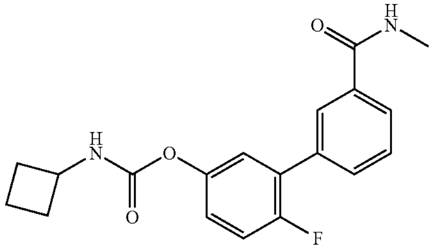 [SMILES: CNC(=O)c1cccc(-c2cc(OC(=O)NC3CCC3)ccc2F)c1]

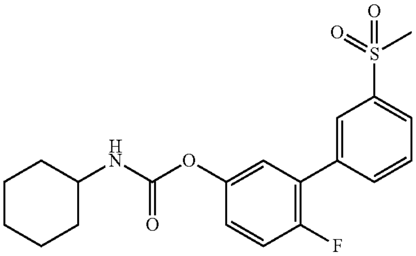 [SMILES: CS(=O)(=O)c1cccc(-c2cc(OC(=O)NC3CCCCC3)ccc2F)c1]

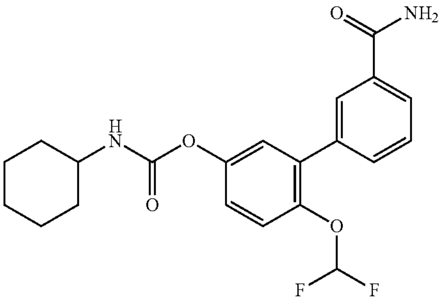

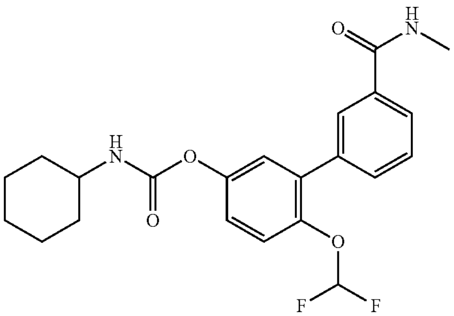

-continued

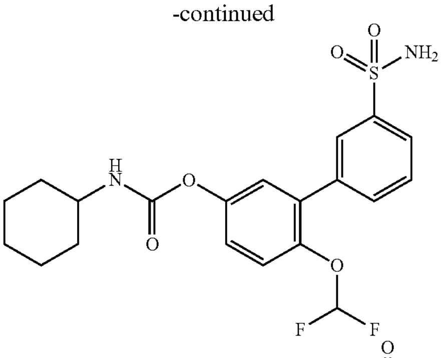

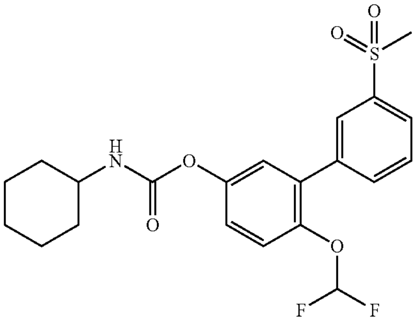

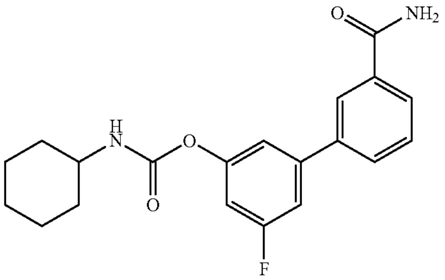

or

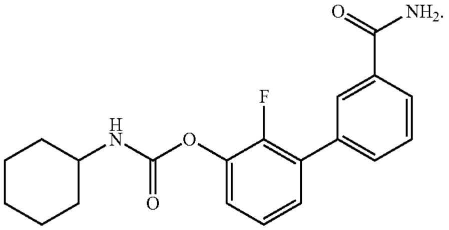

70w. The compound of one of embodiments 29w to 69w, wherein the compound has an oral bioavailability of greater than 35% in a subject.

71w. The compound of one of embodiments 29w to 69w, wherein the compound has an oral bioavailability of greater than 85% in a subject.

72w. The compound of one of embodiments 29w to 69w, wherein the compound has an oral bioavailability of greater than 95% in a subject.

EXAMPLES

Preparative Examples

The compounds reported in Table 1 were synthesized as described below. Abbreviations used in the description of the synthesis of the compounds reported in Table 1 are as follows: acetonitrile (MeCN), ammonium chloride ($NH_4Cl$), cesium acetate (CsOAc), chloroform ($CHCl_3$), cyclohexane (Cy), deuterated chloroform (chloroform-d), diatomaceous earth (Celite), deuterated dimethylsulfoxide (DMSO-$d_6$), dichloromethane (DCM), 2-dicyclohexylphosphino-2',6'-dimethoxybiphenyl (Sphos), dimethylsulfoxide (DMSO), ethylene glycol monomethyl ether (EGME), N,N-diisopropylethylamine (DIPEA), 4-dimethylaminopyridine (DMAP), N,N-dimethylformamide (DMF), ethanol (EtOH), electrospray (ES), ethyl acetate (EtOAc), hydrochloric acid (HCl), mass spectrometry (MS), potassium hydroxide (KOH), nitrogen ($N_2$), methanol (MeOH), 2-methyltetrahydrofuran (2-MeTHF), nuclear magnetic resonance (NMR), [1,1'-bis(diphenylphosphino)ferrocene]dichloropalladium(II) ($PdCl_2$(dppf)), palladium acetate ($Pd(OAc)_2$), palladium on carbon (Pd/C), pyridine (Py), potassium carbonate ($K_2CO_3$), room temperature (RT), $R_t$ (retention time), silica gel ($SiO_2$), sodium sulphate ($Na_2SO_4$), tetrahydrofuran (THF), thin layer chromatography (TLC), triethylamine ($Et_3N$).

General Purification and Analytical Methods

Automated column chromatography purifications were done using a Teledyne ISCO apparatus (CombiFlash® Rf) with pre-packed silica gel columns of different sizes (from 4 g until 120 g). Mixtures of increasing polarity of cyclohexane and ethyl acetate or dichloromethane and methanol were used as eluents. Preparative TLCs were performed using Macherey-Nagel pre-coated 0.05 mm TLC plates (SIL G-50 UV254). Microwave heating was performed using Explorer®-48 positions instrument (CEM). NMR experiments were run on a Bruker Avance III 400 system (400.13 MHz for $^1$H), equipped with a BBI probe and Z-gradients. Spectra were acquired at 300 K, using deuterated dimethylsulfoxide (DMSO-$d_6$) or deuterated chloroform (chloroform-d) as solvents. Chemical shifts for $^1$H were recorded in parts per million using the residual non-deuterated solvent as the internal standard (for chloroform-d: 7.26 ppm; for DMSO-$d_6$: 2.50 ppm, $^1$H). UPLC-MS analyses were run on a Waters ACQUITY UPLC-MS system consisting of a SQD (Single Quadrupole Detector) Mass Spectrometer equipped with an Electrospray Ionization interface and a Photodiode Array Detector. The PDA range was 210-400 nm. The analyses were run on an ACQUITY UPLC BEH $C_{18}$ column (50×2.1 mmID, particle size 1.7 μm) with a Vanguard BEH $C_{18}$ pre column (5×2.1 mmID, particle size 1.7 μm). The mobile phase was: (A) 10 mM $NH_4OAc$ in $H_2O$ at pH 5 adjusted with AcOH; (B) 10 mM $NH_4OAc$ in $MeCN/H_2O$ (95:5) at pH 5. Analyses were performed using the following method: gradient 5 to 95% B over 3 min; flow rate 0.5 mL/min; temperature 40° C. Electrospray ionization in positive and negative mode was applied in the mass scan range 100-500 Da.

Synthesis of 3-(2-fluoro-5-hydroxy-phenyl)-N-methyl-benzamide (IIIa)

A teflon capped vial was charged with Va (191 mg, 1.00 mmol), $Pd(OAc)_2$ (11.2 mg, 0.05 mmol), S-Phos (41.1 mg, 0.10 mmol), $K_3PO_4$ (425 mg, 2.00 mmol) and N-methyl-3-(4,4,5,5-tetramethyl-1,3,2-dioxaborolan-2-yl)benzamide (392 mg, 1.50 mmol). The vial was sealed, then evacuated and backfilled with $N_2$ (×3 times). To the solids was added $THF/H_2O$ (5 mL, 10:1). The reaction was heated at 50° C. for 2 h, then cooled to RT, diluted with EtOAc and washed with a saturated aqueous $NH_4Cl$ solution (10 mL). The aqueous solution was extracted with EtOAc (3×20 mL). The combined organic layers were washed with brine, dried ($Na_2SO_4$) and concentrated. The residue was purified by flash chromatography ($SiO_2$) eluting with a gradient of 0 to 50% EtOAc in Cy to afford the title compound as an off-white powder, 216 mg (88%). $^1$H NMR (400 MHz, chloroform-d, 300K) δ 7.86 (s, 1H), 7.68 (d, J=7.7 Hz, 1H), 7.60 (d, J=7.6 Hz, 1H), 7.40 (t, J=7.7 Hz, 1H), 6.97 (t, J=9.5 Hz, 1H), 6.90-6.86 (m, 1H), 6.85-6.78 (m, 1H), 6.65-6.59 (m, 1H), 3.01 (d, J=4.8 Hz, 3H). UPLC-MS: Rt 1.78 min; MS (ES): m/z 246 $[M+H]^+$.

Synthesis of 3-(2-fluoro-5-hydroxy-phenyl)benzenesulfonamide

A teflon capped vial was charged with Va (191 mg, 1.00 mmol), $Pd(OAc)_2$ (11.2 mg, 0.05 mmol), S-Phos (41.1 mg, 0.10 mmol), $K_3PO_4$ (425 mg, 2.00 mmol) and 3-(4,4,5,5-tetramethyl-1,3,2-dioxaborolan-2-yl)benzenesulfonamide (425 mg, 1.50 mmol). The vial was sealed, then evacuated and backfilled with $N_2$ (×3 times). To the solids was added $THF/H_2O$ (5 mL, 10:1). The reaction was heated at 50° C. for 2 h, then cooled to RT, diluted with EtOAc and washed with a saturated aqueous $NH_4Cl$ solution (5 mL). The combined organic layers were washed with brine, dried ($Na_2SO_4$) and concentrated in vacuo. The residue was purified by flash chromatography ($SiO_2$) eluting with a gradient of 0 to 30% EtOAc in Cy to afford the title compound as an off-white powder, 194 mg (73%). $^1$H NMR (400 MHz, DMSO-$d_6$, 300K) δ 9.61 (s, 1H), 7.99-7.94 (m, 1H), 7.87-7.82 (m, 1H), 7.77-7.71 (m, 1H), 7.67 (t, J=7.7 Hz, 1H), 7.43 (s, 2H), 7.16 (dd, J=10.5, 8.9 Hz, 1H), 6.89 (dd, J=6.5, 3.0 Hz, 1H), 6.86-6.81 (m, 1H). UPLC-MS: Rt 1.74 min; MS (ES): m/z 266 $[M-H]^-$.

Synthesis of 4-fluoro-3-(3-methylsulfonylphenyl)phenol (IIIc)

A teflon capped vial was charged with Va (95 mg, 0.5 mmol), $Pd(OAc)_2$ (1.1 mg, 0.005 mmol), $K_3PO_4$ (171.9 mg, 1.24 mmol) and (3-methylsulfonylphenyl)boronic acid (149.2 mg, 0.75 mmol). The vial was sealed, then evacuated and backfilled with $N_2$ (×3 times). To the solids was added $EGME/H_2O$ (4 mL, 3:1). The reaction mixture was stirred 10 min at RT, then quenched with 2N HCl (5 mL). The aqueous solution was extracted with DCM (10 mL), dried ($Na_2SO_4$) and concentrated. The residue was purified by flash chromatography ($SiO_2$) eluting with a gradient of 0 to 8% MeOH in DCM to afford the title compound as colourless powder (82 mg, 62%). UPLC-MS: Rt 1.91 min; MS (ES): m/z 265 $[M-H]^-$.

Synthesis of 3-[5-benzyloxy-2-(difluoromethoxy)phenyl]benzamide (IIId')

To a solution of Vb' (200 mg, 0.61 mmol) in EGME (2.5 mL), $H_2O$ (0.6 mL) was added drop wise, followed by the addition of $K_2CO_3$ (168 mg, 1.22 mmol), 3-carbamoylbenzeneboronic acid (150.5 mg, 0.9 mmol) and $Pd(OAc)_2$ (0.7 mg, 0.003 mmol). The reaction mixture was stirred at RT for 20 min. $H_2O$ (7 mL) and DCM (7 mL) were then added and the mixture was vigorously stirred for 20 min then the two phases were separated. The organic layer was dried ($Na_2SO_4$) and concentrated. The residue was purified by flash chromatography ($SiO_2$) eluting with a gradient of 50 to 100% EtOAc in Cy to afford the title compound as a colorless oil (214 mg, 0.58 mmol, 95%). $^1$H NMR (400 MHz, DMSO-$d_6$) δ 8.02 (bs, 1H), 8.00-7.95 (m, 1H), 7.93-7.85 (m, 1H), 7.67-7.61 (m, 1H), 7.53 (t, J=7.7 Hz, 1H), 7.50-7.31 (m, 7H), 7.26 (d, J=8.8 Hz, 1H), 7.17-7.13 (m, 1H), 7.13-7.08 (m, 1H), 6.98 (t, J=74.3 Hz, 1H), 5.18 (s, 2H). UPLC-MS: Rt 2.60 min; MS (ES) m/z 370 $[M+H]^+$.

Synthesis of 3-[5-benzyloxy-2-(difluoromethoxy) phenyl]-N-methyl-benzamide (IIIe')

To a solution of Vb' (147 mg, 0.45 mmol) in THF (3.0 mL), $H_2O$ (0.6 mL) was added drop wise, followed by the addition of $K_3PO_4$ (118 mg, 1.12 mmol), N-methyl-3-(4,4,5,5-tetramethyl-1,3,2-dioxaborolan-2-yl)benzamide (161 mg, 0.63 mmol), $Pd(OAc)_2$ (3 mg, 0.011 mmol) and SPhos (11 mg, 0.027 mmol). The mixture was heated at 65° C. for 2 h. After cooling to RT, $H_2O$ (5 mL) and DCM (10 mL) were then added and the mixture was vigorously stirred for 20 min then the two phases were separated. The organic layer was dried ($Na_2SO_4$) and concentrated. The residue was purified by flash chromatography ($SiO_2$) eluting with a gradient of 20 to 80% EtOAc in Cy to afford the title compound as a colorless oil (153 mg, 0.40 mmol, 89%). $^1H$ NMR (400 MHz, Chloroform-d) δ 8.55-8.43 (m, 1H), 7.93-7.90 (m, 1H), 7.88-7.81 (m, 1H), 7.67-7.59 (m, 1H), 7.53 (t, J=7.7 Hz, 1H), 7.50-7.31 (m, 5H), 7.26 (d, J=8.8 Hz, 1H), 7.16-7.07 (m, 2H), 6.98 (t, J=74.2 Hz, 1H), 5.17 (s, 2H), 2.80 (d, J=4.5 Hz, 3H). UPLC-MS: Rt 2.71 min; MS (ES) m/z 384 $[M+H]^+$.

Synthesis of 3-[5-benzyloxy-2-(difluoromethoxy) phenyl]benzenesulfonamide (IIIf')

To a solution of Vb' (182 mg, 0.55 mmol) in 1,4-dioxane (7.5 mL), $H_2O$ (1.5 mL) was added drop wise, followed by the addition of $K_3PO_4$ (294 mg, 1.38 mmol), 3-(4,4,5,5-tetramethyl-1,3,2-dioxaborolan-2-yl)benzenesulfonamide (170 mg, 0.72 mmol), $Pd(OAc)_2$ (3.7 mg, 0.017 mmol) and SPhos (14 mg, 0.033 mmol). The mixture was heated at 65° C. for 2 h. After cooling to RT, $H_2O$ (5 mL) and DCM (10 mL) were then added and the mixture was vigorously stirred for 20 min then the two phases were separated. The organic layer was dried ($Na_2SO_4$) and concentrated. The residue was purified by flash chromatography ($SiO_2$) eluting with a gradient of 0 to 40% EtOAc in Cy to afford the title compound as a colorless oil (106 mg, 0.28 mmol, 46%). $^1H$ NMR (400 MHz, DMSO-$d_6$) δ 7.91 (t, J=1.7 Hz, 1H), 7.84 (dt, J=7.6, 1.7 Hz, 1H), 7.75-7.61 (m, 2H), 7.51-7.22 (m, 8H), 7.17-7.07 (m, 2H), 7.00 (t, J=74.0 Hz, 1H), 5.16 (s, 2H). UPLC-MS: Rt 2.61 min; MS (ES) m/z 370 $[M+H]^+$.

Synthesis of 4-benzyloxy-1-(difluoromethoxy)-2-(3-methylsulfonylphenyl)benzene (IIIg')

To a solution of Vb' (105 mg, 0.32 mmol) in EGME (3.0 mL), $H_2O$ (0.7 ml) was added drop wise, followed by the addition of $K_2CO_3$ (88.2 mg, 0.64 mmol), (3-methylsulfonylphenyl)boronic acid (76.6 mg, 0.38 mmol) and $Pd(OAc)_2$ (0.9 mg, 0.004 mmol). The mixture was heated at 65° C. for 1 h. After cooling to RT, $H_2O$ (5 mL) and DCM (10 mL) were then added and the mixture was vigorously stirred for 20 min then the two phases were separated. The organic layer was dried ($Na_2SO_4$) and concentrated. The residue was purified by flash chromatography ($SiO_2$) eluting with a gradient of 0 to 50x % EtOAc in Cy to afford the title compound as a colorless oil (129.3 mg, 0.31 mmol, 99%). $^1H$ NMR (400 MHz, DMSO-$d_6$) δ 8.02-7.99 (m, 1H), 7.98-7.92 (m, 1H), 7.89-7.83 (m, 1H), 7.75 (t, J=7.8 Hz, 1H), 7.54-7.19 (m, 7H), 7.15 (dd, J=9.0, 3.0 Hz, 1H), 7.04 (t, J=74.0 Hz, 1H), 5.19 (s, 2H), 3.26 (s, 3H). UPLC-MS: Rt 2.84 min; MS (ES) m/z 422 $[M+NH_4]^+$.

Synthesis of 3-(3-benzyloxy-5-fluoro-phenyl)benzamide (IIIh')

A teflon capped vial was charged with Vc' (124 mg, 0.44 mmol), $Pd(OAc)_2$ (1 mg, 0.0044 mmol), $K_3PO_4$ (152.5 mg, 1.10 mmol) and (3-carbamoylphenyl)boronic acid (109.2 mg, 0.66 mmol). The vial was sealed, then evacuated and backfilled with $N_2$ (×3 times). To the solids was added EGME/$H_2O$ (4 mL, 3:1). The reaction mixture was stirred 10 min at RT, and then quenched with 2N HCl. The aqueous solution was extracted with DCM (10 mL), dried ($Na_2SO_4$) and concentrated to afford the title compound as a white powder, which was used in the next step without further purification. $^1H$ NMR (400 MHz, chloroform-d) δ 8.03 (t, J=1.8 Hz, 1H), 7.83-7.79 (m, 1H), 7.76-7.70 (m, 1H), 7.55 (t, J=7.7 Hz, 1H), 7.49-7.45 (m, 2H), 7.44-7.41 (m, 2H), 7.41-7.36 (m, 1H), 7.05 (t, J=1.6 Hz, 1H), 6.98-6.93 (m, 1H), 6.74 (dt, J=10.4, 2.3 Hz, 1H), 5.92 (d, J=159.6 Hz, 2H), 5.14 (s, 2H). UPLC-MS: Rt 2.63 min; MS (ES): m/z 322 $[M+H]^+$.

Synthesis of 3-(3-Fluoro-5-hydroxy-phenyl)benzamide (IIIh)

A teflon capped vial was charged with IIIh' (70 mg, 0.22 mmol), and 10% Pd/C (70 mg). The vial was sealed, then evacuated and backfilled with $N_2$ (×3 times). To the solids was added 1,4-dioxane/EtOH (6 mL) and cyclohexene (2.2 mL) and the reaction was stirred 3 h at 80° C. The reaction mixture was then cooled to RT and the catalyst was filtered off and the solution was concentrated. The residue was used in the next step without further purification. UPLC-MS: Rt 1.73 min; MS (ES): m/z 232 $[M+H]^+$.

Synthesis of 3-(2-fluoro-3-hydroxy-phenyl)benzamide

A teflon capped vial was charged with Vd (200 mg, 1.05 mmol), $PdCl_2dppf$ (38 mg, 0.05 mmol, 5 mol %), $K_3PO_4$ (445 mg, 2.09 mmol) and (3-carbamoylphenyl)boronic acid (259 mg, 1.57 mmol). The vial was sealed, then evacuated and backfilled with $N_2$ (×3 times). To the solids was added 1,4-dioxane/EtOH (6 mL, 2:1). The mixture was heated under microwave irradiation at 100° C. for 1 h. then cooled to RT, diluted with EtOAc (20 mL) and washed with $H_2O$ (20 mL). The aqueous phase was extracted with EtOAc (20 mL) and with DCM (20 mL). The combined organic phases were dried ($Na_2SO_4$) and concentrated. The residue was purified by flash chromatography ($SiO_2$) eluting with 0 to 5% MeOH in DCM. The title compound was obtained as a light yellow powder, 70 mg (29%). $^1H$ NMR (400 MHz, DMSO-$d_6$) δ 9.95 (s, 1H), 8.06 (s, 1H), 8.02 (d, J=1.5 Hz, 1H), 7.89 (dt, J=7.7, 1.4 Hz, 1H), 7.67 (dq, J=7.6, 1.6 Hz, 1H), 7.55 (t, J=7.7 Hz, 1H), 7.41 (s, 1H), 7.09 (td, J=8.0, 1.0 Hz, 1H), 7.00 (td, J=8.1, 1.7 Hz, 1H), 6.94 (ddd, J=7.7, 6.7, 1.8 Hz, 1H). UPLC-MS: $R_t$ 1.62 min, MS (ES): m/z 230.1 $[M-H]^-$.

Synthesis of 4-benzyloxy-2-bromo-1-(difluoromethoxy)benzene (Vb')

To a cooled (−10° C.) solution of 4-benzyloxy-2-bromophenol (1.3 g, 4.6 mmol) in MeCN/$H_2O$ (50 mL, 1:1) KOH (5.1 g, 91.8 mmol) was added. After 20 min diethyl(bromodifluoromethyl)phosphonate (1.2 ml, 6.9 mmol) was added and the mixture was stirred at −10° C. for 20 min, then at RT for 2 h. DCM (100 mL) and $H_2O$ (50 ml) were then added and the mixture was vigorously stirred for 20 min then the two phases were separated. The organic layer was dried ($Na_2SO_4$) and concentrated. The residue was used in the next step without further purification; colorless oil. $^1H$ NMR (400 MHz, chloroform-d) δ 7.50-7.33 (m, 5H), 7.26 (d, J=2.9 Hz, 1H), 7.17 (d, J=9.0 Hz, 1H), 6.92 (dd, J=9.0, 2.9 Hz, 1H), 6.46 (t, J=74.0 Hz, 1H), 5.06 (s, 2H). UPLC-MS: Rt 3.08 min; MS (ES) m/z 327, 329 $[M-H]^-$.

Synthesis of (3-bromo-4-fluoro-phenyl)N-cyclopentylcarbamate (VIb)

A teflon capped vial was charged with Va (1 g; 5.265 mmol) and triphosgene (516 mg; 1.737 mmol). The vial was sealed, then evacuated and backfilled with $N_2$ (×3 times). To the solids was added dry DCM (5.0 mL), and the reaction was cooled to 0° C. Then Py (416 mg; 5.265 mmol) in dry DCM (7 mL) was slowly added and the reaction was stirred at RT for 1 h. Cyclopentylamine (148 mg; 1.739; 1 eq) and Py (138 mg; 1.739; 1 eq) in dry DCM (6 mL) were then added and the reaction stirred at RT for 3 h and then quenched with 1N HCl. The aqueous solution was extracted with EtOAc (20 mL), dried ($Na_2SO_4$) and concentrated. The residue was purified by flash chromatography ($SiO_2$) eluting with a gradient of 0 to 10% EtOAc in Cy to afford the title compound as a white powder (307 mg, 58%). $^1H$ NMR (400 MHz, chloroform-d) δ 7.39 (dd, J=5.8, 2.5 Hz, 1H), 7.16-7.04 (m, 2H), 4.97 (s, 1H), 4.07 (h, J=6.9 Hz, 1H), 2.14-1.96 (m, 2H), 1.88-1.61 (m, 4H), 1.56-1.40 (m, 2H). UPLC-MS: $R_t$ 2.71 min; MS (ES): m/z 302 $[M+H]^+$.

Synthesis of (3-bromo-4-fluoro-phenyl)N-cyclobutylcarbamate (VIc)

A teflon capped vial was charged with Va (1 g; 5.265 mmol) and triphosgene (516 mg; 1.737 mmol). The vial was sealed, then evacuated and backfilled with $N_2$ (×3 times). To the solids was added dry DCM (5.0 mL), and the reaction was cooled to 0° C. Then Py (416 mg; 5.265 mmol) in dry DCM (7 mL), was slowly added and the reaction was stirred at RT for 1 h. Cyclobutylamine (124 mg; 1.739) and Py (138 mg; 1.739) in dry DCM (6 mL), were then added and the reaction stirred at RT for 3 h, then quenched with 1N HCl. The aqueous solution was extracted with EtOAc (10 mL), dried ($Na_2SO_4$) and concentrated. The residue was purified by flash chromatography ($SiO_2$) eluting with a gradient of 0 to 10% EtOAc in Cy to afford the title compound as a white powder (292 mg, 58%). $^1H$ NMR (400 MHz, chloroform-d) δ 7.38 (dd, J=5.8, 2.6 Hz, 1H), 7.17-6.97 (m, 2H), 5.17 (s, 1H), 4.32-4.13 (m, 1H), 2.41 (qt, J=7.6, 2.8 Hz, 2H), 2.06-1.90 (m, 2H), 1.85-1.65 (m, 2H). UPLC-MS: $R_t$ 2.57 min; MS (ES): m/z 290 $[M+H]^+$.

Example 1

[4-fluoro-3-[3-(methylcarbamoyl)phenyl]phenyl]N-cyclohexylcarbamate

To a solution of Ma (245.3 mg, 1.00 mmol) in DCM (5 mL) cyclohexyl isocyanate (0.14 mL, 1.10 mmol) was added followed by the addition of DMAP (6.1 mg, 0.04 mmol) and the reaction was stirred at RT for 16 h. Then the reaction mixture was concentrated and the residue was purified by flash chromatography ($SiO_2$) eluting with a gradient of 0 to 30% EtOAc in Cy to afford the title compound as colourless powder, 268 mg (72%). $^1H$ NMR (400 MHz, DMSO-$d_6$, 300K) δ 8.56 (d, J=4.5 Hz, 1H), 8.00 (s, 1H), 7.88 (d, J=7.8 Hz, 1H), 7.78 (d, J=7.9 Hz, 1H), 7.72 (d, J=7.6 Hz, 1H), 7.57 (t, J=7.7 Hz, 1H), 7.39-7.29 (m, 2H), 7.22-7.13 (m, 1H), 3.37-3.31 (m, 1H), 2.82 (d, J=4.5 Hz, 3H), 1.88-1.81 (m, 2H), 1.75-1.68 (m, 2H), 1.60-1.52 (m, 1H), 1.34-1.07 (m, 5H). UPLC-MS: Rt 2.51 min; MS (ES): m/z 371 $[M+H]^+$.

Example 2

[4-fluoro-3-(3-sulfamoylphenyl)phenyl] N-cyclohexylcarbamate

To a solution of Mb (48.1 mg, 0.18 mmol) in MeCN (3 mL) cyclohexyl isocyanate (0.02 mL, 0.20 mmol) was added followed by the addition of DMAP (1.1 mg, 0.01 mmol), and the reaction was stirred at RT for 16 h. Then the reaction mixture was concentrated and the residue was purified by flash chromatography ($SiO_2$) eluting with a gradient of 0 to 30% EtOAc in Cy to afford the title compound as colourless powder, 40 mg (57%). 1H NMR (400 MHz, DMSO-$d_6$, 300K) δ 8.01 (s, 1H), 7.88 (d, J=7.83 Hz, 1H), 7.84-7.75 (m, 2H), 7.70 (t, J=7.78 Hz, 1H), 7.43 (s, 2H), 7.41-7.35 (m, 1H), 7.31 (dd, J=2.86, 6.60 Hz, 1H), 7.26-7.18 (m, 1H), 3.36-3.30 (m, 1H), 1.87-1.80 (m, 2H), 1.75-1.68 (m, 2H), 1.61-1.52 (m, 1H), 1.32-1.21 (m, 4H), 1.17-1.08 (m, 1H). UPLC-MS: Rt 2.49 min; MS (ES): m/z 393 $[M+H]^+$.

Example 3

[3-(3-carbamoylphenyl)-4-fluoro-phenyl] N-cyclobutylcarbamate

To a solution of (3-carbamoylphenyl)boronic acid (83 mg; 0.502 mmol) in anhydrous 1,4-dioxane (3 mL) ethylene glycol (38 mg; 0.613 mmol) was added under $N_2$ atmosphere. The mixture was heated at 60° C. for 1 h under stirring and then transferred to a solution of VIc (80 mg; 0.279 mmol), Pd(dppf)$Cl_2$ (10 mg; 0.014 mmol), CsOAc (134 mg; 0.697 mmol) in dry 1,4-dioxane (5 mL). The reaction was stirred at 60° C. for 1 h, then quenched with saturated aqueous $NH_4Cl$ solution (5 mL). The aqueous solution was extracted with EtOAc (3×10 mL); the organic phase was dried ($Na_2SO_4$) and concentrated. The residue was purified by flash chromatography ($SiO_2$) eluting with a gradient of 0 to 2% MeOH in DCM, to afford the title compound as a off-white powder (35 mg, 38%). $^1H$ NMR (400 MHz, DMSO-$d_6$) δ 8.18-8.05 (m, 2H), 8.03 (s, 1H), 7.90 (d, J=7.7 Hz, 1H), 7.71 (d, J=7.4 Hz, 1H), 7.56 (t, J=7.7 Hz, 1H), 7.43 (s, 1H), 7.37-7.29 (m, 2H), 7.17 (dd, J=7.7, 4.3 Hz, 1H), 4.01 (hept, J=7.9, 7.4 Hz, 1H), 2.18 (q, J=7.7 Hz, 2H), 1.99 (p, J=9.6 Hz, 2H), 1.73-1.49 (m, 2H). UPLC-MS: Rt 2.13, MS (ES): m/z 329 $[M+H]^+$.

Example 4

[4-fluoro-3-[3-(methylcarbamoyl)phenyl]phenyl] N-cyclopentylcarbamate

A teflon capped vial was charged with Ma (98.1 mg, 0.40 mmol) and triphosgene (42.7 mg, 0.14 mmol). The vial was sealed, then evacuated and backfilled with $N_2$ (×3 times). To the solids was added dry DCM (3.0 mL), and the reaction was cooled to 0° C. Then DIPEA (0.07 mL, 0.40 mmol) was slowly added and the reaction was stirred at RT for 1 h. Cyclopentylamine (0.04 mL, 0.40 mmol) and DIPEA (0.07 mL, 0.40 mmol) were then added and the reaction stirred at RT for 16 h, then quenched with 2N HCl (5 mL). The aqueous solution was extracted with EtOAc (10 mL), dried ($Na_2SO_4$) and concentrated. The residue was purified by flash chromatography ($SiO_2$) eluting with a gradient of 0 to 2% MeOH in DCM to afford the title compound as colourless powder, 60 mg (42%). $^1$H NMR (400 MHz, DMSO-$d_6$, 300K) 8.55 (d, J=4.5 Hz, 1H), 8.00 (s, 1H), 7.88 (d, J=7.8 Hz, 1H), 7.84 (d, J=7.2 Hz, 1H), 7.72 (d, J=7.0 Hz, 1H), 7.58 (t, J=7.7 Hz, 1H), 7.39-7.30 (m, 2H), 7.22-7.14 (m, 1H), 3.91-3.81 (m, 1H), 2.82 (d, J=4.5 Hz, 3H), 1.90-1.79 (m, 2H), 1.69-1.64 (m, 2H), 1.56-1.45 (m, 4H). UPLC-MS: Rt 2.37 min; MS (ES): m/z 357 [M+H]$^+$.

Example 5

[3-(3-carbamoylphenyl)-4-fluoro-phenyl] N-cyclopentylcarbamate

To a solution of (3-carbamoylphenyl)boronic acid (59 mg; 0.359 mmol) in anhydrous 1,4-dioxane (1.5 mL) ethylene glycol (27 mg; 0.439 mmol) was added under $N_2$ atmosphere. The mixture was heated at 60° C. for 1 h and then transferred to a solution of VIb (60 mg; 0.199 mmol), Pd(dppf)$Cl_2$ (10 mg; 0.014 mmol), CsOAc (134 mg; 0.697 mmol) in dry 1,4-dioxane (5 mL). The reaction was stirred at 60° C. for 1 h, and then quenched with saturated aqueous $NH_4Cl$ solution (5 mL). The aqueous solution was extracted with EtOAc (3×10 mL); the organic phase was dried ($Na_2SO_4$) and concentrated. The residue was purified by flash chromatography ($SiO_2$) eluting with a gradient of 0 to 2% MeOH in DCM, to afford the title compound as an off-white powder (32 mg, 47%). $^1$H NMR (400 MHz, DMSO-$d_6$) δ 8.18-8.05 (m, 2H), 8.03 (s, 1H), 7.90 (d, J=7.7 Hz, 1H), 7.71 (d, J=7.4 Hz, 1H), 7.56 (t, J=7.7 Hz, 1H), 7.43 (s, 1H), 7.37-7.29 (m, 2H), 7.17 (dd, J=7.7, 4.3 Hz, 1H), 4.01 (hept, J=7.9, 7.4 Hz, 1H), 2.18 (q, J=7.7 Hz, 2H), 1.99 (p, J=9.6 Hz, 2H), 1.73-1.49 (m, 2H). UPLC-MS: Rt 2.13; MS (ES): m/z 329 [M+H]$^+$.

Example 6

[4-fluoro-3-[3-(methylcarbamoyl)phenyl]phenyl] N-cyclobutylcarbamate

A teflon capped vial was charged with Ma (98.1 mg, 0.40 mmol) and triphosgene (42.7 mg, 0.14 mmol). The vial was sealed, then evacuated and backfilled with $N_2$ (×3 times). To the solids was added DCM (3.0 mL), and the reaction was cooled to 0° C. Then DIPEA (0.07 mL, 0.40 mmol) was slowly added and the reaction was stirred at RT for 1 h. Cyclobutylamine (0.03 mL, 0.40 mmol) and DIPEA (0.07 mL, 0.40 mmol) were added and the reaction stirred at RT for 16 h, then quenched with 2N HCl. The aqueous solution was extracted with EtOAc (10 mL), dried ($Na_2SO_4$) and concentrated. The residue was purified by flash chromatography ($SiO_2$) eluting with a gradient of 0 to 2% MeOH in DCM to afford the title compound as colourless solid, 50 mg (37%). $^1$H NMR (400 MHz, DMSO-$d_6$, 300K) δ 8.55 (d, J=4.3 Hz, 1H), 8.13 (d, J=8.0 Hz, 1H), 8.00 (s, 1H), 7.88 (d, J=7.7 Hz, 1H), 7.71 (d, J=7.6 Hz, 1H), 7.57 (t, J=7.7 Hz, 1H), 7.39-7.29 (m, 2H), 7.22-7.14 (m, 1H), 4.09-3.98 (m, 1H), 2.82 (d, J=4.3 Hz, 3H), 2.25-2.14 (m, 2H), 2.05-1.95 (m, 2H), 1.68-1.56 (m, 2H). UPLC-MS: Rt 2.25 min; MS (ES): m/z 343 [M+H]$^+$.

Example 7

[4-Fluoro-3-(3-methylsulfonylphenyl)phenyl] N-cyclohexylcarbamate

To a solution of IIIc (41 mg, 0.15 mmol) in MeCN (1 mL) cyclohexyl isocyanate (0.0216 mL, 0.17 mmol) was added followed by the addition of DMAP (6.1 mg, 0.04 mmol) and the reaction was stirred at RT for 16 h. Then the reaction mixture was concentrated and the residue was purified by flash chromatography ($SiO_2$) eluting with a gradient of 0 to 4% MeOH in DCM to afford the title compound as a white powder (55 mg, 91%). $^1$H NMR (400 MHz, DMSO-$d_6$) δ 8.07 (m, 1H), 8.01-7.96 (m, 1H), 7.96-7.91 (m, 1H), 7.81-7.75 (m, 2H), 7.45-7.34 (m, 2H), 7.27-7.19 (m, 1H), 3.36-3.34 (m, 1H), 3.29 (s, 3H), 1.89-1.80 (m, 2H), 1.77-1.66 (m, 2H), 1.61-1.50 (m, 1H), 1.34-1.18 (m, 4H), 1.18-1.07 (m, 1H). UPLC-MS: Rt 2.63 min MS (ES): m/z 392 [M+H]$^+$.

Example 8

[3-(3-carbamoylphenyl)-4-(difluoromethoxy)phenyl] N-cyclohexylcarbamate

To a solution of IIId' (150 mg, 0.41 mmol) in 2-MeTHF (20 mL) cyclohexene (5 mL) was added followed by a careful addition of 10% Pd/C (50 mg). The mixture was heated at reflux for 2 h. The mixture was cooled to RT then filtered through a small pad of Celite. The filtrate was concentrated and the residue of IIIf was dissolved in MeCN (10 mL) followed by the addition of $Et_3N$ (31 μL, 0.23 mmol) and cyclohexylisocyanate (58 μL, 0.45 mmol). The mixture was stirred overnight at RT. EtOAc (50 mL) was added followed by the addition of 0.1 M HCl (20 mL). The mixture was vigorously stirred for 10 min and then the two phases were separated. The organic layer was dried ($Na_2SO_4$) and concentrated. The residue was purified by flash chromatography ($SiO_2$) eluting with a gradient of 40 to 80% EtOAc in Cy to afford the title compound as white powder (117 mg, 71%). $^1$H NMR (400 MHz, DMSO-$d_6$) δ 8.04 (bs, 1H), 7.99-7.94 (m, 1H), 7.92-7.85 (m, 1H), 7.78 (d, J=7.9 Hz, 1H), 7.68-7.62 (m, 1H), 7.54 (t, J=7.7 Hz, 1H), 7.40 (bs, 1H), 7.37-7.18 (m, 3H), 7.11 (t, J=73.6 Hz, 1H), 3.42-3.23 (m, 1H), 2.05-1.50 (m, 5H), 1.38-1.05 (m, 5H). UPLC-MS: Rt 2.49 min; MS (ES) m/z 405 [M+H]$^+$.

Example 9

[4-(difluoromethoxy)-3-[3-(methylcarbamoyl) phenyl] phenyl] N-cyclohexyl carbamate To a solution of IIIe' (157 mg, 0.41 mmol) in 2-MeTHF (20 mL) cyclohexene (5 mL) was added followed by a careful addition of 10% Pd/C (50 mg). The mixture was heated at reflux for 2 h. The mixture was cooled to RT then filtered through a small pad of Celite. The filtrate was concentrated and the residue of IIIe was dissolved in EtOH/MeCN (4 mL, 1:1). $Et_3N$ (35 μL, 0.23 mmol) was added followed by cyclohexylisocyanate (58 μL, 0.45 mmol). The mixture was stirred overnight at RT. EtOAc (50 mL) was added followed by the addition of 0.1 M HCl (20 mL). The mixture was vigorously stirred for 10 min and then the two phases were separated. The organic layer was dried ($Na_2SO_4$) and concentrated. The residue was purified by flash chromatography ($SiO_2$) eluting with a gradient of 20 to 90% EtOAc in Cy to afford the title compound as white powder (70 mg, 0.17 mmol, 41%). $^1$H NMR (400 MHz, DMSO-$d_6$) δ 8.50 (d, J=4.7 Hz, 1H), 7.94-7.88 (m, 1H), 7.89-7.82 (m, 1H), 7.78 (d, J=7.9 Hz, 2H), 7.68-7.60 (m, 1H), 7.54 (t, J=7.7 Hz, 1H), 7.38-7.15 (m, 2H), 7.11 (t, J=73.9 Hz, 1H), 3.43-3.19 (m, 1H), 2.80 (d, J=4.5 Hz, 3H), 1.93-1.46 (m, 5H), 1.36-0.98 (m, 5H). UPLC-MS: Rt 2.59 min; MS (ES) m/z 419 [M+H]$^+$.

Example 10

[4-(difluoromethoxy)-3-(3-sulfamoylphenyl)phenyl] N-cyclohexylcarbamate

To a solution of IIIf' (106 mg, 0.26 mmol) in EtOH (20 mL) cyclohexene (5 mL) was added followed by a careful addition of 10% Pd/C (50 mg). The mixture was heated at reflux for 1 h. The mixture was cooled to RT then filtered through a small pad of Celite. The filtrate was concentrated and the residue of IIIf was dissolved in EtOH/MeCN (4 mL, 1:1). $Et_3N$ (35 μL, 0.23 mmol) was added followed by cyclohexylisocyanate (53 μL, 0.41 mmol). The mixture was stirred overnight at RT. EtOAc (50 mL) was added followed by the addition of 0.1 M HCl (20 mL). The mixture was vigorously stirred for 10 min and then the two phases were separated. The organic layer was dried ($Na_2SO_4$) and concentrated. The residue was purified by flash chromatography ($SiO_2$) eluting with a gradient of 0 to 50% EtOAc in Cy to afford the title compound as a white powder (56 mg, 0.13 mmol, 49%). $^1$H NMR (400 MHz, DMSO-$d_6$) δ 7.93-7.90 (m, 1H), 7.88-7.83 (m, 1H), 7.80 (d, J=7.8 Hz, 1H), 7.76-7.62 (m, 2H), 7.40 (bs, 2H), 7.35 (d, J=8.3 Hz, 1H), 7.28-7.20 (m, 2H), 7.15 (t, J=74.1 Hz, 1H), 3.46-3.19 (m, 1H), 1.94-1.48 (m, 5H), 1.36-0.99 (m, 5H). UPLC-MS: Rt 2.54 min; MS (ES) m/z 441 $[M+H]^+$.

Example 11

[4-(difluoromethoxy)-3-(3-methylsulfonylphenyl) phenyl] N-cyclohexylcarbamate

To a solution of IIIg' (145 mg, 0.32 mmol) in 1,4-dioxane (20 mL) cyclohexene (1 mL) was added followed by a careful addition of 10% Pd/C (20 mg). The mixture was heated at reflux for 1 h. The mixture was cooled to RT then filtered through a small pad of Celite. The filtrate was concentrated and the residue of IIIg was dissolved in EtOH/MeCN (8 mL, 1:1). $Et_3N$ (27 μL, 0.19 mmol) was added followed by cyclohexylisocyanate (41 μL, 0.32 mmol). The mixture was stirred overnight at RT. EtOAc (50 mL) was added followed by the addition of 0.1 M HCl (20 mL). The mixture was vigorously stirred for 10 min and then the two phases were separated. The organic layer was dried ($Na_2SO_4$) and concentrated. The residue was purified by flash chromatography ($SiO_2$) eluting with a gradient of 0 to 50% EtOAc in Cy to afford the title compound as white powder (54 mg, 0.12 mmol, 38%). $^1$H NMR (400 MHz, DMSO-$d_6$) δ 8.03-7.99 (m, 1H), 7.99-7.93 (m, 1H), 7.90-7.70 (m, 3H), 7.34 (dd, J=8.0, 2.1 Hz, 2H), 7.25 (dd, J=8.8, 2.9 Hz, 1H), 7.17 (t, J=73.8 Hz, 1H) 3.32 (s, 1H), 3.27 (s, 3H), 2.00-1.46 (m, 5H), 1.38-1.03 (m, 5H). UPLC-MS: Rt 2.72 min; MS (ES) m/z 440 $[M+H]^+$.

Example 12

[3-(3-Carbamoylphenyl)-5-fluoro-phenyl] N-cyclohexylcarbamate

To a solution of IIIh (45 mg, 0.19 mmol) in MeCN (3 mL) and dry DMF (0.3 mL) cyclohexyl isocyanate (25 μL, 0.19 mmol) was added followed by the addition of DMAP (3.0 mg, 0.02 mmol) and the reaction was stirred at RT for 3 h. Then the reaction mixture was concentrated and the residue was purified by flash chromatography ($SiO_2$) eluting with a gradient of 0 to 2% MeOH in DCM, to afford the title compound as a white powder (45 mg, 65%). $^1$H NMR (400 MHz, DMSO-$d_6$) δ 8.20-8.16 (m, 1H), 8.13 (bs, 1H), 7.93-7.82 (m, 3H), 7.57 (t, J=7.8 Hz, 1H), 7.49 (dt, J=10.2, 2.0 Hz, 1H), 7.45 (bs, 1H), 7.39-7.36 (m, 1H), 7.08 (dt, J=9.7, 2.2 Hz, 1H), 3.37-3.35 (m, 1H), 1.85 (dd, J=9.5, 4.5 Hz, 2H), 1.72 (dd, J=9.3, 4.3 Hz, 2H), 1.57 (d, J=12.5 Hz, 1H), 1.35-1.19 (m, 4H), 1.12 (d, J=11.9 Hz, 1H). UPLC-MS: Rt 2.51 min; MS (ES): m/z 357 $[M+H]^+$.

Example 13

[3-(3-Carbamoylphenyl)-2-Fluoro-Phenyl] N-Cyclohexylcarbamate

To a solution of IIIi (70 mg, 0.30 mmol) in MeCN (3 mL) and dry DMF (0.3 mL) cyclohexyl isocyanate (46 μL, 0.36 mmol) was added followed by the addition of DMAP (2 mg, 0.02 mmol) and the reaction was stirred at RT for 2 h. Then the reaction mixture was concentrated and the residue was purified by flash chromatography ($SiO_2$) eluting with a gradient of 0 to 5% MeOH in DCM, to afford the title compound as white powder, 84 mg (79%). $^1$H NMR (400 MHz, DMSO-$d_6$) δ 8.08 (s, 1H), 8.05 (d, J=0.7 Hz, 1H), 7.92 (ddd, J=7.9, 3.4, 1.9 Hz, 2H), 7.70 (dd, J=8.0, 1.0 Hz, 1H), 7.58 (t, J=7.7 Hz, 1H), 7.47-7.39 (m, 2H), 7.35-7.28 (m, 2H), 3.34 (s, 1H), 1.97-1.78 (m, 2H), 1.78-1.63 (m, 2H), 1.62-1.51 (m, 1H), 1.35-1.03 (m, 5H). $^{13}$C NMR (101 MHz, DMSO-$d_6$) δ 167.98, 152.99, 151.95 (d, J=248.7 Hz), 139.52 (d, J=12.9 Hz), 135.22, 134.91, 131.97 (d, J=2.7 Hz), 129.36 (d, J=11.2 Hz), 129.12, 128.09 (d, J=1.8 Hz), 128.32 (d, J=1.8 Hz), 127.63, 127.57, 125.07 (d, J=4.3 Hz), 124.45, 50.48, 32.92, 25.56, 24.98. UPLC-MS: Rt 2.41 min, MS (ES): m/z 357.1 $[M+H]^+$.

Methods for Testing the Compounds

In Vitro Rat FAAH Radiometric Assay

Rat FAAH was prepared from male Sprague Dawley rat brains, homogenized in a potter in 20 mM of Tris HCl pH 7.4, 0.32 M sucrose.

The radiometric assay used to measure FAAH activity was performed in Eppendorf tubes: 50 μg of total rat brain homogenate were pre-incubated in 445.5 μL of assay buffer (50 mM Tris-HCl pH 7.4, 0.05% Fatty acid-free-bovine serum albumin (BSA)) with 4.5 μL of inhibitor (at appropriate concentration in DMSO) or DMSO alone (to measure FAAH total activity) for 10 min at 37° C. The blank (no activity control) was prepared using 445.5 μL of assay buffer and 4.5 μL of DMSO without the 50 μg of total rat brain homogenate.

After 10 min of pre-incubation with test compounds, the reaction was started by adding of 50 μL of substrate and incubating for 30 min at 37° C. The substrate was prepared in assay buffer in order to achieve the final concentration of 1 μM arachidonoyl ethanolamide (Cayman Chemical N. 90050) and 0.6 nM anandamide [ethanolamine-1-$^3$H] (American Radiolabeled Chemicals Inc, ART. 0626, Conc. 1 mCi/mL, S.A. 60 Ci/mmol). The reaction was stopped by adding cold 1:1 $CHCl_3$/MeOH. After 10 min of centrifugation (845×g at 4° C.) 600 μL of aqueous phase were transferred into scintillation vials previously filled with 3 mL of scintillation fluid (Ultima Gold™, Perkin Elmer Inc., Cat. 6013329). Radioactivity was measured by liquid scintillation counting (MicroBeta2 LumiJET Perkin Elmer Inc.). The $IC_{50}$ values of the compounds described in the Examples are reported in the following Table 2.

In Vitro Human FAAH Fluorescent Assay

Human recombinant FAAH was obtained from a HEK-293 cell line stably overexpressing human FAAH-1 enzyme. Cells were grown in Dulbecco's Modified Eagle Medium (DMEM) medium containing 10% FBS, 1% pen/strep, 1% glutamine and 500 μg/mL G418. To obtain membrane preparation cells were scraped off with cold PBS and collected by centrifugation (500×g, 10 min, 4° C.); the cell pellet was re-suspended in 20 mM Tris-HCl pH 7.4, 0.32M sucrose, disrupted by sonication (10 pulses, 5 times) and centrifuged (800×g, 15 min, 4° C.); the collected supernatant was centrifuged at 105,000×g for 1 h at 4° C. and the pellet was re-suspended in PBS.

The fluorescent assay to measure FAAH activity was performed in 96 wells black plates: 2.5 μg of human FAAH-1 membrane preparation were pre-incubated for 50 min at 37° C., in 180 L of assay buffer (50 mM TrisHCl pH 7.4, 0.05% Fatty acid-free-BSA) with 10 μL of inhibitor (at appropriate concentration in DMSO) or 10 μL DMSO to measure FAAH total activity. The background (no activity) samples were prepared using 180 μL of assay buffer without human FAAH-1 and 10 μL of DMSO. The reaction was then started by the addition of 10 μL of a 40 μM substrate solution (N. 10005098, Cayman Chemical) dissolved in ethanol, and used at a final concentration of 2 μM. The reaction was carried out for 30 min at 37° C. and fluorescence was measured with a Tecan Infinite M200 nanoquant plate reader (excitation wavelength 350 nm/emission wavelength 460 nm).

Concentrations causing half-maximal inhibition of FAAH, $IC_{50}$ values, were determined by non-linear regression analysis of the Log [concentration]/response curves generated with mean replicate values using a four parameter Hill equation curve fitting with GraphPad Prism 5 (GraphPad Software Inc., CA—USA). The $IC_{50}$ values of the compounds described in the Examples are reported in the following Table 2.

Aqueous Kinetic Solubility Assay

The aqueous kinetic solubility was determined from a 10 mM DMSO stock solution of test compound in Phosphate Buffered Saline (PBS) at pH 7.4.

The study was performed by incubation of an aliquot of 10 mM DMSO stock solution in PBS (pH 7.4) at a target concentration of 250 μM resulting in a final concentration of 2.5% DMSO. The incubation was carried out under shaking at 25° C. for 24 h followed by centrifugation. The supernatant was analyzed by UPLC/MS for the quantification of dissolved compound by UV at a specific wavelength (215 nm).

The aqueous kinetic solubility (in μM) was calculated by dividing the peak area of the supernatant by the peak area of the test compound reference and further multiplied by the concentration of the test compound reference and dilution factor.

The UPLC/MS analyses were performed on a Waters ACQUITY UPLC/MS system consisting of a SQD (Single Quadrupole Detector) Mass Spectrometer equipped with an Electrospray Ionization interface and a Photodiode Array Detector. The PDA range was 210-400 nm. The analyses were run on an ACQUITY UPLC BEH $C_{18}$ column (50×2.1 mmID, particle size 1.7 m) with a VanGuard BEH $C_{18}$ pre-column (5×2.1 mmID, particle size 1.7 μm). The mobile phase was 10 mM $NH_4OAc$ in $H_2O$ at pH 5 adjusted with AcOH (A) and 10 mM $NH_4OAc$ in MeCN—$H_2O$ (95:5) at pH 5 (B). Electrospray ionization in positive and negative mode was applied in the mass scan range 100-500 Da.

The aqueous kinetic solubility data of selected compounds described in the Examples are reported in Table 3.

Pharmacokinetic Experiment and Analysis

Administration

Compounds were administered orally (PO) and intravenously (IV) to cannulated Sprague-Dawley rats at 10 and 3 mg/kg, respectively. Vehicle was: PEG400/Tween 80/Saline solution at 10/10/80 (% in volume), respectively. Three animals per dose were treated. Blood samples at 0, 15, 30, 60, 120, 240, 480 and 1440 min after administration were collected for PO arm. Blood samples at 0, 5, 15, 30, 60, 120 and 240 min after administration were collected for IV arm. Plasma was separated from blood by centrifugation for 15 min at 3500 rpm a 4° C., collected in a Eppendorf tube and frozen (−80° C.). Control animals treated with vehicle only were also included in the experimental protocol.

Preparation of Samples, Standard Curve and QC Samples for UPLC-MS Analysis

Samples were thawed in an ice bath and after a short centrifugation transferred (50 μL) into a 96-deepwell plate and added with 150 μL of acetonitrile spiked with 200 nM Warfarin (the Internal Standard, I.S.). After agitation (3 min) the plate was centrifuged at 3000 g for 10 min at 4° C. 80 μL of supernatant was then transferred in a 96-well plate and added with 80 μL of water. Standard compound was spiked in neat solvent (PBS pH 7.4 added with 10% acetonitrile) to prepare a calibration curve over the 1 nM-10 μM range. Three quality controls (QCs) samples were also prepared spiking the compound in blank rat plasma to final 20, 200 and 2000 nM concentrations. Calibrators and QCs were crashed with acetonitrile spiked with the I.S. as described for the plasma samples. Dosing solutions, previously diluted 2000 fold in the neat solvent were also included in the samples and tested.

UPLC-MS/MS Analysis

Compounds plasma levels were monitored on a Xevo TQ UPLC-MS/MS system (Waters, Milford USA), using the calibration curve and the internal standard (Warfarin). Chromatography was carried out on a Acquity BEH $C_{18}$ column (2.1×50 mmID, 1.7 m particle size, Waters, Milford USA). Flow rate was 0.5 mL/min. The mobile phase was (A) $H_2O$/0.1% formic acid; (B) MeCN/0.1% formic acid. A linear gradient was applied from 5 to 100% B in 2 min. 3 μL of each sample were loaded on column. MS parameters and multiple reaction monitoring (MRM) transitions were carefully tuned for each compound. Plasma levels data were analyzed using PKSolutions excel application (Summit Research Service, USA) to derive the most important pharmacokinetic parameters.

The oral bioavailability (F %) data, and the Area Under the Curve (AUC) data (ng×min/mL) corresponding to the IV (3 mg/kg) and PO (10 mg/kg) dose of selected compounds described in the Examples are reported in Table 3. Their F % data are in the range from 35 to 87. Closely related compounds of the known art, generically or specifically claimed in U.S. Pat. No. 7,176,201 and tested side by side for comparison showed oral bioavailability (F %) data in the range from 5 to 30 (see Table 3).

Selected Compounds

With the aim of better illustrating the present invention, without limiting it, examples of compounds according to Formula I of the invention are provided in Table 1 herein.

TABLE 1

Examples of compounds of the invention

| Example | Molecular Structure | Molecular Formula | MW | Chemical Name |
|---|---|---|---|---|
| 1 | 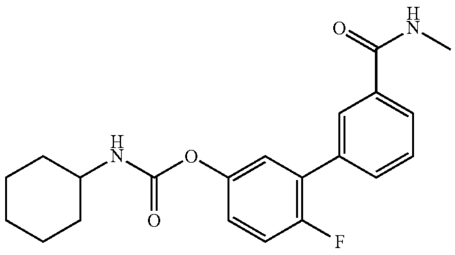 | C21 H23 F N2 O3 | 370.42 | [4-fluoro-3-[3-(methylcarbamoyl)phenyl]phenyl]N-cyclohexylcarbamate |
| 2 | 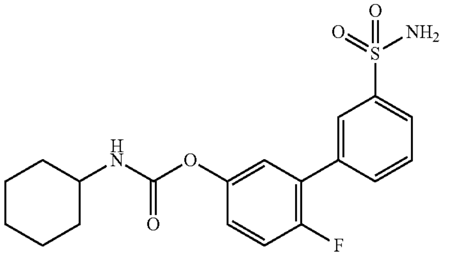 | C19 H21 F N2 O4 S | 392.44 | [4-fluoro-3-(3-sulfamoylphenyl)phenyl] N-cyclohexylcarbamate |
| 3 | 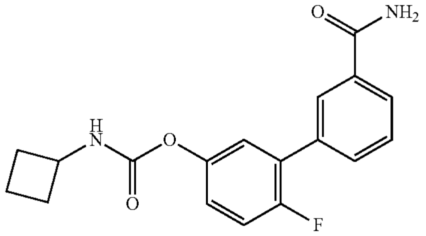 | C18 H17 F N2 O3 | 328.34 | [3-(3-carbamoylphenyl)-4-fluoro-phenyl]N-cyclobutylcarbamate |
| 4 | 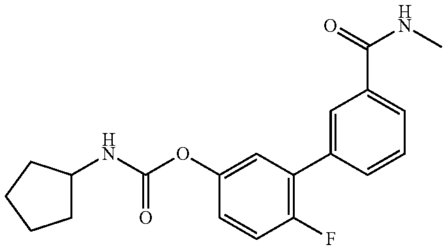 | C20 H21 F N2 O3 | 356.39 | [4-fluoro-3-[3-(methylcarbamoyl)phenyl]phenyl]N-cyclopentylcarbamate |
| 5 | 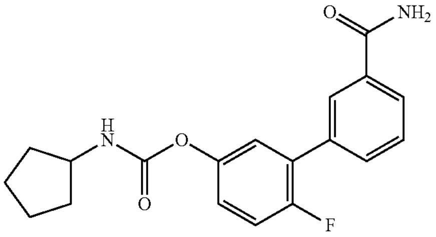 | C19 H19 F N2 O3 | 342.36 | [3-(3-carbamoylphenyl)-4-fluoro-phenyl]N-cyclopentylcarbamate |
| 6 | 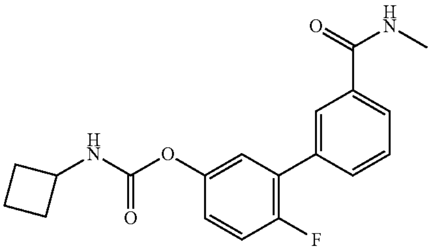 | C19 H19 F N2 O3 | 342.36 | [4-fluoro-3-[3-(methylcarbamoyl)phenyl]phenyl]N-cyclobutylcarbamate |

TABLE 1-continued

Examples of compounds of the invention

| Example | Molecular Structure | Molecular Formula | MW | Chemical Name |
| --- | --- | --- | --- | --- |
| 7 | 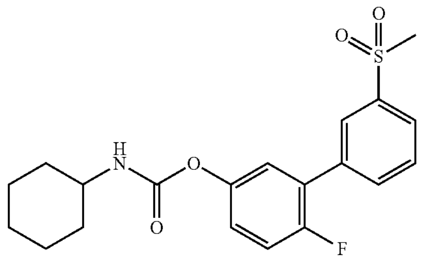 | C20 H22 F N O4 S | 391.46 | [4-fluoro-3-(3-methylsulfonylphenyl) phenyl]N-cyclohexylcarbamate |
| 8 | 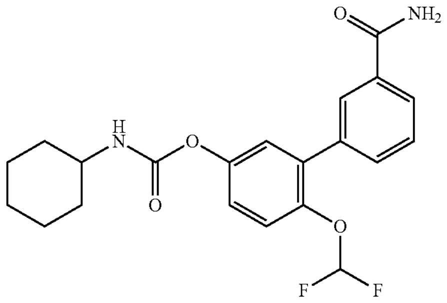 [SMILES: NC(=O)c1cccc(-c2cc(OC(=O)NC3CCCCC3)ccc2OC(F)F)c1] | C21 H22 F2 N2 O4 | 404.41 | [3-(3-carbamoylphenyl)-4-(difluoromethoxy)phenyl] N-cyclohexylcarbamate |
| 9 | 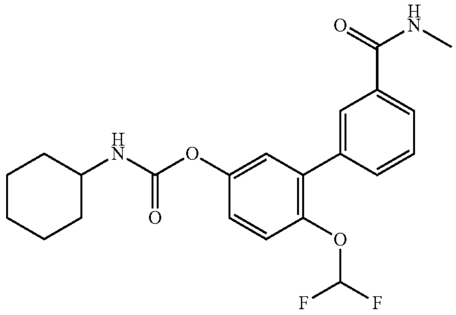 [SMILES: CNC(=O)c1cccc(-c2cc(OC(=O)NC3CCCCC3)ccc2OC(F)F)c1] | C22 H24 F2 N2 O4 | 418.43 | [4-(difluoromethoxy)-3-[3-(methylcarbamoyl)phenyl] phenyl]N-cyclohexylcarbamate |
| 10 | 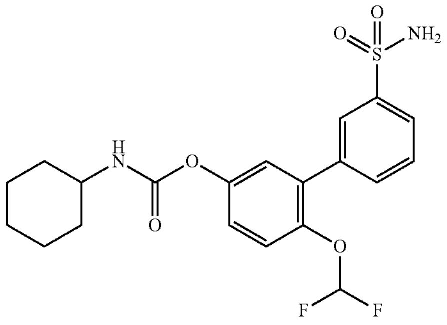 [SMILES: NS(=O)(=O)c1cccc(-c2cc(OC(=O)NC3CCCCC3)ccc2OC(F)F)c1] | C20 H22 F2 N2 O5 S | 440.46 | [4-(difluoromethoxy)-3-(3-sulfamoylphenyl)phenyl] N-cyclohexylcarbamate |
| 11 | 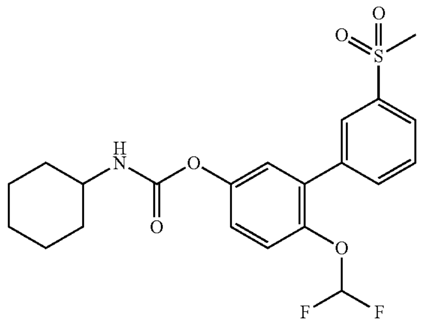 [SMILES: CS(=O)(=O)c1cccc(-c2cc(OC(=O)NC3CCCCC3)ccc2OC(F)F)c1] | C21 H23 F2 N O5 S | 439.47 | [4-(difluoromethoxy)-3-(3-methylsulfonylphenyl) phenyl]N-cyclohexylcarbamate |

TABLE 1-continued

| Examples of compounds of the invention | | | | |
|---|---|---|---|---|
| Example | Molecular Structure | Molecular Formula | MW | Chemical Name |
| 12 | 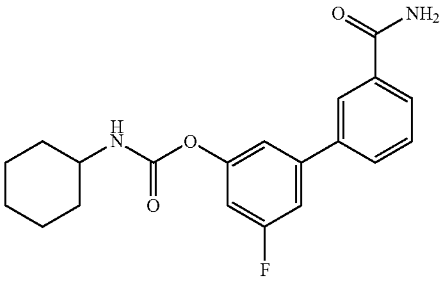 [SMILES: NC(=O)c1cccc(-c2cc(F)cc(OC(=O)NC3CCCCC3)c2)c1] | C20 H21 F N2 O3 | 356.39 | [3-(3-carbamoylphenyl)-5-fluoro-phenyl]N-cyclohexylcarbamate |
| 13 | 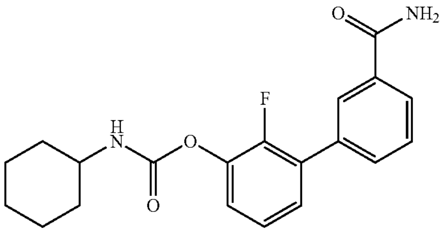 [SMILES: NC(=O)c1cccc(-c2cccc(OC(=O)NC3CCCCC3)c2F)c1] | C20 H21 F N2 O3 | 356.39 | [3-(3-carbamoylphenyl)-2-fluoro-phenyl]N-cyclohexylcarbamate |

Biological Data of Selected Compounds

TABLE 2

| $IC_{50}$ values of selected compounds of the invention on rat (r-FAAH) and human FAAH (h-FAAH) | | |
|---|---|---|
| Example | r-FAAH $IC_{50}$ (nM) | h-FAAH $IC_{50}$ (nM) |
| 1 | 1.4 | 12 |
| 2 | 0.7 | 11 |
| 3 | 0.9 | 1.8 |
| 4 | 3.9 | 2.9 |
| 5 | 2.9 | 0.84 |
| 6 | 5.1 | 6.6 |

TABLE 2-continued

| $IC_{50}$ values of selected compounds of the invention on rat (r-FAAH) and human FAAH (h-FAAH) | | |
|---|---|---|
| Example | r-FAAH $IC_{50}$ (nM) | h-FAAH $IC_{50}$ (nM) |
| 7 | 8.9 | 4.9 |
| 8 | 1.4 | 8.2 |
| 9 | 3.5 | 12 |
| 10 | 8.2 | 9.2 |
| 11 | 2.9 | 6.5 |
| 12 | 0.23 | 0.87 |
| 13 | 1.9 | 0.89 |

TABLE 3

| Comparison of kinetic solubility and oral bioavailability (F %) data of selected compounds described in the Examples side by side to closest analogues from the known art | | | | |
|---|---|---|---|---|
| Structure/ Example | Kinetic solubility (μM) PBS pH 7.4 | AUC (ng • min/mL) IV (3 mg/kg) | AUC (ng • min/mL) PO (10 mg/kg) | Oral bioavailability (F %) |
| 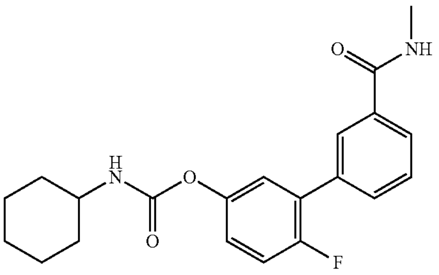 [SMILES: CNC(=O)c1cccc(-c2cc(OC(=O)NC3CCCCC3)ccc2F)c1] 1 | 28 | 76692 | 221757 | 87 |

TABLE 3-continued
Comparison of kinetic solubility and oral bioavailability (F %) data of selected compounds described in the Examples side by side to closest analogues from the known art
| Structure/ Example | Kinetic solubility (μM) PBS pH 7.4 | AUC (ng • min/mL) IV (3 mg/kg) | AUC (ng • min/mL) PO (10 mg/kg) | Oral bioavailability (F %) |
|---|---|---|---|---|
| 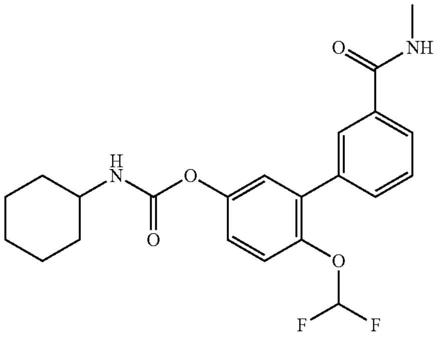 [SMILES: CNC(=O)c1cccc(-c2cc(OC(=O)NC3CCCCC3)ccc2OC(F)F)c1] 9 | 8 | 83553 | 148545 | 53 |
| 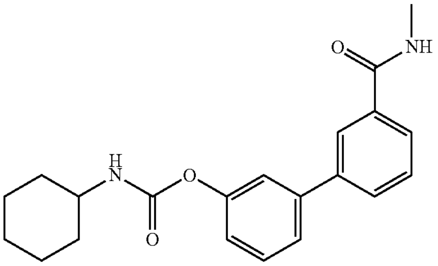 [SMILES: CNC(=O)c1cccc(-c2cccc(OC(=O)NC3CCCCC3)c2)c1] comparison compound | 18 | 91360 | 90205 | 30 |
| 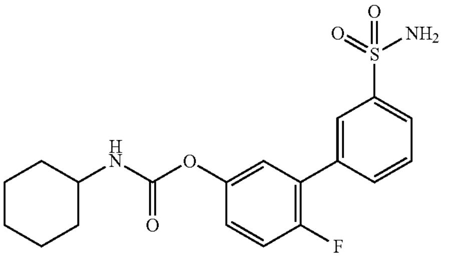 [SMILES: NS(=O)(=O)c1cccc(-c2cc(OC(=O)NC3CCCCC3)ccc2F)c1] 2 | 28 | 44755 | 52031 | 35 |
| 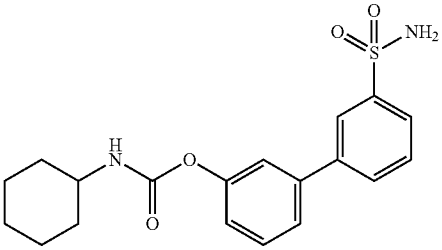 [SMILES: NS(=O)(=O)c1cccc(-c2cccc(OC(=O)NC3CCCCC3)c2)c1] comparison compound | 7 | 43512 | 30126 | 21 |
| 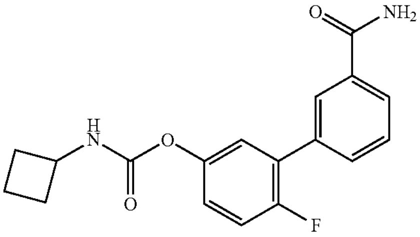 [SMILES: NC(=O)c1cccc(-c2cc(OC(=O)NC3CCC3)ccc2F)c1] 3 | 33 | 29893 | 78686 | 79 |

TABLE 3-continued

Comparison of kinetic solubility and oral bioavailability (F %) data of selected compounds described in the Examples side by side to closest analogues from the known art

| Structure/ Example | | Kinetic solubility (μM) PBS pH 7.4 | AUC (ng • min/mL) IV (3 mg/kg) | AUC (ng • min/mL) PO (10 mg/kg) | Oral bioavailability (F %) |
| --- | --- | --- | --- | --- | --- |
| 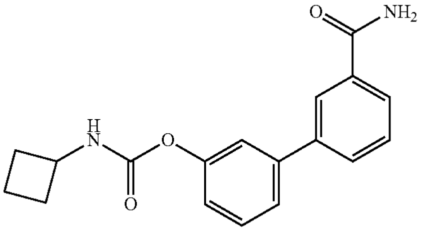 [SMILES: NC(=O)c1cccc(-c2cccc(OC(=O)NC3CCC3)c2)c1] comparison compound | | 6 | 53476 | 69576 | 39 |
| 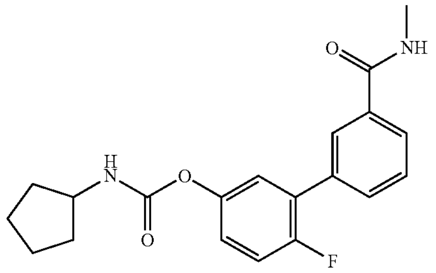 [SMILES: CNC(=O)c1cccc(-c2cc(OC(=O)NC3CCCC3)ccc2F)c1] | 4 | 96 | nd | nd | nd |
| 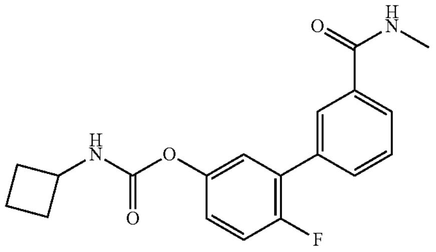 [SMILES: CNC(=O)c1cccc(-c2cc(OC(=O)NC3CCC3)ccc2F)c1] | 6 | 183 | nd | nd | nd |
| 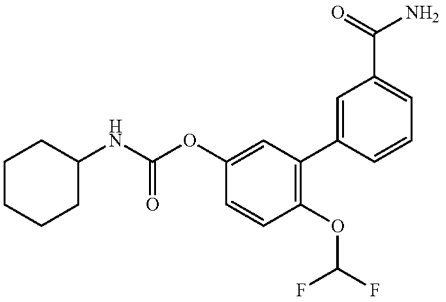 [SMILES: NC(=O)c1cccc(-c2cc(OC(=O)NC3CCCCC3)ccc2OC(F)F)c1] | 8 | 44 | 126463 | 145726 | 35 |
| 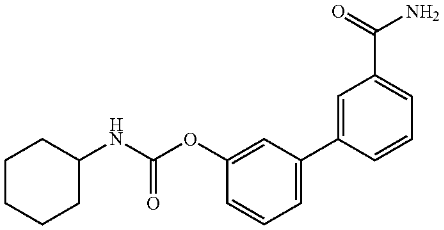 [SMILES: NC(=O)c1cccc(-c2cccc(OC(=O)NC3CCCCC3)c2)c1] comparison compound | | 1 | 153810 | 26752 | 5 |

TABLE 3-continued

Comparison of kinetic solubility and oral bioavailability (F %) data of selected compounds described in the Examples side by side to closest analogues from the known art

| Structure/ Example | Kinetic solubility (μM) PBS pH 7.4 | AUC (ng • min/mL) IV (3 mg/kg) | AUC (ng • min/mL) PO (10 mg/kg) | Oral bioavailability (F %) |
|---|---|---|---|---|
| 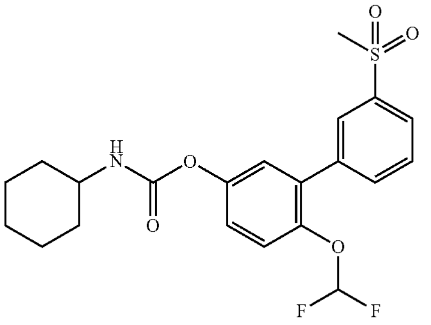 [SMILES: CS(=O)(=O)c1cccc(-c2cc(OC(=O)NC3CCCCC3)ccc2OC(F)F)c1] 11 | 12 | nd | nd | nd |

nd = not determined

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The invention claimed is:

1. A compound, or a pharmaceutically acceptable salt thereof, of formula:

(I)

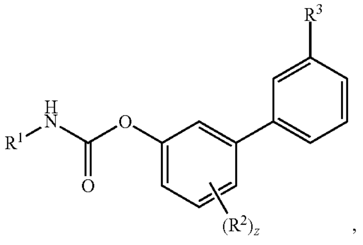

, wherein, $R^1$ is substituted or unsubstituted cycloalkyl, substituted or unsubstituted heterocycloalkyl, substituted or unsubstituted aryl, or substituted or unsubstituted heteroaryl;

$R^2$ is independently halogen, $—CX_3$, $—OCX_3$,or $—OCHX_2$;

$R^3$ is $—SO_2R^6$, $—SO_2NR^4R^5$, or $—C(O)NR^4R^5$;

$R^4$, $R^5$, and $R^6$ are independently hydrogen, substituted or unsubstituted $C_1$-$C_8$ alkyl or substituted or unsubstituted 2 to 8 membered heteroalkyl; where $R^4$ and $R^5$ are optionally joined to form a substituted or unsubstituted 4 to 8 membered heterocycloalkyl or substituted or unsubstituted 5 to 6 membered heteroaryl;

the symbol z is an integer from 1 to 4; and

X is —F, —Cl, —Br, or —I;

with the proviso that the compound is not

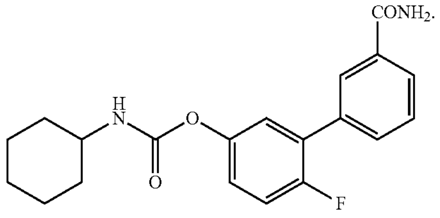 [SMILES: NC(=O)c1cccc(-c2cc(OC(=O)NC3CCCCC3)ccc2F)c1]

2. The compound of claim 1, wherein the compound is of formula:

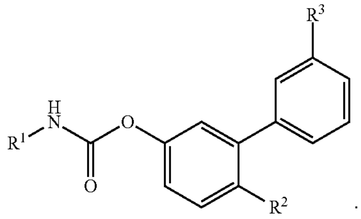

.

3. The compound of claim 1, wherein the compound is of formula:

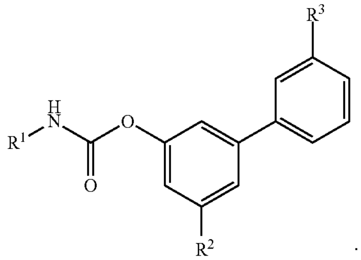

.

4. The compound of claim 1, wherein the compound is of formula:

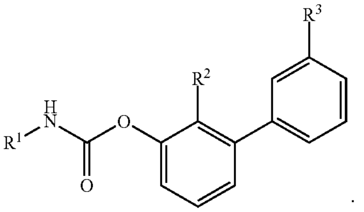

5. The compound of claim 1, wherein $R^1$ is unsubstituted $C_3$-$C_8$ cycloalkyl or unsubstituted 3 to 8 membered heterocycloalkyl.

6. The compound of claim 1, wherein $R^2$ is independently halogen or —$OCHX_2$.

7. The compound of claim 1, wherein $R^3$ is —C(O)$NR^4R^5$.

8. The compound of claim 1, wherein $R^3$ is —$SO_2NR^4R^5$.

9. The compound of claim 1, wherein $R^4$ is hydrogen or unsubstituted $C_1$-$C_4$ alkyl.

10. The compound of claim 1, wherein $R^5$ is hydrogen or unsubstituted $C_1$-$C_4$ alkyl.

11. The compound of claim 1, wherein $R^3$ is —$SO_2R^6$.

12. The compound of claim 11, wherein $R^6$ is unsubstituted methyl.

13. The compound of claim 1, wherein $R^1$ is cyclobutyl, cyclopentyl, or cyclohexyl;

$R^2$ is —F or —$OCHF_2$;

$R^3$ is —$SO_2NH_2$, —$SO_2NHMe$, —$SO_2NMe_2$, —$CONH_2$, —CONHMe, —$CONMe_2$, or —$SO_2Me$; and z is 1.

14. The compound of claim 1, wherein the compound is not

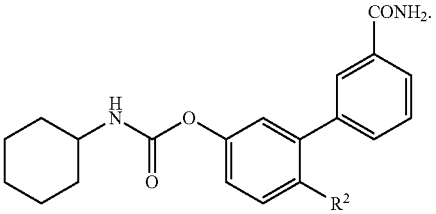

15. The compound of claim 1, wherein the compound is

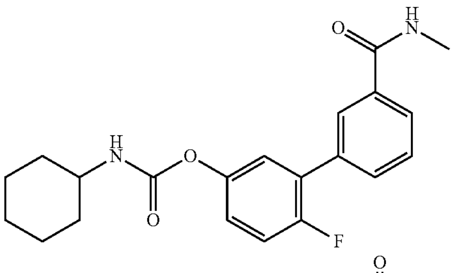

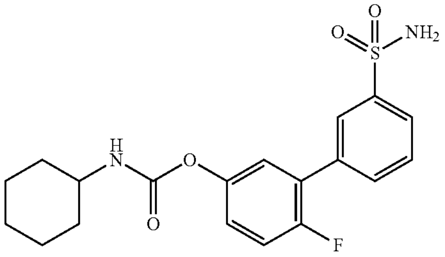

-continued

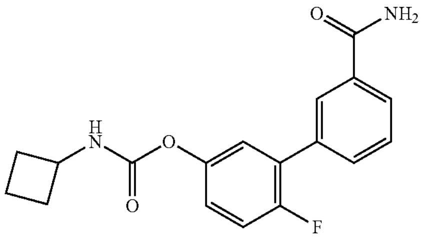

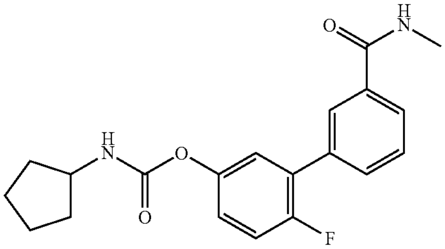

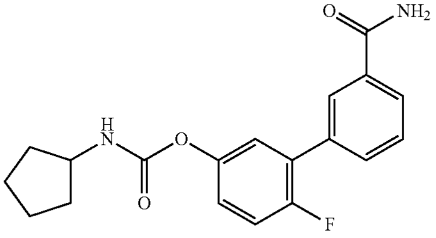

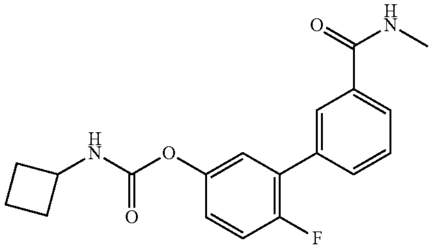

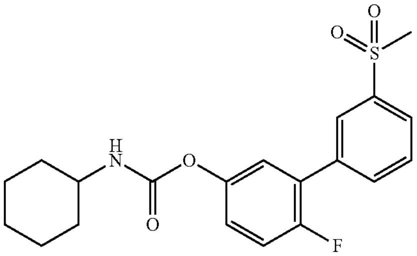

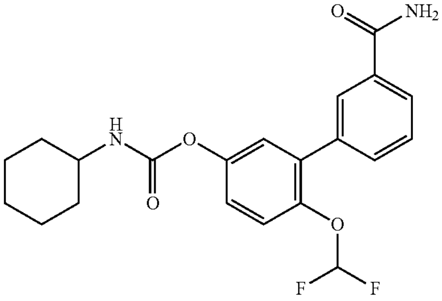

-continued

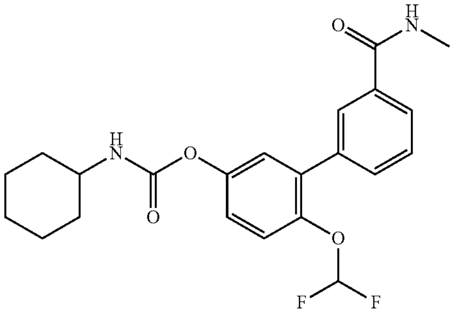

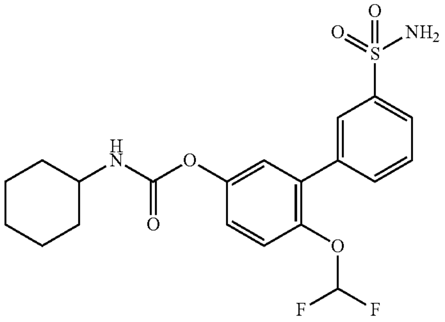

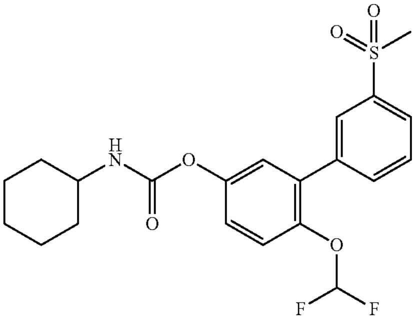

-continued

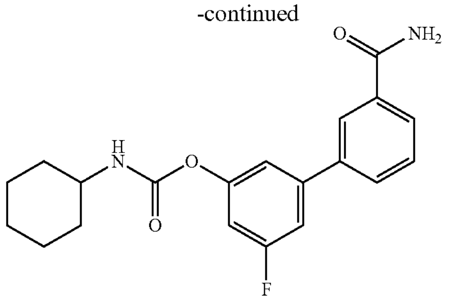

or

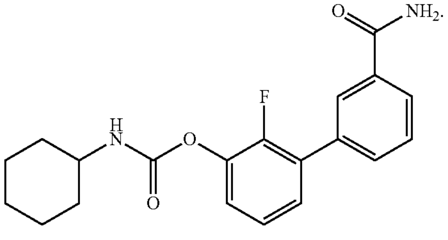

.

16. The compound of claim 1, wherein the compound has an oral bioavailability of greater than 35% in a subject.

17. A pharmaceutical composition comprising a pharmaceutically acceptable excipient and a compound, or a pharmaceutically acceptable salt thereof, of claim 1.

18. A method of treating reduced appetite, gastric damage, enteric damage, tobacco smoking, substance abuse, anxiety, post-traumatic stress disorder, schizophrenia, pain, inflammation, or ocular glaucoma, in a subject comprising administering to the subject a compound of claim 1, or pharmaceutically acceptable salt thereof.

19. A method of increasing the level of a fatty acid ethanolamide (FAE) in a subject, comprising administering to the subject a compound of claim 1, or pharmaceutically acceptable salt thereof.

20. A method of inhibiting the level of activity of FAAH in a subject, comprising administering to the subject a compound of claim 1, or pharmaceutically acceptable salt thereof.

* * * * *